US012653863B2

(12) United States Patent
Smith et al.

(10) Patent No.: US 12,653,863 B2

(45) Date of Patent: Jun. 16, 2026

(54) FGF21 COMPOSITIONS FOR TREATMENT OR PREVENTION OF NEOVASCULARIZATION OF THE EYE AND METHODS THEREFOR

(71) Applicant: Children's Medical Center Corporation, Boston, MA (US)

(72) Inventors: Lois Smith, West Newton, MA (US); Zhongjie Fu, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 17/727,120

(22) Filed: Apr. 22, 2022

(65) Prior Publication Data

US 2023/0088633 A1 Mar. 23, 2023

Related U.S. Application Data

(63) Continuation of application No. 16/483,034, filed as application No. PCT/US2018/016476 on Feb. 1, 2018, now abandoned.

(60) Provisional application No. 62/595,917, filed on Dec. 7, 2017, provisional application No. 62/453,352, filed on Feb. 1, 2017.

(51) Int. Cl.

| | |
|---|---|
| ***A61K 38/18*** | (2006.01) |
| ***A61K 9/00*** | (2006.01) |
| ***A61K 47/60*** | (2017.01) |
| ***A61K 47/68*** | (2017.01) |
| ***A61P 27/02*** | (2006.01) |

(52) U.S. Cl.

CPC ........ *A61K 38/1825* (2013.01); *A61K 9/0048* (2013.01); *A61K 47/60* (2017.08); *A61K 47/6811* (2017.08); *A61K 47/6879* (2017.08); *A61P 27/02* (2018.01)

(58) Field of Classification Search

None

See application file for complete search history.

(56) References Cited

U.S. PATENT DOCUMENTS

| | | | |
|---|---|---|---|
| 8,188,040 | B2 | 5/2012 | Belouski et al. |
| 8,722,622 | B2 | 5/2014 | Das et al. |
| 9,458,214 | B2 | 10/2016 | Boettcher et al. |
| 2002/0194630 | A1 | 12/2002 | Manning, Jr. et al. |
| 2007/0248597 | A1 | 10/2007 | Henley et al. |
| 2009/0111742 | A1 | 4/2009 | Kharitonenkov et al. |
| 2011/0002845 | A1 | 1/2011 | Cheng et al. |
| 2014/0038446 | A1 | 2/2014 | Yu et al. |
| 2015/0038446 | A1 | 2/2015 | Ambati et al. |
| 2016/0115542 | A1 | 4/2016 | Yamamoto et al. |
| 2016/0263190 | A1 | 9/2016 | Eveleth et al. |
| 2020/0000880 | A1 | 1/2020 | Smith et al. |

OTHER PUBLICATIONS

Vyawahare H, Shinde P (Sep. 26, 2022) Age-Related Macular Degeneration: Epidemiology, Pathophysiology, Diagnosis, and Treatment. Cureus 14(9): e29583. DOI 10.7759/cureus.29583.*
Senthil et al., Eye (2017) 31, 741-748.*
Hellstrom et al., Lancet 2013; 382: 1445-57. Published Online Jun. 17, 2013 http://dx.doi.org/10.1016/S0140-6736(13)60178-6.*
Khodabande et al., Ophthalmol Ther (2019) 8:155-175, https://doi.org/10.1007/s40123-019-0170-1.*
Fu et al., Fibroblast Growth Factor 21 Protects Photoreceptor Function in Type 1 Diabetic Mice. Diabetes. May 2018;67(5):974-985.
Fu et al., FGF21 Administration Suppresses Retinal and Choroidal Neovascularization in Mice. Cell Rep. Feb. 14, 2017;18(7):1606-1613.
Giragossian et al., Mechanistic investigation of the preclinical pharmacokinetics and interspecies scaling of PF-05231023, a fibroblast growth factor 21-antibody protein conjugate. Drug Metab Dispos. Jun. 2015;43(6):803-11.
Huang et al., Development of a novel long-acting antidiabetic FGF21 mimetic by targeted conjugation to a scaffold antibody. J Pharmacol Exp Ther. Aug. 2013;346(2):270-80.
Lin et al., Serum fibroblast growth factor 21 levels are correlated with the severity of diabetic retinopathy. J Diabetes Res. 2014;2014:929756.
Mohamed et al., Hyperglycemia as a risk factor for the development of retinopathy of prematurity. BMC Pediatr. May 16, 2013;13:78.
Reitman, FGF21 mimetic shows therapeutic promise. Cell Metab. Sep. 3, 2013;18(3):307-9.
Talukdar et al., A Long-Acting FGF21 Molecule, PF-05231023, Decreases Body Weight and Improves Lipid Profile in Non-human Primates and Type 2 Diabetic Subjects. Cell Metab. Mar. 8, 2016;23(3):427-40.
Basir et al., The association between fibroblast growth factor 21 with diabetes retinopathy among type 2 diabetes mellitus patients: a systematic review, meta-analysis, and meta-regression. PeerJ. Dec. 13, 2024;12:e18308. doi: 10.7717/peerj.18308. 20 pages.
Fu et al., FGF21 via mitochondrial lipid oxidation promotes physiological vascularization in a mouse model of Phase I ROP. Angiogenesis. Aug. 2023;26(3):409-421. doi: 10.1007/s10456-023-09872-x. Epub Mar. 21, 2023.
Fu et al., Retinal glial remodeling by FGF21 preserves retinal function during photoreceptor degeneration. iScience. Apr. 23, 2021;24:102376. doi: 10.1016/j.isci.2021.102376. 30 pages.
Heidari et al., The serum fibroblast growth factor 21 is correlated with retinopathy in patients with type 2 diabetes mellitus. Diabetes Metab Syndr. Nov.-Dec. 2021;15(6):102296. doi: 10.1016/j.dsx.2021.102296. Epub Sep. 24, 2021. 6 pages.
Tomita et al., Long-Acting FGF21 Inhibits Retinal Vascular Leakage in In Vivo and In Vitro Models. Int J Mol Sci. Feb. 11, 2020;21(4):1188. doi: 10.3390/ijms21041188. 13 pages.

* cited by examiner

*Primary Examiner* — Marianne P Allen

(74) *Attorney, Agent, or Firm* — Wolf, Greenfield & Sacks, P.C.

(57) ABSTRACT

The instant disclosure provides methods and compositions related to discovery of a long-acting FGF21 as a therapeutic target for treatment or prevention of neovascular eye diseases or disorders that are characterized by angiogenesis, or of vascular diseases of the eye. Therapeutic and/or prophylactic uses and compositions of long-acting FGF21 are described.

12 Claims, 46 Drawing Sheets

Specification includes a Sequence Listing.

ΔH1-hFGF21(A129C)

PIPDS SPLLQ FGGQV RQRYL YTDDA QQTEA HLEIR EDGTV GGAAD

QSPES LLQLK ALKPG VIQIL GVKTS RFLCQ RPDGA LYGSL HFDPE

ACSFR ELLLE DGYNV YQSEA HGLPL HLPGN KSPHR DPCPR GPARF

LPLPG LPPAL PEPPG ILAPQ PPDVG SSDPL SMVGP SQGRS PSYAS

FGF21 COMPOSITIONS FOR TREATMENT OR PREVENTION OF NEOVASCULARIZATION OF THE EYE AND METHODS THEREFOR

CROSS REFERENCE TO RELATED APPLICATION

This application is a Continuation of U.S. application Ser. No.: 16/483,034, filed Aug. 1, 2019, which is a National Stage Application filed under 35 U.S.C. § 371, of International Patent Application No. PCT/US2018/016476, filed Feb. 1, 2018, which claims the benefit of and priority to U.S. Provisional Application No.: 62/595,917, filed Dec. 7, 2017 and U.S. Provisional Application No.: 62/453,352, filed Feb. 1, 2017. The entire contents of which are hereby incorporated by reference in their entirety.

FEDERALLY SPONSORED RESEARCH

This invention was made with government support under Grant Numbers EY024864, EY022275, EY017017, and HD018655, awarded by the National Institutes of Health. The Government has certain rights in the invention.

INCORPORATION BY REFERENCE OF SEQUENCE LISTING

The contents of the sequence listing text file named “048218-551001WO_Sequence_Listing_txt”, which was created on Jul. 31, 2019 and is 59,404 bytes in size, are incorporated herein by reference in its entirety.

BACKGROUND OF THE INVENTION

Pathological neovascularization, a leading cause of blindness, is seen in retinopathy of prematurity, diabetic retinopathy and age related macular degeneration. There is currently no cure for retinopathy of prematurity, diabetic retinopathy, and age related macular degeneration. Therefore, there is an unmet need for treatments of retinopathy of prematurity, diabetic retinopathy, and age related macular degeneration that ameliorate and/or prevent pathological neovascularization.

SUMMARY OF THE INVENTION

The instant disclosure relates, at least in part, to the discovery of FGF21 as a therapeutic target for pathologic vessel growth in patients with neovascular eye diseases including retinopathy of prematurity, diabetic retinopathy and age-related macular degeneration. In certain aspects, stable and/or stabilized forms of FGF21 (i.e., long-acting FGF21) are used to treat or prevent neovascular eye diseases. In certain aspects of the disclosure, it is also identified that targeting of the FGF21 pathway as described herein can exert a therapeutic effect for neurovascular diseases of the eye such as diabetic retinopathy, retinopathy of prematurity (ROP), retinitis pigmentosa (RP), age-related macular degeneration (AMD) and macular telangiectasia (MacTel). The disclosure provides a method for treating or preventing neovascular eye diseases in a subject, the method involving (a) identifying a subject having or at risk of neovascular eye disease; and (b) administering a long-acting FGF21 composition to the subject, thereby treating or preventing neovascular eye disease in the subject.

In one aspect, the disclosure provides a method for treating or preventing neovascularization and/or angiogenesis in the eye of a subject, the method involving identifying a subject having or at risk of neovascularization and/or angiogenesis in the eye; and administering a pharmaceutical composition including a stabilized FGF21 agent to the subject, thereby treating or preventing neovascularization and/or angiogenesis in the eye of the subject.

In one embodiment, the subject has or is at risk of developing neovascular retinopathy. In another embodiment, the subject has or is at risk of developing diabetic retinopathy in Type I or Type II diabetes, retinopathy of prematurity (ROP), retinitis pigmentosa (RP) and/or macular telangiectasia (MacTel).

In another embodiment, choroidal neovascularization and/or angiogenesis is treated or prevented.

Optionally, retinal neovascularization and/or angiogenesis in the retinal cells of the eye is treated or prevented.

In one embodiment, the stabilized FGF21 agent comprises an FGF21 polypeptide conjugated to an antibody scaffold. Optionally, the FGF21 polypeptide is a modified FGF21. In certain embodiments, the modified FGF21 is dHis/Ala129Cys, optionally the modified FGF21 is conjugated at Cys 129 to the antibody scaffold. Optionally, two or more FGF21 polypeptide molecules are conjugated to one antibody scaffold—the two or more FGF21 polypeptide molecules can be the same or different from each other. In some embodiments, the antibody scaffold is a CovX-2000 scaffold.

In certain embodiments, the stabilized FGF21 agent is a long acting FGF21 analog, optionally PF-05231023.

In one embodiment, the stabilized FGF21 agent possesses a half-life of at least 1.5× the half-life of a native FGF21 peptide when assayed for stability under identical conditions, optionally at least 2× the half-life of a native FGF21 peptide, optionally at least 3× the half-life of a native FGF21 peptide, optionally at least 4× the half-life of a native FGF21 peptide, optionally at least 5× the half-life of a native FGF21 peptide, optionally at least 8× the half-life of a native FGF21 peptide, optionally at least 10× the half-life of a native FGF21 peptide, optionally at least 12× the half-life of a native FGF21 peptide, optionally at least 15× the half-life of a native FGF21 peptide, optionally at least 20× the half-life of a native FGF21 peptide, optionally at least 30× the half-life of a native FGF21 peptide, optionally at least 40× the half-life of a native FGF21 peptide, optionally at least 50× the half-life of a native FGF21 peptide, optionally at least 60× the half-life of a native FGF21 peptide or optionally at least 70× the half-life of a native FGF21 peptide.

In certain embodiments, the stabilized FGF21 agent possesses a half-life of at least 0.8 h in the circulation of a mammal, optionally at least 1 h, at least 2 h, at least 3 h, at least 4 h, at least 5 h, at least 7 h, at least 10 h, at least 15 h, at least 20 h, at least 25 h, at least 28 h or at least 30 h in the circulation of a mammal, optionally wherein the mammal is human.

In one embodiment, the pharmaceutical composition is administered to the eye of the subject, optionally by intravitreal injection.

In some embodiments, the pharmaceutical composition is administered in an amount sufficient to increase retinal levels of APN in the subject.

Another aspect of the disclosure provides a pharmaceutical composition for use in treating or preventing neovascularization and/or angiogenesis in the eye of a subject that includes a stabilized FGF21 agent and a pharmaceutically acceptable carrier.

An additional aspect of the disclosure provides for use of a stabilized FGF21 agent in the preparation of a medicament for treatment or prevention of neovascular retinopathy, diabetic retinopathy in type I diabetes, retinopathy of prematurity (ROP), retinitis pigmentosa (RP) or macular telangiectasia (MacTel) in a subject.

A further aspect of the disclosure provides a method of treating a subject suffering from diabetic retinopathy, retinitis pigmentosa or age-related macular degeneration involving administering an effective amount of a long acting FGF-21 agent to the subject.

In one embodiment, the age-related macular degeneration is wet macular degeneration or dry macular degeneration.

In another embodiment, the diabetic retinopathy is proliferative diabetic retinopathy or non-proliferative diabetic retinopathy.

In an additional embodiment, the retinitis pigmentosa is autosomal recessive, autosomal dominant or X-linked.

In certain embodiments, the long acting FGF-21 agent is two ΔHis1/A129C modified FGF-21 peptides each conjugated to a Fab region of a humanized IgG1k mAb.

Definitions

Unless defined otherwise, all technical and scientific terms used herein have the meaning commonly understood by a person skilled in the art to which this disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

An "agent" is meant any small compound, antibody, nucleic acid molecule, or peptide or fragment thereof.

As used herein, "Age-related macular degeneration," or "AMD" refers to an eye condition which causes a deterioration or breakdown of the macula, a small spot near the center of the retina and the part of the eye needed for sharp central vision. More specifically, the photoreceptor cells within the macula die off slowly, thus accounting for the progressive loss of vision.

By "ameliorate" is meant decrease, suppress, attenuate, diminish, arrest, or stabilize the development or progression of a disease.

An "agonist" as used herein is a molecule which enhances the biological function of a protein. The agonist may thereby bind to the target protein to elicit its functions. However, agonists which do not bind the protein are also envisioned. The agonist may enhance the biological function of the protein directly or indirectly. Agonists which increase expression of certain genes are envisioned within the scope of particular embodiments of the disclosure. Suitable agonists will be evident to those of skill in the art. For the present disclosure it is not necessary that the agonist enhances the function of the target protein directly. Rather, agonists are also envisioned which stabilize or enhance the function of one or more proteins upstream in a pathway that eventually leads to activation of targeted protein. Alternatively, the agonist may inhibit the function of a negative transcriptional regulator of the target protein, wherein the transcriptional regulator acts upstream in a pathway that eventually represses transcription of the target protein.

An "antagonist" may refer to a molecule that interferes with the activity or binding of another molecule, for example, by competing for the one or more binding sites of an agonist, but does not induce an active response.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Any compositions or methods provided herein can be combined with one or more of any of the other compositions and methods provided herein.

By "effective amount" is meant the amount of an agent required to ameliorate the symptoms of a disease relative to an untreated patient. The effective amount of active agent(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The phrase "longer half-life" has its ordinary meaning as understood by persons of skill in the art. Merely by way of example, and by no means as a limitation on the meaning of the term, the following description of the term is informative: any appreciable increase in the length of time in which FGF21 may be circulating and able to bind beta klotho and FGF21 receptors either in vivo or in vitro as compared to the half-life of the native FGF21 alone either in vivo or in vitro.

The term "macula" refers to a small area within the retina. The macula is the part of the retina that is responsible for central vision, allowing things to be seen clearly. Although only a small part of the retina, the macula is more sensitive to detail than the rest of the retina. Many older people develop macular degeneration as part of the body's natural aging process. Symptoms of macular degeneration include blurriness, dark areas or distortion in central vision, or even permanent loss in central vision. It usually does not affect side or peripheral vision.

The term "neovascularization" refers to the formation of functional microvascular networks with red blood cell perfusion. Neovascularization differs from angiogenesis in that angiogenesis is mainly characterized by the protrusion and outgrowth of capillary buds and sprouts from pre-existing blood vessels. Choroidal neovascularization is the formation of new microvasculature within the innermost layer of the choroid of the eye.

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

By "photoreceptor cells" refers to the bulk of neurons in the retina. The photoreceptor cells capture light energy units (photons) and register the events as electrical signals of the central nervous system. The signals are then relayed to intermediary layers of neurons in the retina that process and organize the information before it is transmitted along the optic nerve fibers to the brain.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control, e.g., a standard or control condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reduces" is meant a negative alteration of at least 10%, 25%, 50%, 75%, or 100%.

By "subject" is meant a mammal, including, but not limited to, a human or non-human mammal, such as a bovine, equine, canine, ovine, or feline.

As used herein, a "stable FGF21" or "stabilized FGF21" refers to a composition that includes an active FGF21 polypeptide and a modification (as compared to a WT, unmodified form of FGF21) that has the effect of producing a form of FGF21 agent that is more protease stable than a corresponding WT, unmodified form of FGF21 (i.e., than native FGF21). A stabilized FGF21 composition of the instant disclosure therefore possess a greater half-life than native FGF21, when assessed for stability in an art-recognized stability assay (e.g., an in vitro stability assay, e.g., in the presence of one or more proteases and/or and in vivo stability assay, e.g., when administered to the plasma, blood, saliva, etc. of a subject). Samples are analyzed for the levels of FGF21 using an ELISA in 96-well microtiter plate coated with an anti-FGF21 mAb.

In certain embodiments, a "stable FGF21" or "stabilized FGF21" of the instant disclosure can exhibit biological activity over an extended period of time, as compared to a WT, unmodified form of FGF21. For example, a "stable FGF21" or "stabilized FGF21" of the instant disclosure can exhibit biological activity (e.g., a therapeutic and/or prophylactic effect) in a subject to which such stable FGF21 is administered over a period of an hour or more, two hours or more, three hours or more, four hours or more, five hours or more, ten hours or more, twenty hours or more, a day or more, two days or more, three days or more, four days or more, five days or more, a week or more, two weeks or more, or even a month or more after a single administration of the "stable FGF21" or "stabilized FGF21". Optionally, a single dose or multiple doses of the "stable FGF21" or "stabilized FGF21" can be administered to a subject, optionally to achieve dosage to a subject within a desired (e.g., therapeutically effective) range over an extended duration of time.

A "therapeutically effective amount" is an amount sufficient to effect beneficial or desired results, including clinical results. An effective amount can be administered in one or more administrations.

As used herein, the terms "treat," treating," "treatment," and the like refer to reducing or ameliorating a disorder and/or symptoms (e.g., AMD, MacTel or other angiogenesis-associated disease or disorder of the eye, or of tumors in general) associated therewith. It will be appreciated that, although not precluded, treating a disorder or condition does not require that the disorder, condition or symptoms associated therewith be completely eliminated.

Any compositions or methods provided herein can be combined with one or more of any of the other compositions and methods provided herein.

Other features and advantages of the disclosure will be apparent to those skilled in the art from the following detailed description and claims

BRIEF DESCRIPTION OF THE DRAWINGS

FIG. 1A shows micrographs and an accompanying chart demonstrating the extent of neovascularization in retinas treated with native FGF21 (nFGF21), or a long-acting FGF21 analog (PF-05231023), or with vehicle control. n=14-19 retinas per group. One-way ANOVA was performed upon raw results, followed by Bonferroni's multiple comparisons post test. n.s.=no significance. FIG. 1B shows micrographs demonstrating observed neovascularization and quantifying fold changes observed for such neovascularization in retinas of $Fgf21^{+/+}$ and $Fgf21^{-/-}$ mice. n=12-13 retinas per group. Unpaired t test. Whole mount vessels were stained with isolectin (red), and neovascularization was pseudo-colored white. Representative images are shown. Scale bar, 1 mm. Data were presented as mean±SEM. Fold-changes were calculated in comparison to the control group.

FIG. 2A depicts a graph showing relative mRNA levels in WT P17 normal retinas for FGF21 receptors Fgfr1, Fgfr2, Fgfr3, Fgfr4 and co-receptor β-klotho (Klb) (n=6-8 pooled retinas per group). FIG. 2B depicts a graph demonstrating that in WT P17 hypoxic retinas, long-acting FGF21 agent PF-05231023 exerted an inducing effect on retinal APN (n=6 pooled retinas per group). PF-05231023 was administered from P12-16. FIG. 2C depicts micrographs and charts demonstrating that $Apn^{-/-}$ mice exhibited increased levels of neovascularization, as compared to WT mice (n=17-20 retinas per group). FIG. 2D depicts micrographs and charts demonstrating that $Apn^{-/-}$ mice treated with PF-05231023 did not show a significant response to PF-05231023 treatment (n=11-14 retinas per group). FIG. 2E depicts graphs demonstrating the effect of PF-05231023 treatment on Tnfα levels in WT or $Apn^{-/-}$ retinas (n=6-8 pooled retinas per group), where WT mice were clearly responsive to PF-05231023 treatment and $Apn^{-/-}$ retinas exhibited an ablated response. FIG. 2F depicts a schematic of the perceived role of FGF21 modulation in neovascular retinas.

FIG. 3A depicts 3 dimensional (3D) reconstruction of retinal neovessels extending from the outer plexiform layer (OPL) towards the retinal pigment epithelium (RPE). PF-05231023 (i.p. injected daily from P8-15) decreased retinal neovessel extension towards RPE seen with isolectin (red) stained vessels. FIG. 3B depicts representative images of isolectin-stained vessels in retinal whole mounts, and neovessels (lesions) are highlighted in white (bottom) (with photoreceptor layer facing up). Scale bar, 1 mm. FIG. 3C shows the result of quantifying number and area (size) of vascular lesions (n=11-18 retinas per group). FIG. 3D demonstrates that in $Vldlr^{-/-}$ retinas, PF-0523102 exerted significant effects on both Apn and Tnfα levels (n=4-6 pooled retinas per group). Data was presented as mean±SEM. Unpaired t test. Fold-changes were calculated.

FIG. 4A depicts a schematic showing an approach for laser-induced choroidal neovascularization in mice. FIG. 4B depicts representative images of isolectin-stained choroidal neovessels, in both vehicle- and PF-05231023-treated mice. The area of induced lesions was quantified (n=6-8 mice per group). Scale bar: 200 μm (top); 50 μm (bottom). FIG. 4C depicts charts that demonstrate the effect of PF-05231023 on Apn and Tnfα levels in neovascular choroid-retina complexes (n=4-6 pooled retinas per group). FIG. 4D depicts charts that demonstrate the effect of PF-05231023 on Vegfa in the three mouse models of neovascular eye diseases examined (n=6-8 pooled retinas per group). Data were presented as mean±SEM. Unpaired t test. n.s., no significance. Fold-changes were calculated.

FIG. 6A depicts WT retinas treated with PF-05231023 or vehicle control from P12-P16 (n=14-19 retinas per group). Unpaired t test. FIG. 6B depicts $Fgf21^{+/+}$ and $Fgf21^{-/-}$ retinas (n=12-13 retinas per group). Unpaired t test. FIG. 6C depicts WT and $Apn^{-/-}$ mice (n=17-20 retinas per group). Unpaired t test. FIG. 6D depicts $Apn^{-/-}$ mice treated with PF-05231023 (n=11-14 retinas per group). Unpaired t test.

FIG. 7A depicts laser-capture microdissected retinal layers and vessels from normal (N) and oxygen-induced retinopathy (OIR) P17 retinas; localization and quantitation of Fgfrl and Fgfr3 was performed using qPCR (n=6-8 pooled retinas). Unpaired t test. Scale bar: 20 μm. FIG. 7B depicts immunohistochemistry for adiponectin (green) and lectin (red) in P17 OIR retinal whole mounts. Scale bar: 40 μm. FIG. 7C depicts the effect of PF-05231023 (left) and adipoRon (right) on migrated area in HRMEC would healing assays. One-way ANOVA. FIG. 7D depicts effect of PF-05231023 (left) and adipoRon (right) on HRMEC cell viability. One-way ANOVA.

FIG. 8A depicts that FGF21 deficiency delayed normal retinal vascular development in neonatal mice. FIG. 8B depicts that FGF21 deficiency worsened hyperglycemic retinopathy in neonatal mice.

FIG. 9A shows the effects observed following administration of native FGF21 (nFGF21). FIG. 9B depicts the effects observed after administration of long-acting FGF21 (PF-05231023). As shown, administration of long-acting FGF21 improved retinal vascular growth. Unpaired t test.

FIG. 10A demonstrates that APN deficiency completely abolished long-acting FGF21 effects that would otherwise have been observed upon treatment of hyperglycemic retinopathy. FIG. 10B shows that FGF21 administration increased high-molecular-weight (HMW) and hexamer APN levels in serum. Unpaired t test.

FIG. 13A shows serum FGF21 levels measured by ELISA. n=6-8 mice per group. FIGS. 13B-13D shows results from qPCR for Fgf21, Fgfrl, β-klotho expression in diabetic WT and Akita retinas. n=3-4 mice per group. Unpaired t test.

FIG. 14A is a schematic illustration of PF-05231023 treatment in 7-to-8-month-old Akita mice. 10 mg/kg PF-05231023 was i.p. injected twice a week for a month. ERG was measured before and after treatment. ERG plots with 'white' (for maximal a-wave) and "green" (for maximal b-wave) light stimulation are shown to demonstrate the parameters: a-wave (photoreceptors), b-wave (bipolar cells), oscillatory potentials (OPs, inner retinal neurons). Photoreceptor amplitude ($Rmp_3$) and sensitivity (S), bipolar cell response amplitude ($Rmp_2$) and sensitivity ($1/K_{P2}$), inner retinal neuronal saturating energy (Em) and sensitivity ($1/i_{1/2Em}$), as well as total retinal sensitivity (Sm) were measured and calculated. FIG. 14B shows representative ERG plots in 7-to-8-month-old WT mice (black), age-matched Akita mice before (blue) and after (orange) PF-05231023 administration. FIG. 14C shows overall changes in different ERG parameters in WT mice, Akita mice before and after PF-05231023 administration. FIG. 14D shows a comparison of retinal sensitivity (Sm) in WT mice, Akita mice before and after PF-05231023 administration. n=5 to 10 mice per group. ANOVA followed by Tukey"s test.

FIG. 15A shows the correlation of post-receptor cell sensitivity ($1/K_{P2}$) with the sum of changes in photoreceptor sensitivity ($S_{Rod}$) and saturated amplitude ($R_{Rod}$) in Akita mice. n=10 eyes per group. Pearson r test. FIG. 15B shows results from qPCR of Arrestin4 and Rhodopsin in age-matched WT mice and Akita mice treated with either vehicle or PF-05231023. n=3-4 mice per group. ANOVA. FIGS. 15C-15D are photographs showing the immunohistochemistry of cones (cone arrestin, red), rods (rhodopsin, green) and nuclei (DAPI, blue) in age-matched WT mice and Akita mice treated with either vehicle or PF-05231023. GCL, ganglion cell layer; INL, inner nuclear layer; ONL, outer nuclear layer. Scale bar: 50 μm. FIG. 19E shows an optical coherence tomography (OCT) for photoreceptor inner and outer segment in age-matched wild-type (WT) mice (black line) and Akita mice treated with either vehicle (blue line) or PF-05231023 (orange line). n=4-10 mice per group. *P<0.05, **P<0.01. ANOVA.

FIG. 16A shows results from qPCR for pro-inflammatory markers (IL-1β, Vegfa, Tnfα, IL-6) and anti-inflammatory markers (IL-10, Apn) in WT and Akita mouse retinas. n=3-4 mice per group. FIG. 16B shows results from Akita mouse retinas treated with vehicle (PBS) or PF-05231023. n=3-4 mice per group. Unpaired t test. Data is presented as Mean±SEM.

FIG. 17A is a Western blot of p-AKT, AKT, NRF2 in non-diabetic WT, diabetic Akita with vehicle or PF-05231023 administration for one month. β-ACTIN was used as internal control. n=3 mice per group. ANOVA. FIG. 17B show results from qPCR of IL-1β in cone photoreceptors in vitro (661W). Oxidative stress was induced with 0.5 mM paraquat (PQ) for 1 hour. The culture medium was changed and cells were treated with 500 ng/ml PF-05231023 or vehicle for 24 hours. n=4 independent replicates. ANOVA followed by Bonferroni's multiple comparisons test. FIG. 17C shows results from qPCR of Nrf2 and Nfκb in 661W with PQ-induced oxidative stress followed by treatment with 500 ng/ml PF-05231023 or vehicle for 24 hours. n=4 independent replicates. ANOVA followed by Bonferroni's multiple comparisons test. FIG. 17D shows results from qPCR of Nrf2 in in 661W with PQ-induced oxidative stress followed by co-treatment with 500 ng/ml PF-05231023 and perifosine at 5 or 10 μM. ANOVA. FIG. 17E is a Western blot of NRF2, p-NFκB and NFκB in 661W with PQ-induced oxidative stress followed by treatment with 500 ng/ml PF-05231023 or vehicle for 24 hours. Protein lysate was isolated from 661W. β-ACTIN was used as internal control. Lane only with loading dye was negative control. n=4 independent replicates. ANOVA followed by Bonferroni's multiple comparisons test.

FIGS. 18A-18I depict a series of plots and graphs showing that PF-05231023 administration protected the retinal function in STZ-induced diabetic mice, independent of APN. FIG. 18A is a schematic of STZ-induced type 1 diabetes in C57BL/6J (WT) mice. STZ was i.p. injected in 6-to-8-week-old WT mice (Day1-2: 60 mg/kg; Day3-5: 55 mg/kg). ERG was compared in diabetic mice before and after PF-05231023 treatment (10 mg/kg i.p., twice a week). FIG. 18B depicts representative ERG plots of 7-to-8-month-old WT control mice, and WT diabetic mice before and after PF-05231023 administration. FIG. 18C depicts the overall changes in different ERG parameters in WT normal mice, WT diabetic mice before and after PF-05231023 administration. FIG. 18D depicts a comparison of retinal sensitivity (Sm) in WT normal mice, WT diabetic mice before and after PF-05231023 administration. n=3 to 5 mice per group. ANOVA followed by Tukey's test. FIG. 18E are plots of retinal sensitivity (Sm) in 7-to-8-month-old WT diabetic mice before and after PF-05231023 administration. n=3 mice per group. Paired t test. FIG. 18F show representative ERG plots of 7-to-8-month-old $Apn^{-/-}$ diabetic mice before and after PF-05231023 administration. FIG. 18G shows the overall changes in different ERG parameters in $Apn^{-/-}$ diabetic mice before and after PF-05231023 administration. FIG. 18H show plots of retinal sensitivity (Sm) in $Apn^{-/-}$ diabetic mice before and after PF-05231023 administration. n=3 mice per group. Paired t test. FIG. 18I are graphs showing results from qPCR for IL-1β in diabetic WT and $Apn^{-/-}$ mouse retinas treated with vehicle (PBS) or PF-05231023. n=3 mice per group. Unpaired t test. ERG plots with 'white" and "green" light stimulation are shown. Data was presented as Mean±SEM.

DETAILED DESCRIPTION OF THE INVENTION

Figure 1A:
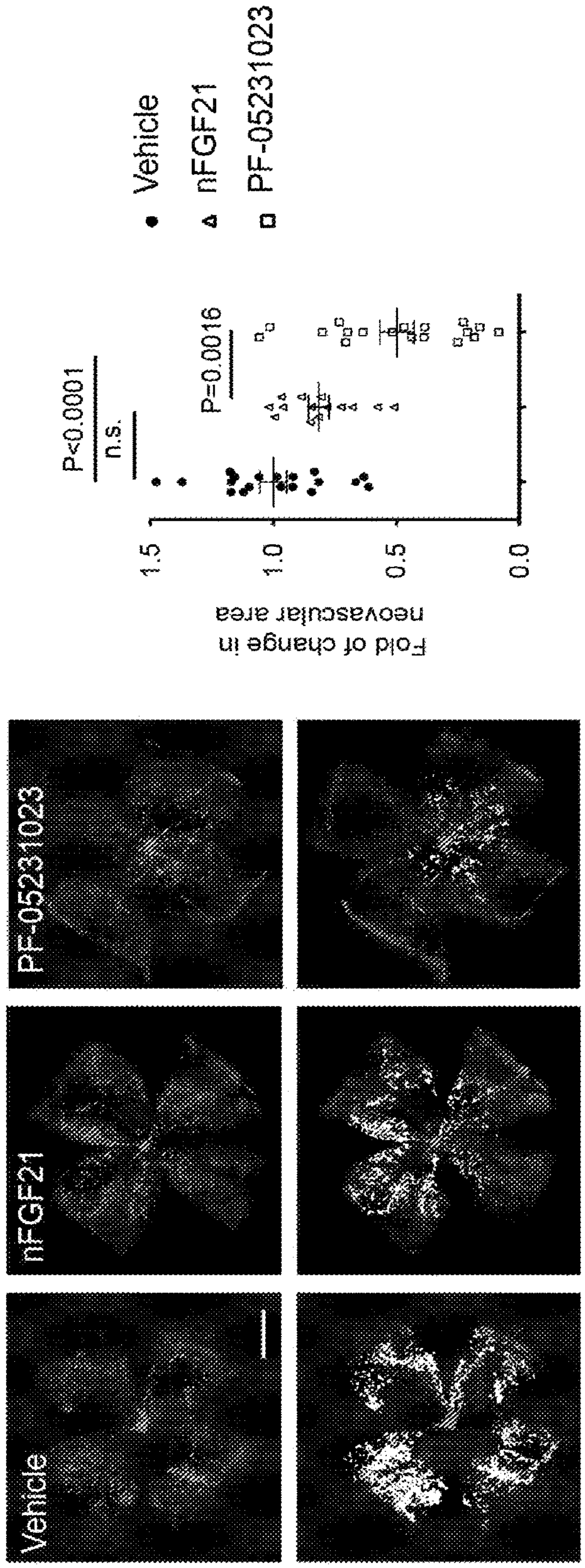
FIGS. 1A and 1B depict micrographs and charts that demonstrate FGF21 treatment (particularly stabilized/long-acting FGF21 treatment) decreased hypoxia-induced retinal neovascularization, whereas FGF21 deficiency increased hypoxia-induced retinal neovascularization. Quantification of neovascularization in P17 retinal whole mounts was performed in mouse oxygen-induced retinopathy (OIR).

The disclosure is based, at least in part, upon the discovery of FGF21 as a therapeutic target for pathologic vessel growth in patients with neovascular eye diseases including retinopathy of prematurity, diabetic retinopathy and age-related macular degeneration. In certain aspects of the disclosure, stable forms of FGF21 (i.e., long-acting FGF21) are used to treat neovascular eye diseases. In certain aspects of the disclosure, it is also identified that targeting of the FGF21 pathway as described herein can exert a therapeutic effect for neurovascular diseases of the eye such as diabetic retinopathy, retinopathy of prematurity, retinitis pigmentosa, age-related macular degeneration (AMD) and macular telangiectasia (MacTel). The disclosure provides a method for treating or preventing neovascular eye diseases in a subject, the method involving (a) identifying a subject having or at risk of neovascular eye disease; and (b) administering a long-acting FGF21 composition to the subject, thereby treating or preventing neovascular eye disease in the subject.

Pathological neovascularization, a leading cause of blindness, is seen in retinopathy of prematurity, diabetic retinopathy and age related macular degeneration. Using a mouse model of hypoxia-driven retinal neovascularization, oxygen-induced retinopathy, it was discovered that fibroblast growth factor 21 (FGF21) administration suppressed, and FGF21 deficiency worsened, retinal neovessel growth. The protective effect of long-acting FGF21 against neovessel growth was abolished in adiponectin (APN)-deficient mice, and long-acting FGF21 administration also decreased neovascular lesions in two models of neovascular age-related macular degeneration, very-low-density-lipoprotein-receptor-deficient mice having retinal angiomatous proliferation and laser-induced choroidal neovascularization. Long-acting FGF21 inhibited Tnfα expression but did not alter Vegfa expression in neovascular eyes. As described herein, FGF21 (particularly long-acting FGF21) is thereby described as a therapeutic modality for pathologic vessel growth in patients having neovascular eye diseases including retinopathy of prematurity, diabetic retinopathy and age-related macular degeneration.

Additional aspects and embodiments of the invention are described below.

Mechanism of Action

Without wishing to be bound by theory, the instant disclosure is believed to function in the following manner. Pathological retinal neovessel growth is a major cause of vision loss in retinopathy of prematurity in premature infants, in macular telangiectasia, diabetic retinopathy and age-related macular degeneration in adults. Uncontrolled neovessel growth is driven by the need for oxygen and for energy substrates (Hellstrom et al., 2013; Joyal et al., 2016). Current treatments for retinal neovascularization have limitations. Although laser photocoagulation helps preserve central vision, it causes peripheral visual loss (Ciulla et al., 2003). In addition, anti-vascular endothelial growth factor (VEGF) drugs effectively treat neovascularization in some, but not all patients and there are safety concerns about the long-term effects including degeneration of normal blood vessels, neural retina and choroid (Arevalo, 2013; Cheung et al., 2012; Fernando Arevalo, 2013; Osaadon et al., 2014; Sato et al., 2012). Therefore, better therapeutic agents are needed for the effective treatment of vision-threatening neovascularization.

As described herein, FGF21 suppresses retinal and choroidal ocular pathologic angiogenesis in three different mouse models of disease. In humans, long-acting FGF21 analog administration increases circulating adiponectin (APN) in a dose-dependent manner (Gaich et al., 2013; Talukdar et al., 2016). In mice, FGF21 administration increases APN production to modulate glucose and lipid metabolism (Holland et al., 2013; Lin et al., 2013). Low circulating APN levels may contribute to the development of neovascular eye diseases in humans (Fu et al., 2016; Fu et al., 2015; Kaarniranta et al., 2012; Mao et al., 2012; Omae et al., 2015). APN administration inhibits retinal and choroidal neovascularization in rodents (Higuchi et al., 2009; Lyzogubov et al., 2012). As described herein, FGF21 inhibits pathological retinal and choroidal angiogenesis in the eye and FGF21 administration improves neovascular eye diseases. As described herein, FGF21 has roles in 1) hypoxia-induced neovascular retinopathy (Smith et al., 1994); 2) retinal neovascularization driven by energy deficiency (Joyal et al., 2016); and 3) laser-induced choroidal neovascularization (Gong et al., 2015).

The compositions and methods of the instant disclosure are expressly contemplated for treatment and/or prevention of at least the following disorders and/or diseases of the eye, either alone or in combination.

Choroidal Neovascularization (CNV)

Choroidal neovascularization (CNV) is the creation of new blood vessels in the choroid layer of the eye. CNV can occur rapidly in individuals with defects in Bruch's membrane, the innermost layer of the choroid. It is also associated with excessive amounts of vascular endothelial growth factor (VEGF). In addition to wet macular degeneration, CNV can also occur frequently with the rare genetic disease pseudoxanthoma elasticum and rarely with the more common optic disc drusen. CNV has also been associated with extreme myopia or malignant myopic degeneration, where in choroidal neovascularization occurs primarily in the presence of cracks within the retinal (specifically) macular tissue known as lacquer cracks. CNV can create a sudden deterioration of central vision, noticeable within a few weeks. Other symptoms which can occur include colour disturbances, and metamorphopsia (distortions in which straight lines appears wavy). Hemorrhaging of the new blood vessels can accelerate the onset of symptoms of CNV. CNV may also include the feeling of pressure behind a subject's eye.

Age-Related Macular Degeneration (AMD)

AMD is a common eye condition and a leading cause of vision loss among people age 50 and older. It causes damage to the macula, a small spot near the center of the retina and the part of the eye needed for sharp, central vision, which lets us see objects that are straight ahead. In some people, AMD advances so slowly that vision loss does not occur for a long time. In others, the disease progresses faster and may lead to a loss of vision in one or both eyes. As AMD progresses, a blurred area near the center of vision is a common symptom. Over time, the blurred area may grow larger or you may develop blank spots in your central vision. Objects also may not appear to be as bright as they used to be.

AMD by itself does not lead to complete blindness, with no ability to see. However, the loss of central vision in AMD can interfere with simple everyday activities, such as the ability to see faces, drive, read, write, or do close work, such as cooking or fixing things around the house.

Macula

The macula is made up of millions of light-sensing cells that provide sharp, central vision. It is the most sensitive part of the retina, which is located at the back of the eye. The retina turns light into electrical signals and then sends these electrical signals through the optic nerve to the brain, where they are translated into the images we see. When the macula is damaged, the center of your field of view may appear blurry, distorted, or dark.

MacTel (Macular Telangiectasia)

Macular telangiectasia is a disease in which the macula is affected, causing a loss of central vision. The macula is a small area in the retina (the light-sensitive tissue lining the back of the eye) that is responsible for central vision, allowing fine details to be seen clearly. Macular telangiectasia develops when there are problems with the tiny blood vessels around the fovea, the center of the macula. There are two types of macular telangiectasia (Type 1 and Type 2), and each affects the blood vessels differently. Macular telangiectasia may occur as a result of a retinal vascular disease or a systemic disease such as diabetes or hypertension, but in many cases, clinical findings reveal no known cause.

One serious complication of macular telangiectasia is the development of abnormal blood vessels under the retina. This is called choroidal neovascularization, and may call for injections of a drug called vascular endothelial growth factor inhibitors (anti-VEGF). Anti-VEGF medication targets a specific chemical in the eye that causes abnormal blood vessels to grow under the retina. That chemical is called vascular endothelial growth factor, or VEGF. Blocking VEGF with medication injections reduces the growth of abnormal blood vessels, slows their leakage, helps to reduce swelling of the retina, and in some cases may improve vision.

Type 1 Macular Telangiectasia

In Type 1 macular telangiectasia, the blood vessels become dilated forming tiny aneurysms, causing swelling and damaging macular cells. The disease almost always occurs in one eye, which differentiates it from Type 2.

Type 2 Macular Telangiectasia

The most common form of macular telangiectasia is Type 2 macular telangiectasia, in which the tiny blood vessels around the fovea leak, become dilated (widen), or both. It is a bilateral disease of unknown cause, which characteristic alterations of macular capillary network and neurosensory atrophy. In some cases, new blood vessels form under the retina and they can also break or leak. Fluid from leaking blood vessels causes the macula to swell or thicken, a condition called macular edema, which affects central vision. Also, scar tissue can sometimes form over the macula and the fovea, causing loss of detail vision. Type 2 affects both eyes but not necessarily with the same severity.

Retinopathy of Prematurity (ROP)

Retinopathy of prematurity (ROP) is a potentially blinding eye disorder that primarily affects premature infants weighing about 2¾ pounds (1250 grams) or less that are born before 31 weeks of gestation (A full-term pregnancy has a gestation of 38-42 weeks). The smaller a baby is at birth, the more likely that baby is to develop ROP. This disorder—which usually develops in both eyes—is one of the most common causes of visual loss in childhood and can lead to lifelong vision impairment and blindness. ROP was first diagnosed in 1942.

With advances in neonatal care, smaller and more premature infants are being saved. These infants are at a much higher risk for ROP. Not all babies who are premature develop ROP. There are approximately 3.9 million infants born in the U.S. each year; of those, about 28,000 weigh 2¾ pounds or less. About 14,000-16,000 of these infants are affected by some degree of ROP. The disease improves and leaves no permanent damage in milder cases of ROP. About 90 percent of all infants with ROP are in the milder category and do not need treatment. However, infants with more severe disease can develop impaired vision or even blindness. About 1,100-1,500 infants annually develop ROP that is severe enough to require medical treatment. About 400-600 infants each year in the US become legally blind from ROP.

ROP is classified in five stages, ranging from mild (stage I) to severe (stage V):

Stage I—Mildly abnormal blood vessel growth. Many children who develop stage I improve with no treatment and eventually develop normal vision. The disease resolves on its own without further progression.

Stage II—Moderately abnormal blood vessel growth. Many children who develop stage II improve with no treatment and eventually develop normal vision. The disease resolves on its own without further progression.

Stage III—Severely abnormal blood vessel growth. The abnormal blood vessels grow toward the center of the eye instead of following their normal growth pattern along the surface of the retina. Some infants who develop stage III improve with no treatment and eventually develop normal vision. However, when infants have a certain degree of Stage III and "plus disease" develops, treatment is considered. "Plus disease" means that the blood vessels of the retina have become enlarged and twisted, indicating a worsening of the disease. Treatment at this point has a good chance of preventing retinal detachment.

Stage IV—Partially detached retina. Traction from the scar produced by bleeding, abnormal vessels pulls the retina away from the wall of the eye.

Stage V—Completely detached retina and the end stage of the disease. If the eye is left alone at this stage, the baby can have severe visual impairment and even blindness.

Most babies who develop ROP have stages I or II. However, in a small number of babies, ROP worsens, sometimes very rapidly. Untreated ROP threatens to destroy vision.

Infants with ROP are considered to be at higher risk for developing certain eye problems later in life, such as retinal detachment, myopia (nearsightedness), strabismus (crossed eyes), amblyopia (lazy eye), and glaucoma. In many cases, these eye problems can be treated or controlled.

ROP occurs when abnormal blood vessels grow and spread throughout the retina, the tissue that lines the back of the eye. These abnormal blood vessels are fragile and can leak, scarring the retina and pulling it out of position. This causes a retinal detachment. Retinal detachment is the main cause of visual impairment and blindness in ROP.

Several complex factors may be responsible for the development of ROP. The eye starts to develop at about 16 weeks of pregnancy, when the blood vessels of the retina begin to form at the optic nerve in the back of the eye. The blood vessels grow gradually toward the edges of the developing retina, supplying oxygen and nutrients. During the last 12 weeks of a pregnancy, the eye develops rapidly. When a baby is born full-term, the retinal blood vessel growth is mostly complete (The retina usually finishes growing a few weeks to a month after birth). But if a baby is born prematurely, before these blood vessels have reached the edges of the retina, normal vessel growth may stop. The edges of the retina—the periphery—may not get enough oxygen and nutrients.

It is believed that the periphery of the retina then sends out signals to other areas of the retina for nourishment. As a result, new abnormal vessels begin to grow. These new blood vessels are fragile and weak and can bleed, leading to retinal scarring. When these scars shrink, they pull on the retina, causing it to detach from the back of the eye.

To date, the most effective proven treatments for ROP are laser therapy or cryotherapy. Laser therapy "burns away" the periphery of the retina, which has no normal blood vessels.

With cryotherapy, physicians use an instrument that generates freezing temperatures to briefly touch spots on the surface of the eye that overlie the periphery of the retina. Both laser treatment and cryotherapy destroy the peripheral areas of the retina, slowing or reversing the abnormal growth of blood vessels. Unfortunately, the treatments also destroy some side vision. This is done to save the most important part of our sight—the sharp, central vision we need for "straight ahead" activities such as reading, sewing, and driving.

Both laser treatments and cryotherapy are performed only on infants with advanced ROP, particularly stage III with "plus disease." Both treatments are considered invasive surgeries on the eye, and doctors don't know the long-term side effects of each.

In the later stages of ROP, other treatment options include:

Scleral buckle. This involves placing a silicone band around the eye and tightening it. This keeps the vitreous gel from pulling on the scar tissue and allows the retina to flatten back down onto the wall of the eye. Infants who have had a sclera buckle need to have the band removed months or years later, since the eye continues to grow; otherwise they will become nearsighted. Sclera buckles are usually performed on infants with stage IV or V.

Vitrectomy. Vitrectomy involves removing the vitreous and replacing it with a saline solution. After the vitreous has been removed, the scar tissue on the retina can be peeled back or cut away, allowing the retina to relax and lay back down against the eye wall. Vitrectomy is performed only at stage V.

While ROP treatment decreases the chances for vision loss, it does not always prevent it. Not all babies respond to ROP treatment, and the disease may get worse. If treatment for ROP does not work, a retinal detachment may develop. Often, only part of the retina detaches (stage IV). When this happens, no further treatments may be needed, since a partial detachment may remain the same or go away without treatment. However, in some instances, physicians may recommend treatment to try to prevent further advancement of the retinal detachment (stage V). If the center of the retina or the entire retina detaches, central vision is threatened, and surgery may be recommended to reattach the retina.

Diabetic Retinopathy

Diabetic retinopathy describes a diabetic eye disease that affects blood vessels in the retina and is both the most common cause of vision loss among people with diabetes and the leading cause of vision impairment and blindness among working-age adults. Chronically high blood sugar from diabetes is associated with damage to the blood vessels in the retina, thereby leading to diabetic retinopathy. This changes the curvature of the lens and results in the development of symptoms of blurred vision. The blurring of distance vision as a result of lens swelling will subside once the blood sugar levels are brought under control. Better control of blood sugar levels in patients with diabetes also slows the onset and progression of diabetic retinopathy. Symptoms of diabetic retinopathy may include seeing spots or floaters in a subject's field of vision, blurred vision, having a dark or empty spot in the center of a subject's vision, and difficulty seeing well at night. Diabetic retinopathy may progress through four stages:

I. Mild nonproliferative retinopathy: small areas of swelling in the retinal blood vessels causing tiny bulges, called microaneurysms to protrude from their walls may occur.

II. Moderate nonproliferative retinopathy: progression of the disease may lead to blood vessels swelling and distorting, therefore affecting their ability to transport blood.

III. Severe nonproliferative retinopathy: more blood vessels become blocked, depriving the blood supply to areas of the retina.

IV. Proliferative diabetic retinopathy: advanced stage of the disease where growth factors secreted by the retina trigger the proliferation of new blood vessels, which grow along the inside surface of the retina and into the fluid that fills the eye. The fragility of the new blood vessels makes them more likely to leak and bleed. Scar tissue can cause retinal detachment (pulling away of the retina from underlying tissue). Retinal detachment can lead to permanent vision loss.

Retinitis Pigmentosa (RP)

Retinitis pigmentosa (RP) is an inherited, degenerative eye disease that causes severe vision impairment due to the progressive degeneration of the rod photoreceptor cells in the retina. This form of retinal dystrophy manifests initial symptoms independent of age—diagnosis occurs from early infancy to late adulthood. Patients in the early stages of RP first notice compromised peripheral and dim light vision due to the decline of the rod photoreceptors. The progressive rod degeneration is later followed by abnormalities in the adjacent retinal pigment epithelium (RPE) and the deterioration of cone photoreceptor cells. As peripheral vision becomes increasingly compromised, patients experience progressive "tunnel vision" and eventual blindness. Afflicted individuals may additionally experience the accumulation of bone spicules in the fundus, defective light-dark adaptations, and nyctalopia (night blindness).

The initial retinal degenerative symptoms of Retinitis Pigmentosa are characterized by decreased night vision (nyctalopia) and the loss of the mid-peripheral visual field. The rod photoreceptor cells, which are responsible for low-light vision and are orientated in the retinal periphery, are the retinal processes affected first during non-syndromic forms of this disease. Visual decline progresses relatively quickly to the far peripheral field, eventually extending into the central visual field as tunnel vision increases. Visual acuity and color vision can become compromised due to accompanying abnormalities in the cone photoreceptor cells, which are responsible for color vision, visual acuity, and sight in the central visual field. The progression of disease symptoms occurs in a symmetrical manner, with both the left and right eyes experiencing symptoms at a similar rate.

A variety of indirect symptoms characterize Retinitis Pigmentosa along with the direct effects of the initial rod photoreceptor degeneration and later cone photoreceptor decline. Phenomena such as photophobia, which describes the event in which light is perceived as an intense glare, and photopsia, the presence of blinking or shimmering lights within the visual field, often manifest during the later stages of RP. Findings related to RP have often been characterized in the fundus of the eye as the Ophthalmic triad. This includes the development of a mottled appearance of the retinal pigment epithelium (RPE) caused by bone spicule formation, a waxy appearance of the optic nerve, and the attenuation of blood vessels in the retina.

A variety of retinal molecular pathway defects have been matched to multiple known RP gene mutations. Mutations in the rhodopsin gene, which is responsible for the majority of autosomal-dominantly inherited RP cases, disrupts the rod-opsin protein essential for translating light into decipherable electrical signals within the phototransduction cascade of the central nervous system. Defects in the activity of this G-protein-coupled receptor are classified into distinct classes that depend on the specific folding abnormality and the resulting molecular pathway defects. The Class I mutant protein's activity is compromised as specific point mutations in the protein-coding amino acid sequence affect the pigment protein's transportation into the outer segment of the eye, where the phototransduction cascade is localized. Additionally, the misfolding of Class II rhodopsin gene mutations disrupts the protein's conjunction with 11-cis-retinal to induce proper chromophore formation. Additional mutants in this pigment-encoding gene affect protein stability, disrupt mRNA integrity post-translationally, and affect the activation rates of transducin and opsin optical proteins. Additionally, animal models suggest that the retinal pigment epithelium fails to phagocytose the outer rod segment discs that have been shed, leading to an accumulation of outer rod segment debris. In mice that are homozygous recessive for retinal degeneration mutation, rod photoreceptors stop developing and undergo degeneration before cellular maturation completes. A defect in cGMP-phosphodiesterase has also been documented; this leads to toxic levels of cGMP.

Fibroblast Growth Factor 21 (FGF21)

Fibroblast growth factor 21 is a protein that in mammals is encoded by the FGF21 gene. The protein encoded by this gene is a member of the fibroblast growth factor (FGF) family and specifically a member of the "endocrine" subfamily which includes FGF23 and FGF15/19. FGF family members possess broad mitogenic and cell survival activities and are involved in a variety of biological processes including embryonic development, cell growth, morphogenesis, tissue repair, tumor growth and invasion. FGFs act through a family of four FGF receptors. Binding is complicated and requires both interaction of the FGF molecule with an FGF receptor and binding to heparin through an heparin binding domain. Endocrine FGFs lack a heparin binding domain and thus can be released into the circulation. FGF21 action through one of the FGF21 receptors thus requires interaction with a co-receptor, designated β-klotho.

FGF21 is specifically induced by HMGCS2 activity. The oxidized form of ketone bodies (acetoacetate) in a cultured medium also induced FGF21, possibly via a SIRT1-dependent mechanism. HMGCS2 activity has also been shown to be increased by deacetylation of lysines 310, 447, and 473 via SIRT3 in the mitochondria. While FGF21 is expressed in numerous tissues, including liver, brown adipose tissue, white adipose tissue and pancreas, circulating levels of FGF21 are derived specifically from the liver in mice. In liver FGF21 expression is regulated by PPARα and levels rise substantially with both fasting and consumption of ketogenic diets. LXR represses FGF21 in humans via an LXR response element located from −37 to −22 bp on the human FGF21 promoter.

FGF21 stimulates glucose uptake in adipocytes. This effect is additive to the activity of insulin. FGF21 treatment of adipocytes is associated with phosphorylation of FRS2, a protein linking FGF receptors to the Ras/MAP kinase pathway. FGF21 injection in ob/ob mice results in an increase in Glut1 in adipose tissue. FGF21 also protects animals from diet-induced obesity when overexpressed in transgenic mice and lowers blood glucose and triglyceride levels when administered to diabetic rodents. Treatment of animals with FGF21 results in increased energy expenditure, fat utilization and lipid excretion.

Serum FGF-21 levels were significantly increased in patients with type 2 diabetes mellitus (T2DM) which may indicate a role in the pathogenesis of T2DM. Elevated levels also correlate with liver fat content in non-alcoholic fatty liver disease and positively correlate with BMI in humans suggesting obesity as a FGF21-resistant state.

FGF21 stimulates phosphorylation of fibroblast growth factor receptor substrate 2 and ERK1/2 in the liver. Acute FGF21 treatment induced hepatic expression of key regulators of gluconeogenesis, lipid metabolism, and ketogenesis including glucose-6-phosphatase, phosphoenol pyruvate carboxykinase, 3-hydroxybutyrate dehydrogenase type 1, and carnitine palmitoyltransferase 1α. In addition, injection of FGF21 was associated with decreased circulating insulin and free fatty acid levels. FGF21 treatment induced mRNA and protein expression of PGC-1α, but in mice PGC-1α expression was not necessary for the effect of FGF21 on glucose metabolism.

In mice FGF21 is strongly induced in liver by prolonged fasting via PPAR-alpha and in turn induces the transcriptional coactivator PGC-1α and stimulates hepatic gluconeogenesis, fatty acid oxidation, and ketogenesis. FGF21 also blocks somatic growth and sensitizes mice to a hibernation-like state of torpor, playing a key role in eliciting and coordinating the adaptive starvation response. FGF21 expression is also induced in white adipose tissue by PPAR-gamma, which may indicate it also regulates metabolism in the fed state.

Activation of AMPK and SIRT1 by FGF21 in adipocytes enhanced mitochondrial oxidative capacity as demonstrated by increases in oxygen consumption, citrate synthase activity, and induction of key metabolic genes. The effects of FGF21 on mitochondrial function require serine/threonine kinase 11 (STK11/LKB1), which activates AMPK. Inhibition of AMPK, SIRT1, and PGC-1α activities attenuated the effects of FGF21 on oxygen consumption and gene expression, indicating that FGF21 regulates mitochondrial activity and enhances oxidative capacity through an LKB1-AMPK-SIRT1-PGC-1α-dependent mechanism in adipocytes, resulting in increased phosphorylation of AMPK, increased cellular NAD+ levels and activation of SIRT1 and deacetylation of SIRT1 targets PGC-1α and histone 3.

Stabilized FGF21

Modifications to FGF21 stabilize the protein and increase the half-life compared to native FGF21 without any loss in efficacy or potency. A stabilized or long-acting FGF21, as described herein, comprises an FGF21 polypeptide conjugated to an antibody scaffold. In certain embodiments, the modified FGF21 is dHis/Ala129Cys, optionally the modified FGF21 is conjugated at Cys 129 to the antibody scaffold. Optionally, two or more FGF21 polypeptide molecules are conjugated to one antibody scaffold—the two or more FGF21 polypeptide molecules can be the same or different from each other. In some embodiments, the antibody scaffold is a humanized IgG1κ monoclonal antibody. In other embodiments, the antibody scaffold is the Fab region of a humanized IgG1κ monoclonal antibody. In some embodiments, the antibody scaffold is a CovX-2000 scaffold. In certain embodiments, the stabilized FGF21 agent is a long acting FGF21 analog, optionally PF-05231023.

In some embodiments, a stabilized FGF21 agent (i.e., long-acting FGF21) possesses a half-life of at least 1.5×, at least 2×, at least 3×, at least 4×, at least 5×, at least 8×, at least 10×, at least 12×, at least 15×, at least 20×, at least 30×, at least 40×, at least 50×, at least 60×, or at least 70× the half-life of a native FGF21 peptide, when assayed for stability under identical conditions. In other embodiments, a stabilized FGF21 agent (i.e., long-acting FGF21) possesses a half-life of at least 0.8 h, at least 1 h, at least 2 h, at least 3 h, at least 4 h, at least 5 h, at least 6 h, at least 7 h, at least 10 h, at least 15 h, at least 20 h, at least 25 h, at least 28 h or at least 30 h in the circulation of a mammal, optionally wherein the mammal is human.

As described herein, the stability or half-life of a modified FGF21 (e.g., long-acting FGF21) composition may be determined by assessing the degree of resistance of such a composition to protease digestion, as compared to native FGF21 compositions, in vitro, in vivo, or both. Optionally, stability may be assessed by collecting blood and/or serum from subjects previously administered a candidate long-acting FGF21 agent and detecting the presence of the long-acting FGF21 agent with anti-FGF21 antibodies in such samples at different time points. Serum samples may be prepared and analyzed using an ELISA-based assay in which long-acting FGF21 compounds are captured in 96 well microtiter plates coated with anti-FGF21 mAb followed by detection with an anti-hIgG-horseradish peroxidase (HRP). Alternatively, the activity of a candidate long-acting FGF21 agent can also be assessed as a proxy for the continued presence of the long-acting FGF21 agent in the sample, at one or more time points post-administration.

Exemplary forms of long-acting FGF21 can be found in the art, for example as described in U.S. Pat. No. 9,163,277, issued Oct. 20, 2015; U.S. Pat. No. 8,722,622, issued May 13, 2014; U.S. Provisional Patent Application 61/644,831, filed May 9, 2012; Huang et al., (2013) *Journal of Pharmacology and Experimental Therapeutics,* 346:270-280; Weng et al., (2015) *PLOS One* 10(3) e0119104:1-18; Thompson et al., (2016) *J. Pharmacokinet Pharmacodyn* 43:411-425; and Talukdar et al., (2016) *Cell Metabolism* 23: 427-440. The disclosure of each of these publications is incorporated herein by reference in its entirety.

Figure 12:
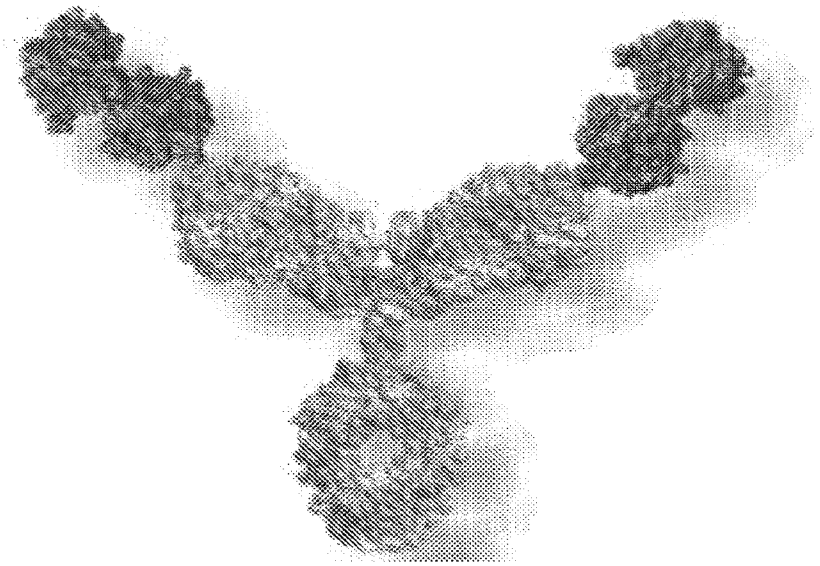
FIG. 12 depicts a polypeptide sequence and structure of an exemplary long-acting FGF21 polypeptide, as depicted in Huang et al., 2013 and described elsewhere herein (SED ID NO.: 1). The sequence of recombinant human ΔHis FGF21 (A129C) and a schematic of the bivalent FGF21 CovX-Body, CVX-343, is shown. The underlined C residue corresponds to position 129, where the FGF21 protein is conjugated to the antibody scaffold.

In certain embodiments, as depicted in FIG. 12, the long-acting FGF21 comprises the following polypeptide sequence (Huang et al., 2013):

```
                                   (SEQ ID NO: 1)
PIPDSSPLLQFGGQVRQRYLYTDDAQQTEAHLEIR

EDGTVGGAADQSPESLLQLKALKPGVIQILGVKTS

RFLCQRPDGALYGSLHFDPEACSFRELLLEDGYNV

YQSEAHGLPLHLPGNKSPHRDPCPRGPARFLPLPG

LPPALPEPPGILAPQPPDVGSSDPLSMVGPSQGR

SPSYAS.
```

For example, a provided long acting FGF21 may be a disclosed FGF21 peptide sequence such as the above, covalently attached to a combining site of an antibody or an antigen binding portion of a scaffold antibody (such as a humanized IgG1k mAb, or e.g., an aldolase catalytic antibody) via a chemical linker (e.g., 3-(2,5-dioxo-2,5-dihydro-1H-pyrrol-1-yl)-N-[2-(2-(3-oxo-3-((4-(3-oxo-3-(2-oxoazetidin-1-yl)propyl)phenyl)amino)propoxy)ethoxy)ethyl] propanamide), wherein for example, the linker is covalently attached to a FGF21 peptide sequence through the thiol group of a cysteine in the FGF21 peptide sequence (e.g., A129C) and the linker is conjugated to the Fab region of the antibody. In some embodiments, two FGF21 peptide sequences (such as disclosed herein) are conjugated to a scaffold antibody (e.g., as depicted in FIG. 12, e.g., a FGF21 homologue (e.g., a modified FGF21)-linker-Ab-linker-FGF21 homologue. In other embodiments a FGF21 peptide sequence and an Exendin4 peptide sequence are conjugated to an antibody.

For example, provided herein is a long acting FGF21 comprising:

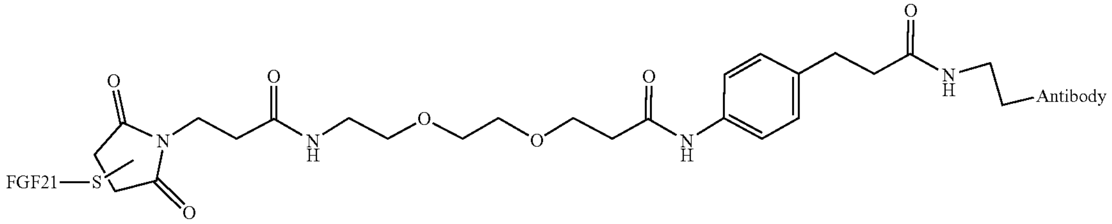

In other embodiments, long acting FGF21 forms may include: pegylated FGF21 (e.g, that includes a FGFR21 with a R131AcF modification, coupled to PEG); modified FGF21 proteins with e.g., a FGF21 L118C, A1343C and/or a S167A modification, which has the effect, for example, to increase stability and/or limit or prevent glycosylation in yeast; and Fc-FGF21 fusion constructs ((e.g, with FGF21 modifications L98R and/or P171G, for example, a fusion protein having an IgG constant domain, a FGF21 protein or modified protein and linker sequence associated with the IgG constant domain FGF21 protein). Contemplated long acting FGF21 forms may include FGF21 mimetics, such as FGFR1b/1c agonist antibodies; mimAB1 agonist antibodies, and FGF1c/β-klothobispecific.

Exemplary wild type FGF21 human and mouse mRNA and protein sequences include:

```
Human FGF21 gene, complete cds
    (GenBank Accession No. DQ847413; SEQ ID NO: 2)
CACAGCACAGCAGGATGACTGCGGGCAGGCCTAGA

TAATACCCAGCCTCCCACAAGAAGCTGGTGGAGCA

GAGTGTTCCCTGACTCCTCCAAGAAAAGGAGATTC

CCTTTCGTGGTCTGCTGAGTAACGGGTGCCTTCCC

AGACACTGGCGTTCCCGCTTGACCAAGGAGCCCTC

AAGAGGCCCTTATGCCGGTGTGACAGAAGGCTCAC

CTCTTGCCTTCTAGGTCACTTCTCACAATGTCCCT

TCAGTACCTGACCCTATACCCACCGGTTGTTTCCT

GGTTATATTAGTTATACAACAAAGAATAAAAGTAA

TAGCTAATGATTAATAATGTTTACACTAATGATTG

ATACTGTCCATGATCATCTCTATATCTAATTTGTA

TGATAACTATTCTTATTCTAACTATTTTCTTTATT
```

-continued

```
ATACTGAAACAGTTTGTGCCTTCAGTCTCTTGCCT

CGGCACCTGGGTAATCCTTCCCCACAGACTGACCC

TCCCATTCAAGATACATCAATGTCAAAGACTCAGG

AGTTTGACTTGATTCCCAGAAGTTTAACCATCATC

TCCCCAGGCTCGGGACTCCCAGCACCCAGACCCTT

CTGCTCACACCCAGCAGTCCAGGCCCCCAGACCCT

CCTCCCTCAGACTTAGGAGTCCAGGCTCCCGGCCC

CTCCTTCCTCAGACCCAGGAGTCCAAGCCCCCTGC

CCCTCCTTCCTCAGACCCAGGAGTCCAGGACCCCA

GCCCCTCCTTCCTCACACCCACGAGTCCAGATCCC

TAGCCCCTACTCCCTCAGACCCAGGAGTCCAGACC

AAAGCTCCCTCCTCCCTCAGACCCAGGAGCCCAAG

TTCCCCAGCCCCTCCTCCCTCAGATCCAGGAGTAC

AGGCCCAGCCCCTCCTCCCTCAGACCCCTCCTCCC

TCAGATCCAGGAGTACAGGCCCAGACCCTCCTCCC

TCAGACCCAGGAGTCCAGGCCCCCCACCCCTCCTC

CCTCAGACCCAGGAGTCCAGAGCCCCAGCCCTCCT

CCCTCAGACACAGAAGGCCTACCCTTGCACCCTTA

GGGGCTCCAGGAAATTAGCCAACCTGTCTTCCCTC

TGGGTGCCCACTCCAGGGCCTGGCTTGGCTGCCAA

CTCCAGTCAGGGACTTTCAGCCACCCCTCCCCCCA

GGTTATTTCAGGAGCACCTGCCTGGGCCTGGGATG

GCTTCTCTGGTGAAAGAAACACCAGGATTGCATCA

GGGAGGAGGAGGCTGGGATGTCCAGGGTCTGAGCA

TCTGAGCAGGGACAGATGAGGTTGAGGTTGGCCCA

CGGCCAGGTGAGAGGCTTCCAAGGCAGGATACTTG

TGTCTCAGATGCGGTCGCTTCTTTCATACAGCAAT

TGCCGCCTTGCTGAGGATCAAGGAACCTCAGTGTC

AGATCACGCCCTCCCCCCAAACTTAGAAATTCAGA

TGGGGCGCAGAAATTTCTCTTGTTCTGCGTGATCT

GCATAGATGGTCCAAGAGGTGGTTTTTCCAGGAGC

CCAGCACCCCTCCTCCCTCCGACTCAGGTGCTTGA

GACCCCAGATCCTTCTCTCTGAGACTCAGGAATGT

GGGCCCCCAGCCCCTTTCACCTGGGTCCCAGCTAA

CCCGATCCTCCCCTCCCTCATCCCCTAGACCCAGG

AGTCTGGCCCTCCATTGAAAGGACCCCAGGTTACA

TCATCCATTCAGGCTGCCCTTGCCACGATGGAATT

CTGTAGCTCCTGCCAAATGGGTCAAATATCATGGT

TCAGGCGCAGGGAGGGTGATTGGGCGGGCCTGTCT

GGGTATAAATTCTGGAGCTTCTGCATCTATCCCAA
```

-continued

```
AAAACAAGGGTGTTCTGTCAGCTGAGGATCCAGCC

GAAAGAGGAGCCAGGCACTCAGGCCACCTGAGTCT

ACTCACCTGGACAACTGGAATCTGGCACCAATTCT

AAACCACTCAGCTTCTCCGAGCTCACACCCCGGAG

ATCACCTGAGGACCCGAGCCATTGATGGACTCGGA

CGAGACCGGGTTCGAGCACTCAGGGCTGTGGGTTT

CTGTGCTGGCTGGTCTTCTGCTGGGAGCCTGCCAG

GCACACCCCATCCCTGACTCCAGTCCTCTCCTGCA

ATTCGGGGGCCAAGTCCGGCAGCGGTACCTCTACA

CAGATGATGCCCAGCAGACAGAAGCCCACCTGGAG

ATCAGGGAGGATGGGACGGTGGGGGGCGCTGCTGA

CCAGAGCCCCGAAAGTGAGTGTGGGCCAGAGCCTG

GGTCTGAGGGAGGAGGGGCTGTGGGTCTGGATTCC

TGGGTCTGAGGGAGGAGGGGCTGGGGGCCTTGGCC

CCTGGGTCTGAGGGAGGAGGGGCTGGGGATCTGGA

CTCCTGGGTCTGAGGGAGGAGGGGCTGGGGATCTG

GGCCCCTGGGTCTGAGGGAGGAGGGGCTGGGTCTG

GACCCCTGGGTCTGAGGGAGGAGGGGCTGGGGGTC

TGGACTCTTGGGTTTGAAGAAGGAAGGGCTGGGGT

CCTGGACTCTTGGGTCTGAGTTGGGAGGGGGCTTT

GGCTTGGGCTTCTCCTGGGTCTGAGGGAGGAGGTA

GGCTGTGGGCTTGGACTCCCAGGGCTGGGACAGAG

CCGGATGGTGGGACAGAGTCGGGTGGTGGGACAGT

CCCGGGTGGGAGAGGTCCTCGAACCACCTTATCGC

TTTCACCCCTTAGGTCTCCTGCAGCTGAAAGCCTT

GAAGCCGGGAGTTATTCAAATCTTGGGAGTCAAGA

CATCCAGGTTCCTGTGCCAGCGGCCAGATGGGGCC

CTGTATGGATCGGTGAGTTTCCAGGACCCTCCTCA

CCACCCACCATGCTCCTCCTATATGTCGCCCTCAC

AGCCTGGGGTGCCTTGTCTTGCTCATCCCCCCCGG

AGCCAGACTTGATTCTATTTGCTCTGCACGCCCCC

AGCTGCAACATTTGGAGGTTGAAGTTGTCATCAGT

GTTTGCAAGATGAGGAAACTGAGGCCCAGGCCGGG

GCGCCAGTGACCTCAATCATGTGATGTGTGGATGC

TGGAGCGGCCTGAGGCTCAGGTTATTGGGAGTCTC

GTGATTCAGTAACCCCTGCTCCTGCCCACACGGCC

CCTGTGTGCACGGCTCATGCTGGGCACAGGGACAC

TCGGGGAAGCCATGGCCAGTAAAGTGACCAGGACC

TTGAGTGCTAGGGAGACACCCCGCCTGGCCTGAGA

GAGCACTGATGGCTCCGAGGGCTGGAATGTTCTCT

GTGAAGTCTGAACTGGGAGGCAGGTCCCTGCAGGA
```

-continued

GAGCCCTGGGGTAAAAAACAAAACCTGCCTTGCTG
TTTTGTTTCCTAGAGGAGGGGCTGGGGGCCTGGAC
TCCTGGGTCTGAGGGAGGAGGGGCTGGGGGCCTGG
ACCCCTGGGTCTGAGGGAGGAGGGGCTGGGGGCCT
GGAACCCCGGGTCTGAGGGAGGAGAGGCTGGGGCC
TGGAACCCCGGGTCTGAGGGAGGAGAGGCTGGGGC
CTGGAACCCCGGGTCTGAGGGAGGAGGCGCTGGGG
GCCTGGACTCCTGGGTCGGATGGAGGAGAAACTAG
GGTCTGGACCCCTGGGTCTGAGGGAGGAGGCGCTG
GGGGCCTGGACCCCTGGGTCTGAGGGAGGCAGGGC
TGGGGCCTGGATCCTGGGTCTTACATCAGGAAAAC
AGAGGAACCCTGTCTCTGATCCTGTTTTTGTCCCC
TAGCTCCACTTTGACCCTGAGGCCTGCAGCTTCCG
GGAGCTGCTTCTTGAGGACGGATACAATGTTTACC
AGTCCGAAGCCCACGGCCTCCCGCTGCACCTGCCA
GGGAACAAGTCCCCACACCGGGACCCTGCACCCCG
AGGACCAGCTCGCTTCCTGCCACTACCAGGCCTGC
CCCCCGCACCCCCGGAGCCACCCGGAATCCTGGCC
CCCCAGCCCCCCGATGTGGGCTCCTCGGACCCTCT
GAGCATGGTGGGACCTTCCCAGGGCCGAAGCCCCA
GCTACGCTTCCTGAAGCCAGAGGCTGTTTACTATG
ACATCTCCTCTTTATTTATTAGGTTATTTATCTTA
TTTATTTTTTTATTTTTCTTACTTGAGATAATAAA
GAGTTCCAGAGGAGGATAAGAATGAGCATGTGTGA
GTGTCTGAGGGAAGACATGGCAGCTGTTTTGTCTC
CCTTGGCCCGGACAATCCCCTCTACACCTCCCCTC
ACGTGGTCCGAGGGTCCTGGCTTCCCACTGGGCCT
CACTTTTTTCTTTTCTTTTCTTTTTTTTTTTTTGA
GACGGAGTCTCGCTCTGTCACCCAGGCTGGAGTGC
AGTGGCGCGATCTTGGCTCACTCCAACCTCCGCCT
CCCAGGTTCAAGCAATTCTCCTGCCTCAGCCACCC
GAGTAGCTGTGATTACAGGCGTGCGCCACCACACC
CAGCTAATTTTGTAATTTTAGTAGAGACAGGGTTT
CGCCATGTTGGCCAGGATGCTCTCCATCTCTTGAC
TTCATGACCTGCCTGCCTTGGCCTCCCAAAGTGCT
GGGATTACAGGCTTGAGTCACTGTGCCCAGCCCAG
CCTCACTTTTCTACTCTGCTAAAGTGTCCCCAGGG
ACTGTGGACTATCCCTGCTCTCTGAAAGGACAAGA
CTGGCCGGGAGTGGTGGCTTACGCCTGTAATCCCA
GCACTTTGGGAGGCCGAGGCAGGTGGATCACGAGG

-continued

TCAGGAGATTGAGACTATCCTGGCTAATACGATGA
AACCCCGTCTCTACTAAAAATACAAAAACAAAATT
AGCTGGGCGTGGTGGCGGGCGCCTGTAGTCCCAGC
TACTCCGGAGGCTGAGGCAGAATGGCGTGAATGCG
GGAGGCGGAGCTTGCAGTGAGCCGAGATCGCGCCA
CTGCACTCCAGCCCAGGCCACAGAGCGAGATTCCA
TCTCAAAAAAATAAATAAATAAATAAATAAATAAA
TAAATATAAAAATAAAATGAAAGAGCAGGACTTCT
TTCTACAACCCCTCAACTTGTGTGAGCGTTGTGTA
ACTATTTCATAGAGCTACCTCAATAACAGGGGAGC
TTTTACGAGGTGACACAGCACACTCACATCCTCAT
GGGAGATGTAGTTTTCTGGCATCATTTAGCAGCAG
GAATGAGATCTGTTGGGCCTCAAATCTGGGACAAG
GACTCCTGGGTCCTGGAGTAGGTTTGGGGCTAGTG
TAACACCCAAGTTCTGGGGAATCAGTGGGCTGGAC
ATCTGGACACCTGGATCACAGGAGAACTGGGGACT
GCAGACTTAGGCATCCTGGTCTGAGAAAAAAGGGG
CTGGAGGGTGGGAGTTTGGGTTCTCAGGAAAAGGA
GCTGAAACCTGGAATTCTTCCATCTGGGTCCTTAT
GAAC mRNA:
Human FGF21 mRNA, complete cds
(GenBank Accession NM_019113; SEQ ID NO: 3)

GAGGCTTCCAAGGCAGGATACTTGTGTCTCAGATG
CGGTCGCTTCTTTCATACAGCAATTGCCGCCTTGC
TGAGGATCAAGGAACCTCAGTGTCAGATCACGCCC
TCCCCCCAAACTTAGAAATTCAGATGGGGCGCAGA
AATTTCTCTTGTTCTGCGTGATCTGCATAGATGGT
CCAAGAGGTGGTTTTTCCAGGAGCCCAGCACCCCT
CCTCCCTCCGACTCAGACCCAGGAGTCTGGCCCTC
CATTGAAAGGACCCCAGGTTACATCATCCATTCAG
GCTGCCCTTGCCACGATGGAATTCTGTAGCTCCTG
CCAAATGGGTCAAATATCATGGTTCAGGCGCAGGG
AGGGTGATTGGGCGGGCCTGTCTGGGTATAAATTC
TGGAGCTTCTGCATCTATCCCAAAAAACAAGGGTG
TTCTGTCAGCTGAGGATCCAGCCGAAAGAGGAGCC
AGGCACTCAGGCCACCTGAGTCTACTCACCTGGAC
AACTGGAATCTGGCACCAATTCTAAACCACTCAGC
TTCTCCGAGCTCACACCCCGGAGATCACCTGAGGA
CCCGAGCCATTGATGGACTCGGACGAGACCGGGTT
CGAGCACTCAGGACTGTGGGTTTCTGTGCTGGCTG
GTCTTCTGCTGGGAGCCTGCCAGGCACACCCCATC

-continued

```
CCTGACTCCAGTCCTCTCCTGCAATTCGGGGGCCA

AGTCCGGCAGCGGTACCTCTACACAGATGATGCCC

AGCAGACAGAAGCCCACCTGGAGATCAGGGAGGAT

GGGACGGTGGGGGGCGCTGCTGACCAGAGCCCCGA

AAGTCTCCTGCAGCTGAAAGCCTTGAAGCCGGGAG

TTATTCAAATCTTGGGAGTCAAGACATCCAGGTTC

CTGTGCCAGCGGCCAGATGGGGCCCTGTATGGATC

GCTCCACTTTGACCCTGAGGCCTGCAGCTTCCGGG

AGCTGCTTCTTGAGGACGGATACAATGTTTACCAG

TCCGAAGCCCACGGCCTCCCGCTGCACCTGCCAGG

GAACAAGTCCCCACACCGGGACCCTGCACCCCGAG

GACCAGCTCGCTTCCTGCCACTACCAGGCCTGCCC

CCCGCACTCCCGGAGCCACCCGGAATCCTGGCCCC

CCAGCCCCCCGATGTGGGCTCCTCGGACCCTCTGA

GCATGGTGGGACCTTCCCAGGGCCGAAGCCCCACT

ACGCTTCCTGAAGCCAGAGGCTGTTTACTATGACA

TCTCCTCTTTATTTATTAGGTTATTTATCTTATTT

ATTTTTTTATTTTTCTTACTTGAGATAATAAAGAG

TTCCAGAGGAGGATAAAAAAAAAAAAAAAAAAAAAA
mRNA:
```

Mus musculus FGF21, mRNA
(GenBank Accession No. NM_020013; SEQ ID NO: 4)

```
AGACAGCCTTAGTGTCTTCTCAGCTGGGGATTCAA

CACAGGAGAAACAGCCATTCACTTTGCCTGAGCCC

CAGTCTGAACCTGACCCATCCCTGCTGGGCACCGG

AGTCAGAACACAATTCCAGCTGCCTTGGCTCCTCA

GCCGCTCGCTTGCCAGGGGCTCTCCCGAACGGAGC

GCAGCCCTGATGGAATGGATGAGATCTAGAGTTGG

GACCCTGGGACTGTGGGTCCGACTGCTGCTGGCTG

TCTTCCTGCTGGGGGTCTACCAAGCATACCCCATC

CCTGACTCCAGCCCCCTCCTCCAGTTTGGGGGTCA

AGTCCGGCAGAGGTACCTCTACACAGATGACGACC

AAGACACTGAAGCCCACCTGGAGATCAGGGAGGAT

GGAACAGTGGTAGGCGCAGCACACCGCAGTCCAGA

AAGTCTCCTGGAGCTCAAAGCCTTGAAGCCAGGGG

TCATTCAAATCCTGGGTGTCAAAGCCTCTAGGTTT

CTTTGCCAACAGCCAGATGGAGCTCTCTATGGATC

GCCTCACTTTGATCCTGAGGCCTGCAGCTTCAGAG

AACTGCTGCTGGAGGACGGTTACAATGTGTACCAG

TCTGAAGCCCATGGCCTGCCCCTGCGTCTGCCTCA

GAAGGACTCCCCAAACCAGGATGCAACATCCTGGG

GACCTGTGCGCTTCCTGCCCATGCCAGGCCTGCTC
```

-continued

```
CACGAGCCCCAAGACCAAGCAGGATTCCTGCCCCC

AGAGCCCCCAGATGTGGGCTCCTCTGACCCCCTGA

GCATGGTAGAGCCTTTACAGGGCCGAAGCCCCAGC

TATGCGTCCTGACTCTTCCTGAATCTAGGGCTGTT

TCTTTTTGGGTTTCCACTTATTTATTACGGGTATT

TATCTTATTTATTTATTTTAGTTTTTTTTTCTTAC

TTGGAATAATAAAGAGTCTGAAAGAAAAATGTGTG

TT
```

Mus musculus FGF21 protein (AAH49592)
(SEQ ID NO: 5)

```
MEWMRSRVGTLGLWVRLLLAVFLLGVYQAYPIPDS

SPLLQFGGQVRQRYLYTDDDQDTEAHLEIREDGTV

VGAAHRSPESLLELKALKPGVIQILGVKASRFLCQ

QPDGALYGSPHFDPEACSFRELLLEDGYNVYQSEA

HGLPLRLPQKDSPNQDATSWGPVRFLPMPGLLHEP

QDQAGFLPPEPPDVGSSDPLSMVEPLQGRSPSYAS
```

Human FGF21 protein
(GenBank accession AAQ89444)
(SEQ ID NO: 6)

```
MDSDETGFEHSGLWVSVLAGLLGACQAHPIPDSSP

LLQFGGQVRQRYLYTDDAQQTEAHLEIREDGTVGG

AADQSPESLLQLKALKPGVIQILGVKTSRFLCQRP

DGALYGSLHFDPEACSFRELLLEDGYNVYQSEAHG

LPLHLPGNKSPHRDPAPRGPARFLPLPGLPPALPE

PPGILAPQPPDVGSSDPLSMVGPSQGRSPSYAS
```

Beta Klotho

Beta klotho contributes to the transcriptional repression of cholesterol 7-alpha-hydroxylase (CYP7A1), the rate-limiting enzyme in bile acid synthesis. Beta klotho increases the ability of FGFR1 and FGFR4 to bind FGF21. Beta klotho acts as a co-receptor for FGF21. The fibroblast growth factor (FGF) 19 subfamily of ligands, FGF19, FGF21, and FGF23, function as hormones that regulate bile acid, fatty acid, glucose, and phosphate metabolism in target organs through activating FGF receptors (FGFR1-4). Klotho and βKlotho, homologous single-pass transmembrane proteins that bind to FGFRs, are required for metabolic activity of FGF23 and FGF21, respectively. Like FGF21, FGF19 also requires βKlotho. Both FGF19 and FGF21 can signal through FGFR1-3 bound by βKlotho and increase glucose uptake in adipocytes expressing FGFR1. Additionally, both FGF19 and FGF21 bind to the βKlotho-FGFR4 complex; however, only FGF19 signals efficiently through FGFR4. Accordingly, FGF19, but not FGF21, activates FGF signaling in hepatocytes that primarily express FGFR4 and reduces transcription of CYP7A1 that encodes the rate-limiting enzyme for bile acid synthesis. The expression of βKlotho, in combination with particular FGFR isoforms, determines the tissue-specific metabolic activities of FGF19 and FGF21.

Exemplary Beta Klotho human and mouse mRNA and protein sequences include:

Human Beta Klotho gene, Cyp7al
gene, linear DNA
(GenBank Accession No. DD362478)
(SEQ ID NO: 7)

```
ACCCTGGGCCTGGCCCAAGAAACTATACATTCCTC          5

CTGGGAATCTGGGGCTGTGATGGGAGGGGTTGCCA

TGAAGACTTCTGACATGCCCTGGAGACATTTTCCC

CATGGTCTTGGGGATTAACATTCAGCTCCTTGTTA         10

CTTATGCAAATTTCTGCAGCTGGCTTGAATTTCTC

CTCAGAAAATGAGATTTTCTTTTCTATCGCATTGT

CAGGCTGCAAATTTTCCAAACTTTTGTGCTCTGCT         15

TCCCTTATAAAACTGAAGGCCTGGCCAGGTGTGGT

GGCTCACGCCTGTAATCCCAGCACTTTGGGGAGCT

GAGAC
                                            20
GGGCGAATCACGAGGTCAGGAGTTCGAGACCAGCC

TGGCCAACATGGTGAAACCCTGTCTCTACTAAAAA

TACAAAAAGTTAGCTGGGCATAGTCATGGGTGCCT
                                            25
TTAATCCCAGCTACTTGGGAGACTGAGGCAGGAGA

ATCGTTTGAATCCAGGAGGCGGAGGTTGCAGTGAG

TCGAGATCACACCACTGCACTCCAGCCCTGGTAAC
                                            30
ATAGTAAGACTCTGTCTCAAAAAAAAAAAAAAAAA

AACAAAACTGAATGCCTTTAACAACACCCAAGTTG

CTTCTTGAATGCTTTGCTGCTTAGAAATTTCTTCT
                                            35
GCCAGATACCCTAAATCATCTCTCTTAGGTTCCAA

GTTCCACAAATCTCTAGGGCAGGGACAAAACGCTG

CCAGTCTCTTTACTAAAACATAACAAGAGTCACCC
                                            40
TTGCTCTAGTTCCCAAAAAGTTCCTCATCTCCATC

TGAAACCACCCCCGCCTAGATTTCGTTGTCCATAT

CATTATCAGCATTTTGGTCAAAGTCATTCAACAGG

CCTCTAGGGAGTTCCAAACTTGCTCACATTCTCCT     45

GTCTTCTTCTGAGCCCTCCAAACTGTTCCAATCCC

TACCTGTTACCCAGTTCCAAAGTCGCTTCCACATT

TTTGGTTATCTTTTCAGCCGTGCCCCACTCTACTG     50

GTACCAGTTTACTGTATTAGTCGATTTTCATGCTG

CTGATAAAGACATACCTGAAACTGGACAATTTACA

AAAGAAAGAGGTTTATTGGACTTACAATTCTACAT     55

CACTTGGGAGGCCTCACAATCATGATGGAAGGAGA

AAGGCACATCTCACATGGCAGCAGACAAGAAAAGA

GCTTGTGCAGGGAAACTCCTCTTTTTAAAACCATC
                                            60
AGATCTCATGAAATTTATTCATTATCATGACAATA

GCACAGGAAAGAACTGCACCCATAATTCAGTCACC

TCCTACCAGGTTCCTCCCACAACACGTGAGAATTC
                                            65
AAGATGAGATTTGGATGGGGACACAGCCAAACCAT
```

```
GTCACACTACCATGCCTGACTTCCTTTCCATTTTT

GTATATTTGCTTGTTCTTCATTTGCCCGAGAAGTA

ACTCTAAAGGGCTGTATTATTTGGATATTAGATTG

GCATTTTATCTGACTGGGATATCTTGCTGTGATTG

TCCATGTATAAGATCAGCTTTTCTATAAACCATAT

TTTTAAAAAGATATATTAATTTTTTAAAAATCCAC

CTGTCTAAATAAATGCACAAAGCCCCCCAAAAACC

TAGATTCTAAGAAAAATCTATGTACTGCCATACAA

TGATTGATATTAATATTTATGGTGATAAATTACAC

ACAAAAAATGTGTGATCTCTGTTTAAACAGGCAAA

AACAAAAAACACATGAAATAAATCTATGGCATCTA

TAGCCAAAACTGGAAACAACCCACATATCCATCAA

TAGGAAATCAGTTAAATAAATTATAGTACATTTAT

CCAATGGAAGATTAAGCACATATTCAATATAATTA

TTTATACACACATATAGATACACACATGTATAAAT

ATAGAGAATACTGTGGGTGTATGTGTGTGTGTGTT

TATATACATATATATACACACACAGTACTGTTGCC

TACCTTCTTTTGTCTTAATTCTGTGAACTCTCATT

CACTCTGCTTCAGTAGGATACATCCTTCTTTTTGG

TTCTTAGACTCACCAAGTTGATCCTTGACTCAAGA

CATTGCATTTGCTGCTTCCTCTTCCTGGAATATCC

TTCCTTCTGATATTCACATGAGTAGTCTCTTCTTG

TCATTCAGATCTCAAATGTCACAATTTCAGAGAGC

CCATCTCTGATCATCATATCTAAAGTTGTCCTCAT

TCCCCCATAGCTTTCTATACCATGTTTTATTTTTT

TCATAACATGTATTTTATTACTCCTTTCTCCATTG

GAATAGAATCTCCATTAGATTAGGAAATCTGCCTA

TCTTATTAATGCCTGCAACTGGAATACTTTTGAAG

AGTTCTTGGCACGTAATAAATACTCAACTAATATT

TTTGTGTACACAGAAATAAAGTTTGGAAGAACAGA

TGCCAAATTGTTACTAGTGGTTACTTCTGAGTAAA

GGAGTAGCATGGTAGGTAAATTATTAATAGATGTT

CACTTTCCACCAAGATATGTTTTAGTTAGTCTTAA

CTTACTTGAAATGAAATTTATTACTTTAATAATTA

GAAACATTGATAAACATTTTAGTCACAAGAATGAT

AGATAAAATTTTGATGCTTCCAATAAGTTATATTT

ATCTAGAGGATGCACTTATGTAGAATACTCTCTTG

AGGATGTTAGGTGAGTAACATGTTACTATATGTAG

TAAAATATCTATGATTTTATAAAAGCACTGAAACA

TGAAGCAGCAGAAACGTTTTTCCCAGTTCTCTTTC
```

-continued

CTCTGAACTTGATCACCGTCTCTCTGGCAAAGCAC

CTAAATTAATTCTTCTTTAAAAGTTAACAAGACCA

AATTATAAGCTTGATGAATAACTCATTCTTATCTT

TCTTTAAATGATTATAGTTTATGTATTTATTAGCT

ATGCCCATCTTAAACAGGTTTATTTGTTCTTTTTA

CACATACCAAACTCTTAATATTAGCTGTTGTCCCC

AGGTCCGAATGTTAAGTCAACATATATTTGAGAGA

ACTTCAACTTATCAAGTATTGCAGGTCTCTGATTG

CTTTGGAACCACTTCTGATACCTGTGGACTTAGTT

CAAGGCCAGTTACTACCACTTTTTTTTTTCTAATA

GAATGAACAAATGGCTAATTGTTTGCTTTGTCAAC

CAAGCTCAAGTTAATGGATCTGGATACTATGTATA

TAAAAAGCCTAGCTTGAGTCTCTTTTCAGTGGCAT

CCTTCCCTTTCTAATCAGAGATTTTCTTCCTCAGA

GATTTTGGCCTAGATTTGCAAA

*Homo sapiens*, klotho beta (KLB) mRNA (GenBank Accession No. NM_175737)

(SEQ ID NO: 8)

ATCCTCAGTCTCCCAGTTCAAGCTAATCATTGACA

GAGCTTTACAATCACAAGCTTTTACTGAAGCTTTG

ATAAGACAGTCCAGCAGTTGGTGGCAAATGAAGCC

AGGCTGTGCGGCAGGATCTCCAGGGAATGAATGGA

TTTTCTTCAGCACTGATGAAATAACCACACGCTAT

AGGAATACAATGTCCAACGGGGGATTGCAAAGATC

TGTCATCCTGTCAGCACTTATTCTGCTACGAGCTG

TTACTGGATTCTCTGGAGATGGAAGAGCTATATGG

TCTAAAAATCCTAATTTTACTCCGGTAAATGAAAG

TCAGCTGTTTCTCTATGACACTTTCCCTAAAAACT

TTTTCTGGGGTATTGGGACTGGAGCATTGCAAGTG

GAAGGGAGTTGGAAGAAGGATGGAAAAGGACCTTC

TATATGGGATCATTTCATCCACACACACCTTAAAA

ATGTCAGCAGCACGAATGGTTCCAGTGACAGTTAT

ATTTTTCTGGAAAAAGACTTATCAGCCCTGGATTT

TATAGGAGTTTCTTTTTATCAATTTTCAATTTCCT

GGCCAAGGCTTTTCCCCGATGGAATAGTAACAGTT

GCCAACGCAAAAGGTCTGCAGTACTACAGTACTCT

TCTGGACGCTCTAGTGCTTAGAAACATTGAACCTA

TAGTTACTTTATACCACTGGGATTTGCCTTTGGCA

CTACAAGAAAAATATGGGGGGTGGAAAAATGATAC

CATAATAGATATCTTCAATGACTATGCCACATACT

GTTTCCAGATGTTTGGGGACCGTGTCAAATATTGG

ATTACAATTCACAACCCATATCTAGTGGCTTGGCA

-continued

TGGGTATGGGACAGGTATGCATGCCCCTGGAGAGA

AGGGAAATTTAGCAGCTGTCTACACTGTGGGACAC

AACTTGATCAAGGCTCACTCGAAAGTTTGGCATAA

CTACAACACACATTTCCGCCCACATCAGAAGGGTT

GGTTATCGATCACGTTGGGATCTCATTGGATCGAG

CCAAACCGGTCGGAAAACACGATGGATATATTCAA

ATGTCAACAATCCATGGTTTCTGTGCTTGGATGGT

TTGCCAACCCTATCCATGGGGATGGCGACTATCCA

GAGGGGATGAGAAAGAAGTTGTTCTCCGTTCTACC

CATTTTCTCTGAAGCAGAGAAGCATGAGATGAGAG

GCACAGCTGATTTCTTTGCCTTTTCTTTTGGACCC

AACAACTTCAAGCCCCTAAACACCATGGCTAAAAT

GGGACAAAATGTTTCACTTAATTTAAGAGAAGCGC

TGAACTGGATTAAACTGGAATACAACAACCCTCGA

ATCTTGATTGCTGAGAATGGCTGGTTCACAGACAG

TCGTGTGAAAACAGAAGACACCACGGCCATCTACA

TGATGAAGAATTTCCTCAGCCAGGTGCTTCAAGCA

ATAAGGTTAGATGAAATACGAGTGTTTGGTTATAC

TGCCTGGTCTCTCCTGGATGGCTTTGAATGGCAGG

ATGCTTACACCATCCGCCGAGGATTATTTTATGTG

GATTTTAACAGTAAACAGAAAGAGCGGAAACCTAA

GTCTTCAGCACACTACTACAAACAGATCATACGAG

AAAATGGTTTTTCTTTAAAAGAGTCCACGCCAGAT

GTGCAGGGCCAGTTTCCCTGTGACTTCTCCTGGGG

TGTCACTGAATCTGTTCTTAAGCCCGAGTCTGTGG

CTTCGTCCCCACAGTTCAGCGATCCTCATCTGTAC

GTGTGGAACGCCACTGGCAACAGACTGTTGCACCG

AGTGGAAGGGGTGAGGCTGAAAACACGACCCGCTC

AATGCACAGATTTTGTAAACATCAAAAAACAACTT

GAGATGTTGGCAAGAATGAAAGTCACCCACTACCG

GTTTGCTCTGGATTGGGCCTCGGTCCTTCCCACTG

GCAACCTGTCCGCGGTGAACCGACAGGCCCTGAGG

TACTACAGGTGCGTGGTCAGTGAGGGGCTGAAGCT

TGGCATCTCCGCGATGGTCACCCTGTATTATCCGA

CCCACGCCCACCTAGGCCTCCCCGAGCCTCTGTTG

CATGCCGACGGGTGGCTGAACCCATCGACGGCCGA

GGCCTTCCAGGCCTACGCTGGGCTGTGCTTCCAGG

AGCTGGGGGACCTGGTGAAGCTCTGGATCACCATC

AACGAGCCTAACCGGCTAAGTGACATCTACAACCG

CTCTGGCAACGACACCTACGGGGCGGCGCACAACC

TGCTGGTGGCCCACGCCCTGGCCTGGCGCCTCTAC

-continued

GACCGGCAGTTCAGGCCCTCACAGCGCGGGGCCGT
GTCGCTGTCGCTGCACGCGGACTGGGCGGAACCCG
CCAACCCCTATGCTGACTCGCACTGGAGGGCGGCC
GAGCGCTTCCTGCAGTTCGAGATCGCCTGGTTCGC
CGAGCCGCTCTTCAAGACCGGGGACTACCCCGCGG
CCATGAGGGAATACATTGCCTCCAAGCACCGACGG
GGGCTTTCCAGCTCGGCCCTGCCGCGCCTCACCGA
GGCCGAAAGGAGGCTGCTCAAGGGCACGGTCGACT
TCTGCGCGCTCAACCACTTCACCACTAGGTTCGTG
ATGCACGAGCAGCTGGCCGGCAGCCGCTACGACTC
GGACAGGGACATCCAGTTTCTGCAGGACATCACCC
GCCTGAGCTCCCCCACGCGCCTGGCTGTGATTCCC
TGGGGGGTGCGCAAGCTGCTGCGGTGGGTCCGGAG
GAACTACGGCGACATGGACATTTACATCACCGCCA
GTGGCATCGACGACCAGGCTCTGGAGGATGACCGG
CTCCGGAAGTACTACCTAGGGAAGTACCTTCAGGA
GGTGCTGAAAGCATACCTGATTGATAAAGTCAGAA
TCAAAGGCTATTATGCATTCAAACTGGCTGAAGAG
AAATCTAAACCCAGATTTGGATTCTTCACATCTGA
TTTTAAAGCTAAATCCTCAATACAATTTTACAACA
AAGTGATCAGCAGCAGGGGCTTCCCTTTTGAGAAC
AGTAGTTCTAGATGCAGTCAGACCCAAGAAAATAC
AGAGTGCACTGTCTGCTTATTCCTTGTGCAGAAGA
AACCACTGATATTCCTGGGTTGTTGCTTCTTCTCC
ACCCTGGTTCTACTCTTATCAATTGCCATTTTTCA
AAGGCAGAAGAGAAGAAAGTTTTGGAAAGCAAAAA
ACTTACAACACATACCATTAAAGAAAGGCAAGAGA
GTTGTTAGCTAAACTGATCTGTCTGCATGATAGAC
AGTTTAAAAATTCATCCCAGTTCCATATGCTGGTA
ACTTACAGGAGATATACCTGTATTATAGAAAGACA
ATCTGAGATACAGCTGTAACCAAGGTGATGACAAT
TGTCTCTGCTGTGTGGTTCAAAGAACATTCCCTTA
GGTGTTGACATCAGTGAACTCAGTTCTTGGATGTA
AACATAAAGGCTTCATCCTGACAGTAAGCTATGAG
GATTACATGCTACATTGCTTCTTAAAGTTTCATCA
ACTGTATTCCATCATTCTGCTTTAGCTTTCATCTC
TACCAATAGCTACTTGTGGTACAATAAATTATTTT
TAAGAAGTAAAACTCTGGGGCTGGACGCTGTGGCT
CACACCTGTAATCTCAGCACTTTGGGAGGCCGAGG
CGGGGAGATCACCTGAGGTGAGGAGTTCGAGACCA

-continued

GCCTGGCCAACATGGTGAAACCATGTCTCTACTAA
AAATACAAAAAATTAGCCAGGCGTGGTGACAGTGG
CACCTGTAATCCCAGCTACTTGGGAGGCTGAGGCA
GAAGTTTGAACCCAGGAAACAGGTTACAGTAGGCC
AAAATTGCGCCACTGCACTCCAGCCTAGGCGACAA
CAGCAAGACTGTGTCCAAAAAAAAAAAAAAAAGCA
AAAGCAAAACTTTGTTTTGTTAGACTCTACAGCAG
AGATTTAACACCCTTCTTTAAACTGGGTAGTCAGT
GATAGATAATATATATTCTGTCACTTCTAATAAGG
TGCCTTCTCCTTTAGGTCAGGGTGGTTCTAAAATG
GAAAGAAAACACAATAGGGTAAGTAGTGCTTGTCT
AAGCCAGTTACAACACAGACTCTTAAAGAGGATCA
AGCCCTTCATTTTTCTAACAACAAAAAATCACCTA
TAGAATATCTAATTTGTGATCTTTTACTAGATCTG
ATTTTTTAAAATAATGTAATTTCCGGCCAGGCACG
GTGGCACCGCCTGTAATCCCAGCACTTTGGGAGGC
CAAGGCAGGTGGATCACCTGAGGTTAGGAGTTCGA
GACTAGCCTGGCCAACATGGCAAAACCCCATCTCT
ACTAAAAATACAAAAGTTAGCCGGGCATGGTGGTG
GGCACCTGTAATCCCAGCTACTCAGGAGGCCGAGG
CAGGAGAATCGCTTGAACCCGAGAGGCAGAGGTTG
CAATGAGCCAAGATCGTGCCATTGCACTCCAGCCT
GGGGGACAGGGCAAGACTGTCTCTCAAAATAAAAA
AAAATAATAAAAATAAAAATAAAAGTAATTTCCAA
AACCTCATCTCATGGAAAGATCACAGGATGAAGGA
AAGCTAGACTCAACTCTGTGAATAGAAGTTGCTAT
ACTGTAAGTAAAGCAACAATTCAGAATACTGAATG
AGTTTAAATTGTTTTATATAGCACCCTTTTGGGCT
AGGGTTAATTACTAGATCTGACTTGGATAATTTGA
CACTTTGGGAAATGAACTCTGTTCTTGAGACTTGT
TCAGTGTATTTTAAACATCTGAGGAAGAAAACTTA
AATATGCACCTATTTATACCTATTCTTTCTTTAGG
TCAACATTTAACACCCACTGCATACATTAATTTGT
CCTTGTCTGCTCACTCCAGCAATTTAGACCTTAAC
AGTCACAAGAGACGTTCTTCTGTTACAAAGCCTTA
GTAAATTAAGGCAGTTTTGATTATATTCTAGGTCC
ACCTATGTCTGAAGCTAAATTCAGTATCTAACTGC
TAATGAACAAGTTTCCAAAATACTGTAAAAATACA
ATTAGTCAATTTGAGTAAATGCAAATATGATGAGA
AATCAATTTGCTATTTGGCCTGGCAAATGGGAACA
GTAAAATTCTGCTTTACTCTTCTCTAGTCTCCTTG

-continued

CCCCAGCTGCACCCACTACCCCAAAGTTGGCAGTT
TTGAGGTATGATTTTCAAGGAATTTTTTTAGTATT
AACATCTCCCTCTGAGAACTATGTACCTAAGGTCA
CGCATACAACTAGTCAATTCTGTTTTTATTACTCT
AACTATGTAGAAACAGTAAGTCACTTAAAACAATC
ACTTGGCTGGGTTTTTTCCCCTTTGTGCCACATTG
ATTCACCCTGACCCAAGAACTCCAGGGAAAATTCT
TTAATGTCAACTGGGCAACTCATTAACCTCTCTTT
AACATCAAGGGCTTGGGAAAAAAAAAAAAAAAGGTT
AGCCACAGGAATAACAAAAACCTGGAATTTATCTT
TCAGGTTTTGCTTTCTCTTTCTCACTTTGTTTAAA
GTATCTCGTACTCACAGTTCACAAATTAACCTTCA
CTGTCTCTTTCACATTAAGAGCTTATGCTTAAAGC
ATGCCCCCCTTTTCTAACTTGCTGGTTTACCATAA
ACTCCCCTAAGTAATAAAATTCCTAACCCAGTACT
GAGAGTCCTCCTTCTCTGCCACTTGGGCATTATTT
TACTAGTTTTTAAGCCATCATCGCACAAGAATCCA
AAAACCCTTAAATTTTTTAACCACTGGCAAATATG
TACAGCAAATTAGGTTAAGCATTTAATCTGGCTCA
TGCTCTATCATACTAAATATTCAGGTTTATCATAA
ACTCCTTAAAAACCATCAAAGGTCAACCAGAAACT
GATAACTCTTGAAAGGAGCAAACAGGTAAGATCTT
TGGAGTTTAAGCTTTTCTGAGATGTGTTGTGAAAA
ATCTAACGTGTTTATCGTATATTCAATGTAACAAC
CTGGAGAATCACAACTATATTTAAAGAGCCTCTGG
AAAATGAGGCCAGTACAGTGTGACTACATGTTTAA
TTTTCAATGTAATTTATTCCAAATAAACTGGTTCA
TGCTGACCACTTGTATTCAACTAA

Human BetaKlotho
(GenBank Accession No. NP 783864)
(SEQ ID NO: 9)

MKPGCAAGSPGNEWIFFSTDEITTRYRNTMSNGGL
QRSVILSALILLRAVTGFSGDGRAIWSKNPNFTPV
NESQLFLYDTFPKNFFWGIGTGALQVEGSWKKDGK
GPSIWDHFIHTHLKNVSSTNGSSDSYIFLEKDLSA
LDFIGVSFYQFSISWPRLFPDGIVTVANAKGLQYY
STLLDALVLRNIEPIVTLYHWDLPLALQEKYGGWK
NDTIIDIFNDYATYCFQMFGDRVKYWITIHNPYLV
AWHGYGTGMHAPGEKGNLAAVYTVGHNLIKAHSKV
WHNYNTHFRPHQKGWLSITLGSHWIEPNRSENTMD
IFKCQQSMVSVLGWFANPIHGDGDYPEGMRKKLFS
VLPIFSEAEKHEMRGTADFFAFSFGPNNFKPLNTM

-continued

AKMGQNVSLNLREALNWIKLEYNNPRILIAENGWF
TDSRVKTEDTTAIYMMKNFLSQVLQAIRLDEIRVF
GYTAWSLLDGFEWQDAYTIRRGLFYVDFNSKQKER
KPKSSAHYYKQIIRENGFSLKESTPDVQGQFPCDF
SWGVTESVLKPESVASSPQFSDPHLYVWNATGNRL
LHRVEGVRLKTRPAQCTDFVNIKKQLEMLARMKVT
HYRFALDWASVLPTGNLSAVNRQALRYYRCVVSEG
LKLGISAMVTLYYPTHAHLGLPEPLLHADGWLNPS
TAEAFQAYAGLCFQELGDLVKLWITINEPNRLSDI
YNRSGNDTYGAAHNLLVAHALAWRLYDRQFRPSQR
GAVSLSLHADWAEPANPYADSHWRAAERFLQFEIA
WFAEPLFKTGDYPAAMREYIASKHRRGLSSSALPR
LTEAERRLLKGTVDFCALNHFTTRFVMHEQLAGSR
YDSDRDIQFLQDITRLSSPTRLAVIPWGVRKLLRW
VRRNYGDMDIYITASGIDDQALEDDRLRKYYLGKY
LQEVLKAYLIDKVRIKGYYAFKLAEEKSKPRFGFF
TSDFKAKSSIQFYNKVISSRGFPFENSSSRCSQTQ
ENTECTVCLFLVQKKPLIFLGCCFFSTLVLLLSIA
IFQRQKRRKFWKAKNLQHIPLKKGKRVVS

*Mus musculus* beta klotho (KLB), mRNA
(GenBank Accession No. NM_031180)
(SEQ ID NO: 10)

AATGAAGACAGGCTGTGCAGCAGGGTCTCCGGGGA
ATGAATGGATTTTCTTCAGCTCTGATGAAAGAAAC
ACACGCTCTAGGAAAACAATGTCCAACAGGGCACT
GCAAAGATCTGCCGTGCTGTCTGCGTTTGTTCTGC
TGCGAGCTGTTACCGGCTTCTCCGGAGACGGGAAA
GCAATATGGGATAAAAAACAGTACGTGAGTCCGGT
AAACCCAAGTCAGCTGTTCCTCTATGACACTTTCC
CTAAAAACTTTTCCTGGGGCGTTGGGACCGGAGCA
TTTCAAGTGGAAGGGAGTTGGAAGACAGATGGAAG
AGGACCCTCGATCTGGGATCGGTACGTCTACTCAC
ACCTGAGAGGTGTCAACGGCACAGACAGATCCACT
GACAGTTACATCTTTCTGGAAAAAGACTTGTTGGC
TCTGGATTTTTTAGGAGTTTCTTTTTATCAGTTCT
CAATCTCCTGGCCACGGTTGTTTCCCAATGGAACA
GTAGCAGCAGTGAATGCGCAAGGTCTCCGGTACTA
CCGTGCACTTCTGGACTCGCTGGTACTTAGGAATA
TCGAGCCCATTGTTACCTTGTACCATTGGGATTTG
CCTCTGACGCTCCAGGAAGAATATGGGGGCTGGAA
AAATGCAACTATGATAGATCTCTTCAACGACTATG
CCACATACTGCTTCCAGACCTTTGGAGACCGTGTC

-continued

AAATATTGGATTACAATTCACAACCCTTACCTTGT

TGCTTGGCATGGGTTTGGCACAGGTATGCATGCAC

CAGGAGAGAAGGGAAATTTAACAGCTGTCTACACT

GTGGGACACAACCTGATCAAGGCACATTCGAAAGT

GTGGCATAACTACGACAAAAACTTCCGCCCTCATC

AGAAGGGTTGGCTCTCCATCACCTTGGGGTCCCAT

TGGATAGAGCCAAACAGAACAGACAACATGGAGGA

CGTGATCAACTGCCAGCACTCCATGTCCTCTGTGC

TTGGATGGTTCGCCAACCCCATCCACGGGGACGGC

GACTACCCTGAGTTCATGAAGACGGGCGCCATGAT

CCCCGAGTTCTCTGAGGCAGAGAAGGAGGAGGTGA

GGGGCACGGCTGATTTCTTTGCCTTTTCCTTCGGG

CCCAACAACTTCAGGCCCTCAAACACCGTGGTGAA

AATGGGACAAAATGTATCACTCAACTTAAGGCAGG

TGCTGAACTGGATTAAACTGGAATACGATGACCCT

CAAATCTTGATTTCGGAGAACGGCTGGTTCACAGA

TAGCTATATAAAGACAGAGGACACCACGGCCATCT

ACATGATGAAGAATTTCCTAAACCAGGTTCTTCAA

GCAATAAAATTTGATGAAATCCGCGTGTTTGGTTA

TACGGCCTGGACTCTCCTGGATGGCTTTGAGTGGC

AGGATGCCTATACGACCCGACGAGGGCTGTTTTAT

GTGGACTTTAACAGTGAGCAGAAAGAGAGGAAACC

CAAGTCCTCGGCTCATTACTACAAGCAGATCATAC

AAGACAACGGCTTCCCTTTGAAAGAGTCCACGCCA

GACATGAAGGGTCGGTTCCCCTGTGATTTCTCTTG

GGGAGTCACTGAGTCTGTTCTTAAGCCCGAGTTTA

CGGTCTCCTCCCCGCAGTTTACCGATCCTCACCTG

TATGTGTGGAATGTCACTGGCAACAGATTGCTCTA

CCGAGTGGAAGGGGTAAGGCTGAAAACAAGACCAT

CCCAGTGCACAGATTATGTGAGCATCAAAAAACGA

GTTGAAATGTTGGCAAAAATGAAAGTCACCCACTA

CCAGTTTGCTCTGGACTGGACCTCTATCCTTCCCA

CTGGCAATCTGTCCAAAGTTAACAGACAAGTGTTA

AGGTACTATAGGTGTGTGGTGAGCGAAGGACTGAA

GCTGGGCGTCTTCCCCATGGTGACGTTGTACCACC

CAACCCACTCCCATCTCGGCCTCCCCCTGCCACTT

CTGAGCAGTGGGGGGTGGCTAAACATGAACACAGC

CAAGGCCTTCCAGGACTACGCTGAGCTGTGCTTCC

GGGAGTTGGGGGACTTGGTGAAGCTCTGGATCACC

ATCAATGAGCCTAACAGGCTGAGTGACATGTACAA

-continued

CCGCACGAGTAATGACACCTACCGTGCAGCCCACA

ACCTGATGATCGCCCATGCCCAGGTCTGGCACCTC

TATGATAGGCAGTATAGGCCGGTCCAGCATGGGGC

TGTGTCGCTGTCCTTACATTGCGACTGGGCAGAAC

CTGCCAACCCCTTTGTGGATTCACACTGGAAGGCA

GCCGAGCGCTTCCTCCAGTTTGAGATCGCCTGGTT

TGCAGATCCGCTCTTCAAGACTGGCGACTATCCAT

CGGTTATGAAGGAATACATCGCCTCCAAGAACCAG

CGAGGGCTGTCTAGCTCAGTCCTGCCGCGCTTCAC

CGCGAAGGAGAGCAGGCTGGTGAAGGGTACCGTCG

ACTTCTACGCACTGAACCACTTCACTACGAGGTTC

GTGATACACAAGCAGCTGAACACCAACCGCTCAGT

TGCAGACAGGGACGTCCAGTTCCTGCAGGACATCA

CCCGCCTAAGCTCGCCCAGCCGCCTGGCTGTAACA

CCCTGGGGAGTGCGCAAGCTCCTTGCGTGGATCCG

GAGGAACTACAGAGACAGGGATATCTACATCACAG

CCAATGGCATCGATGACCTGGCTCTAGAGGATGAT

CAGATCCGAAAGTACTACTTGGAGAAGTATGTCCA

GGAGGCTCTGAAAGCATATCTCATTGACAAGGTCA

AAATCAAAGGCTACTATGCATTCAAACTGACTGAA

GAGAAATCTAAGCCTAGATTTGGATTTTTCACCTC

TGACTTCAGAGCTAAGTCCTCTGTCCAGTTTTACA

GCAAGCTGATCAGCAGCAGTGGCCTCCCCGCTGAG

AACAGAAGTCCTGCGTGTGGTCAGCCTGCGGAAGA

CACAGACTGCACCATTTGCTCATTTCTCGTGGAGA

AGAAACCACTCATCTTCTTCGGTTGCTGCTTCATC

TCCACTCTGGCTGTACTGCTATCCATCACCGTTTT

TCATCATCAAAAGAGAAGAAAATTCCAGAAAGCAA

GGAACTTACAAAATATACCATTGAAGAAAGGCCAC

AGCAGAGTTTTCAGCTAAACTGCCATTTCTGTCAT

AGTTTCAAGATTCACTCCGGCTCCATGTACTGGTA

ACTTACGATGTGAGAGACAGCTGTAACCAAGGTGA

AGACAATCGATGCCTCTGAAGTGTGGTTCAAATAA

TTCCTTCAGGTCCCGACAATCAGTGAGTCCGTTCT

CCGAGCTGAAGACACCCTGACAGTAACTCTGGGCG

TGACCCTAAACATCGCTTCAGGAAGTGTGAATCAC

-continued

GACTTCACATCCTTTTTCTCTAGCATTCTTCTGTA

AATAACAATCACTATTCATGGTCAAGAAATTAATT

TTAAAAAGT

*Mus musculus* beta klothoprotein
(GenBank Accession No. NP_112457)
(SEQ ID NO: 11)

MKTGCAAGSPGNEWIFFSSDERNTRSRKTMSNRAL

QRSAVLSAFVLLAVTGSGDGKAWDKKQYVSPVNPS

QLFLYDTFPKNFSWGVGTGAFQVEGSWKTDGRGPS

IWDRYVYSHLRGVNGTDRSTDSYIFLEKDLLALDF

LGVSFYQFSISWPRLFPNGTVAAVNAQGLRYYRAL

LDSLVLRNIEPIVTLYHWDLPLTLQEEYGGWKNAT

MIDLFNDYATYCFQTFGDRVKYWITIHNPYLVAWH

GFGTGMHAPGEKGNLTAVYTVGHNLIKAHSKVWHN

YDKNFRPHQKGWLSITLGSHWIEPNRTDNMEDVIN

CQHSMSSVLGWFANPIHGDGDYPEFMKTGAMIPEF

SEAEKEEVRGTADFFAFSFGPNNFRPSNTVVKMGQ

NVSLNLRQVLNWIKLEYDDPQILISENGWFTDSYI

KTEDTTAIYMMKNFLNQVLQAIKFDEIRVFGYTAW

TLLDGFEWQDAYTTRRGLFYVDFNSEQKERKPKSS

AHYYKQIIQDNGFPLKESTPDMKGRFPCDFSWGVT

ESVLKPEFTVSSPQFTDPHLYVWNVTGNRLLYRVE

GVRLKTRPSQCTDYVSIKKRVEMLAKMKVTHYQFA

LDWTSILPTGNLSKVNRQVLRYYRCVVSEGLKLGV

FPMVTLYHPTHSHLGLPLPLLSSGGWLNMNTAKAF

QDYAELCFRELGDLVKLWITINEPNRLSDMYNRTS

NDTYRAAHNLMIAHAQVWHLYDRQYRPVQHGAVSL

SLHCDWAEPANPFVDSHWKAAERFLQFEIAWFADP

LFKTGDYPSVMKEYIASKNQRGLSSSVLPRFTAKE

SRLVKGTVDFYALNHFTTRFVIHKQLNTNRSVADR

DVQFLQDITRLSSPSRLAVTPWGVRKLLAWIRRNY

RDRDIYITANGIDDLALEDDQIRKYYLEKYVQEAL

KAYLIDKVKIKGYYAFKLTEEKSKPRFGFFTSDFR

AKSSVQFYSKLISSSGLPAENRSPACGQPAEDTDC

TICSFLVEKKPLIFFGCCFISTLAVLLSITVFHHQ

KRRKFQKARNLQNIPLKKGHSRVFS

Pharmaceutical Compositions

Another aspect of the disclosure pertains to pharmaceutical compositions of the compounds of the disclosure. The pharmaceutical compositions of the disclosure typically comprise a compound of the disclosure and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer, or in a fat pad described herein. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, certain methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., long-acting FGF21) optionally is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

Exemplary dosages of compounds (e.g., long-acting FGF21) of the disclosure include e.g., about 0.0001% to 5%, about 0.0001% to 1%, about 0.0001% to 0.1%, about 0.001% to 0.1%, about 0.005%-0.1%, about 0.01% to 0.1%, about 0.01% to 0.05% and about 0.05% to 0.1%.

Exemplary or long-acting or stable forms of FGF21, as described herein, may have a half-life greater than that of the native or wild type FGF21. The half-life of long-acting FGF21 may be greater than the half-life of native FGF21 by at least 1 hour, at least 2 hours, at least 3 hours, at 4 hours, at least 5 hours, at least 6 hours, at least 7 hours, at least 8 hours, at least 9 hours, at least 10 hours, at least 11 hours, at least 12 hours, at least 24 hours, at least 48 hours, at least 72 hours, at least 4 days, at least 5 days, at least 6 days, at least 7 days, at least 2 weeks, at least 3 weeks, and at least a month, but at least some amount over that of the native FGF21.

Exemplary stabilized or long-acting forms of FGF21 (i.e., long-acting FGF21) as described herein, may have a half-life of at least 1.5×, at least 2×, at least 3×, at least 4×, at least 5×, at least 8×, at least 10×, at least 12×, at least 15×, at least 20×, at least 30×, at least 40×, at least 50×, at least 60×, or at least 70× the half-life of a native FGF21 peptide, when assayed for stability under identical conditions. Exemplary stabilized or long-acting forms of FGF21 (i.e., long-acting FGF21) as described herein, may possesses a half-life of at least 0.8 h, at least 1 h, at least 2 h, at least 3 h, at least 4 h, at least 5 h, at least 7 h, at least 10 h, at least 15 h, at least 20 h, at least 25 h, at least 28 h or at least 30 h in the circulation of a mammal, optionally wherein the mammal is human.

The compound(s) of the disclosure can be administered in a manner that prolongs the duration of the bioavailability of the compound(s), increases the duration of action of the compound(s) and the release time frame of the compound by an amount selected from the group consisting of at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, and at least a month, but at least some amount over that of the compound(s) in the absence of the fat pad delivery system. Optionally, the duration of any or all of the preceding effects is extended by at least 30 minutes, at least an hour, at least 2 hours, at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks or at least a month.

A compound of the disclosure can be formulated into a pharmaceutical composition wherein the compound is the only active agent therein. Alternatively, the pharmaceutical composition can contain additional active agents. For example, two or more compounds of the disclosure may be used in combination. Moreover, a compound of the disclosure can be combined with one or more other agents that have modulatory effects on cancer.

Kits

The disclosure also includes kits that include a composition of the disclosure, optionally also including a compound (e.g., a long-acting FGF21), and instructions for use.

This invention is further illustrated by the following examples which should not be construed as limiting. The contents of all references, patents, and published patent applications cited throughout this application, as well as the figures, are incorporated herein by reference.

EXAMPLES

Example 1: Materials and Methods

Mouse Models of Retinal/Choroidal Neovascularization

Oxygen-induced retinopathy: mice were exposed to 75% oxygen from P7 to P12. The mice were then returned to room air until P17 (Connor et al., 2009; Smith et al., 1994). High oxygen led to vessel loss and the relative hypoxia induced neovascularization which reached to maximum at P17 (Smith et al., 1994). Both genders of mouse pups were used with body weight ranging from 5.5 to 7 grams (Connor et al., 2009). The mice were randomly assigned to either native FGF21 (5 mg/kg, twice per day) or long-acting FGF21 (1 mg/kg PF-05231023) or phosphate buffered saline (PBS). The mice were intraperitoneally injected daily from P12 to P16. For the intra-vitreal injection of PF-05231023 (0.5 μl 10 μg/μl stock per eye) was delivered using 10 μl syringe with 35G needle (World Precision Instruments, Inc.)

at P12. The contralateral eye was injected with vehicle control. At P17, retinal neovascularization was quantified (Connor et al., 2009; Smith et al., 1994). Mice were sacrificed at P17 using a lethal intraperitoneal injection of ketamine/xylazine, and the eyes were enucleated, followed by fixation in 4% paraformaldehyde for 1 hour at room temperature. The retinas were dissected and stained overnight at room temperature with fluorescent *Griffonia Bandeiraea simplicifolia* Isolectin B4 (Alexa Fluor 594, I21413, Molecular Probes, 10 μg/ml) in 1 mM CaCl2 in PBS. The images of whole mounted retina were taken at 5× magnification on a Zeiss AxioObserver.Z1 microscope and merged to form one image with AxioVision 4.6.3.0 software. Retinal neovascularization was quantified as previously reported (Connor et al., 2009). Percentages of neovascularization were calculated by comparing the number of pixels in the neovascular areas with the total number of pixels in the retina. n is the number of eyes quantified.

$Vldlr^{-/-}$ mice: $Vldlr^{-/-}$ mice develop pathological neovascularization (retinal angiomatous proliferation or RAP as well as later onset choroidal neovascularization). RAP extends from the deep retinal vascular layer of the outer plexiform layer (OPL) towards the retinal pigment epithelium (RPE). The mouse pups were treated with a long-acting FGF21 analogue (0.5 mg/kg PF-05231023) or PBS from P8 to P15. At P16, neovascular lesions were quantified (Joyal et al., 2016). The eyes were enucleated and fixed in 4% paraformaldehyde for 1 hour at room temperature. The retinas were stained overnight with fluorescent *Griffonia Bandeiraea simplicifolia* Isolectin B4 (Alexa Fluor 594, I21413, Molecular Probes, 10 μg/ml) in 1 mM CaCl2 in PBS then washed with PBS and whole mounted with photoreceptors facing up. The images of whole mounted retina were taken at 5× magnification on a Zeiss AxioObserver.Z1 microscope and merged to form one image with AxioVision 4.6.3.0 software. Vascular lesions were analyzed using the SWIFT_MACTEL method, a plugin in Image J (Joyal et al., 2016).

Laser-induced choroidal neovascularization: Four laser burns were induced by a green Argon laser pulse, with duration of 70 ms and power of 240 mW in 6-8-week-old C57BL/6J mice. Both male and female mice were used (Lambert et al., 2013). A long-acting FGF21 analogue (10 mg/kg PF-05231023) or PBS were intraperitoneally injected every other day one week before and after the laser photocoagulation induction. The eyes were enucleated and fixed in 4% paraformaldehyde for 1 hour at room temperature. The choroid were penetrated with 1% Triton X-100 PBS for one hour at room temperature and stained overnight with fluorescent *Griffonia Bandeiraea simplicifolia* Isolectin B4 (Alexa Fluor 594, I121413, Molecular Probes, 10 μg/ml) in 1 mM CaCl2 in PBS. The choroids were washed with PBS and whole mounted. The images of whole mounted choroid were taken at 10× or 20× magnification on a Zeiss AxioObserver.Z1 microscope. Lesion area was quantified (Gong et al., 2015).

Real-Time PCR

RNA from retinas or choroid-retina complex was extracted and reverse-transcribed to cDNA. PCR was conducted for Fgfr1, Fgfr2, Fgfr3, Fgfr4, Klb, Apn, Vegfa, Dynamin2 and Tnfα. Cyclophilin A was used as internal control. Freshly isolated retinas were lysed with QIAzol™ lysis reagent and incubated on ice for 15 minutes. 20% chloroform was added and samples were incubated for 5 minutes at room temperature. RNA was extracted according to the manufacturer's instructions using a PureLink® RNA Mini Kit (#12183018A, Ambion). RNA was then reverse transcribed using iScript™ cDNA synthesis kit (#1708891, Bio-Rad). The sequences of primers were Fgfr1 ((F: 5'-ACT CTG CGC TGG TTG AAA AAT-3' (SEQ ID NO: 12), R: 5'-GGT GGC ATA GCG AAC CTT GTA-3' (SEQ ID NO: 13)); Fgfr2 ((F: 5'-GCT ATA AGG TAC GAA ACC AGC AC-3' (SEQ ID NO: 14), R: 5'-GGT TGA TGG ACC CGT ATT CAT TC-3' (SEQ ID NO: 15)); Fgfr3 ((F: 5'-GCC TGC GTG CTA GTG TTC T-3' (SEQ ID NO: 16), R: 5'-TAC CAT CCT TAG CCC AGA CCG-3'(SEQ ID NO: 17)); Fgfr4 ((F: 5'-TCC ATG ACC GTC GTA CAC AAT-3' (SEQ ID NO: 18), R: 5'-ATT TGA CAG TAT TCC CGG CAG-3' (SEQ ID NO: 19)); β-klotho (Klb) ((F: 5'-TGT TCT GCT GCG AGC TGT TAC-3' (SEQ ID NO: 20), R: 5'-CCG GAC TCA CGT ACT GTT TTT-3' (SEQ ID NO: 21)); Adipoq: ((F: 5'-GAA GCC GCT TAT GTG TAT CGC-3' (SEQ ID NO: 22), R: 5'-GAA TGG GTA CAT TGG GAA CAG T-3' (SEQ ID NO: 23)); Vegfa ((F: 5'-GGA GAT CCT TCG AGG AGC ACT T-3' (SEQ ID NO: 24), R: 5'-GCG ATT TAG CAG CAG ATA TAA GAA-3' (SEQ ID NO: 25)); Tnfα ((F: 5'-AAG GAC CTG GTA CAT GAA CTG G-3' (SEQ ID NO: 26), R: 5'-GGT TCT GGG TGT CAA GTG TCG-3' (SEQ ID NO: 27)); Dynamin 2 ((F: 5'-TTT GGC GTT CGA GGC CAT T-3' (SEQ ID NO: 28); R: 5'-CAG GTC CAC GCA TTT CAG AC-3' (SEQ ID NO: 29)) Quantitative analysis of gene expression was performed using an Applied Biosystems 7300 Sequence Detection System with the SYBR Green Master mix kit, and gene expression was calculated relative to Cyclophilin A ((F: 5'-CAG ACG CCA CTG TCG CTT T-3' (SEQ ID NO: 30); R: 5'-TGT CTT TGG AAC TTT GTC TGC AA-3' (SEQ ID NO: 31)) using the ΔΔCt method.

ELISA for Mouse Serum FGF21

Neonatal mouse serum levels of FGF21 were measured with ELISA following the manufacturer's protocol (Eagle Biosciences, #F2131-K01). Briefly, 50 μl mouse serum or standards were first added on the designated microwell. 50 μl tracer antibody was then added and the plate was incubated at room temperature for 2 hours. The wells were washed and incubated with 100 μl ELISA HRP substrate at room temperature in dark for 20 minutes. Finally, 100 μl ELISA stop solution were added and the signals were read at 450/650 nm.

Statistics

All data were used except for low quality images that were insufficient for analysis. Data represent mean±SEM. 2-tailed unpaired t-test or ANOVA with Bonferroni's multiple comparison test was used for comparison of results as specified (Prism v5.0; GraphPad Software, Inc., San Diego, Calif.). Statistically significant difference was set at $P \leq 0.05$. For phenotypic data, a dot represents each retina or choroid; for qPCR data, each dot represents a number of replicates from 4-6 pooled retinas.

Figure 1B:
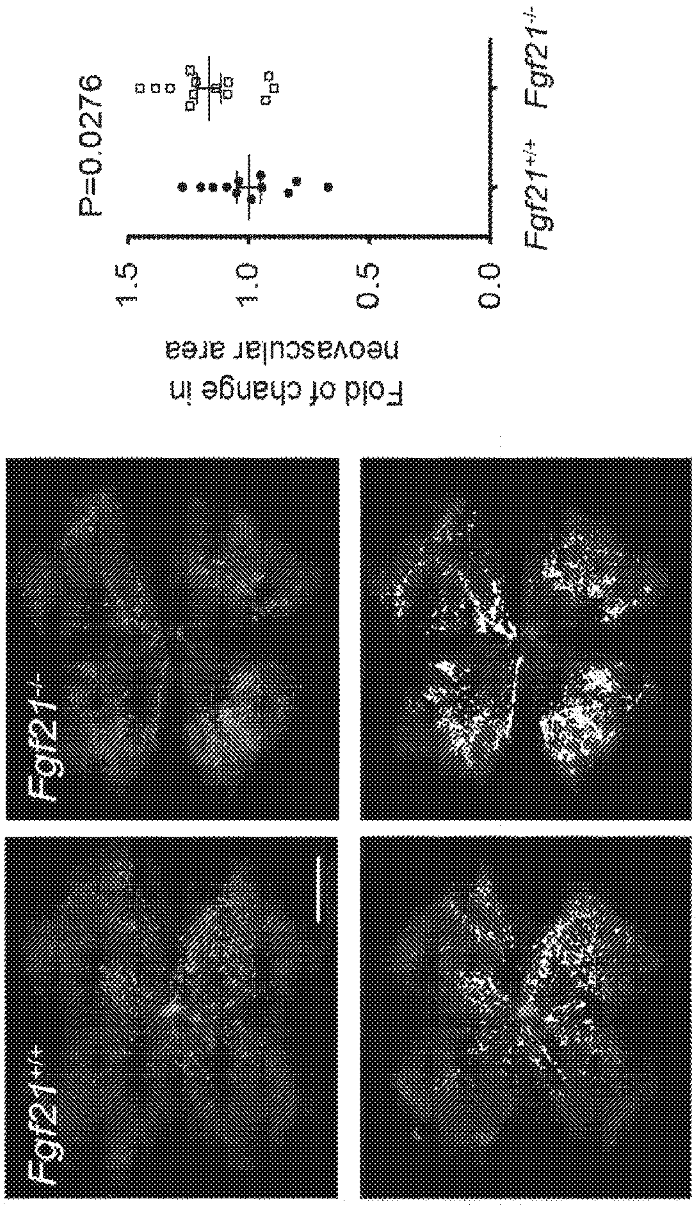
Figure 5:
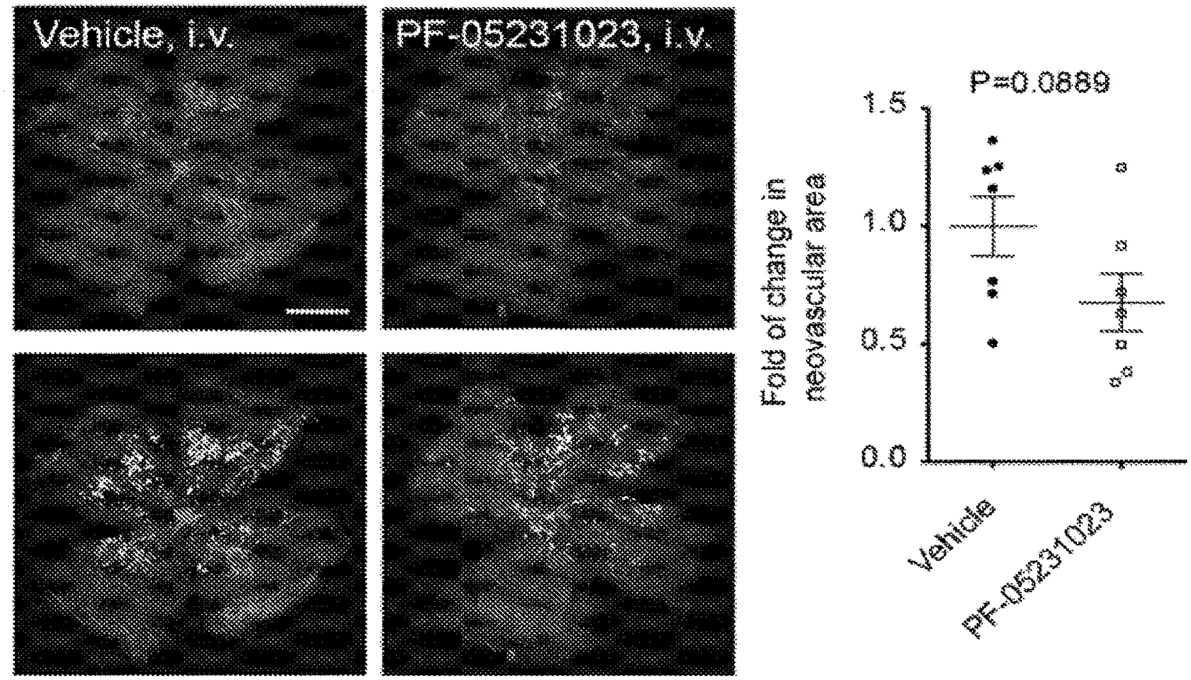
FIG. 5 depicts micrographs and charts demonstrating that intra-vitreal PF-05231023 administration induced a trend of reduction in neovascularization in OIR. In WT mice after P12 intra-vitreal PF-05231023, a trend of reduction of neovascularization was observed. The contralateral eye was injected with vehicle. (n=7 retinas per group). Unpaired t test. See also FIGS. 1A-1B.
Figure 6A:
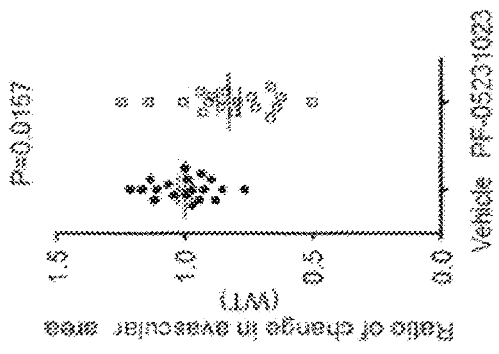
FIGS. 6A-6D depict graphs demonstrating that FGF21 promoted normal retinal revascularization. Quantification of revascularization in P17 retinal whole mounts after oxygen-induced retinopathy was performed.
Figure 6B:
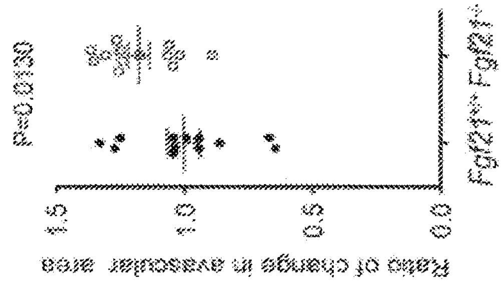
Figure 6C:
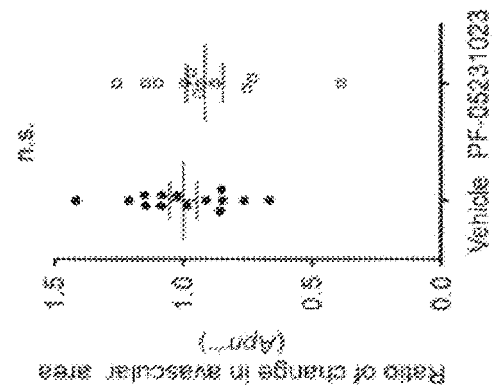
Figure 6D:
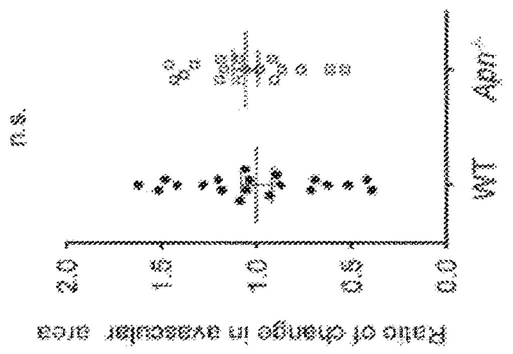

Example 2: Long-Acting FGF21 Suppressed Hypoxia-Induced Retinal Neovascularization Early vessel growth cessation or vessel loss in retinopathy of prematurity and diabetic retinopathy has been previously described to lead to hypoxia and nutrient deficits, which drives vessel overgrowth (Chen and Smith, 2007; Shin et al., 2014). To investigate the effects of FGF21 on pathologic neovessel growth under hypoxia, FGF21 was administered to mice having oxygen-induced retinopathy (Smith et al., 1994). After five-day exposure to 75% oxygen, mouse pups with their nursing dam were returned to room air. The oxygen exposure led to vaso-obliteration in the central retina, and the relatively avascular hypoxic retina induced neovascularization (Smith et al., 1994) extending from the retina into the vitreous at the boundary between vascular and non-vascularized areas (Connor et al., 2009). The mouse pups were intraperitoneally injected with native FGF21 or a long-acting FGF21 analog, PF-05231023 (Talukdar et al., 2016), or vehicle control for five days. Native FGF21, which exhibits a short half-life (0.4 hours; Huang et al., 2013), did not affect neovascularization (FIG. 1A) whereas administration of PF-05231023, which possesses a biological half-life of 28 hours (Huang et al., 2013) significantly decreased neovascularization (FIG. 1A). To confirm the role of FGF21 in retinal neovascularization, the impact of FGF21 deficiency on oxygen-induced retinopathy was examined by comparing wild-type ($Fgf21^{+/+}$) and knockout ($Fgf21^{-/-}$) mice. $Fgf21^{-/-}$ mice exhibited increased neovascularization (FIG. 1B). Noting the strong inhibition of pathologic neovessel formation observed when PF-05231023 was administered, the relatively smaller effects of native FGF21 and the effects of endogenous FGF21 deficiency observed upon retinal neovascularization, these latter effects were likely due to the short half-life of native FGF21 (0.4 hours) (Huang et al., 2013) and low endogenous FGF21 levels (about 658.3±66.4 pg/ml in normal neonatal mouse serum detected by ELISA), respectively, while the former effects of long-acting FGF21 were also reflective of the short half-life of native FGF21. To determine if long-acting FGF21 directly inhibited neovascularization, intra-vitreal injection of PF-05231023 was performed, and indeed was found to reduce retinal neovascularization, as compared to the extent of retinal neovascularization observed in a vehicle-injected contralateral eye (FIG. 5). FGF21 also promoted retinal revascularization through APN, although APN might not be required for "basal" revascularization in OIR (FIG. 6A-6D). In some embodiments, improved revascularization has likely decreased the stimulus for proliferative neovascularization.

Figure 2A:
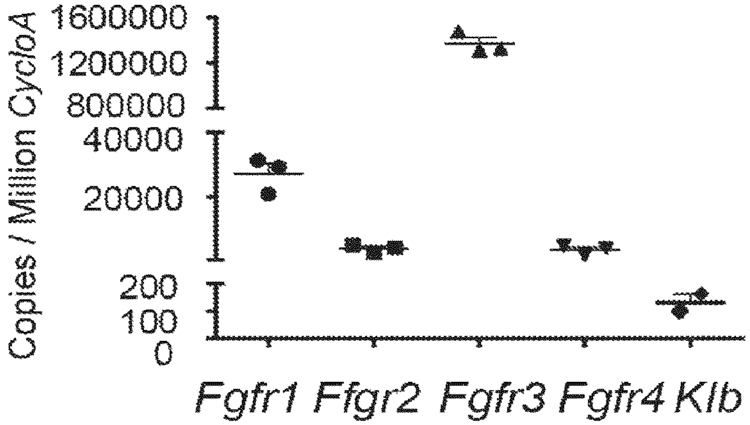
FIGS. 2A-2F depict micrographs, charts, and schematics demonstrating that FGF21 suppressed retinal neovascularization via adiponectin (APN) to reduce TNFα. Quantification of neovascularization in P17 retinal whole mounts was performed after oxygen-induced retinopathy. In whole mounts, vessels were stained with isolectin (red) and neovascularization was pseudo-colored white. Representative images are shown. Scale bar, 1 mm. Data was presented as mean±SEM. Unpaired t test. n.s., no significance. Fold of change was calculated.
Figure 2B:
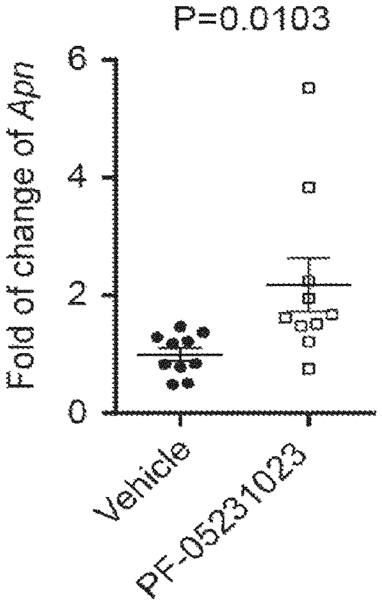
Figure 2C:
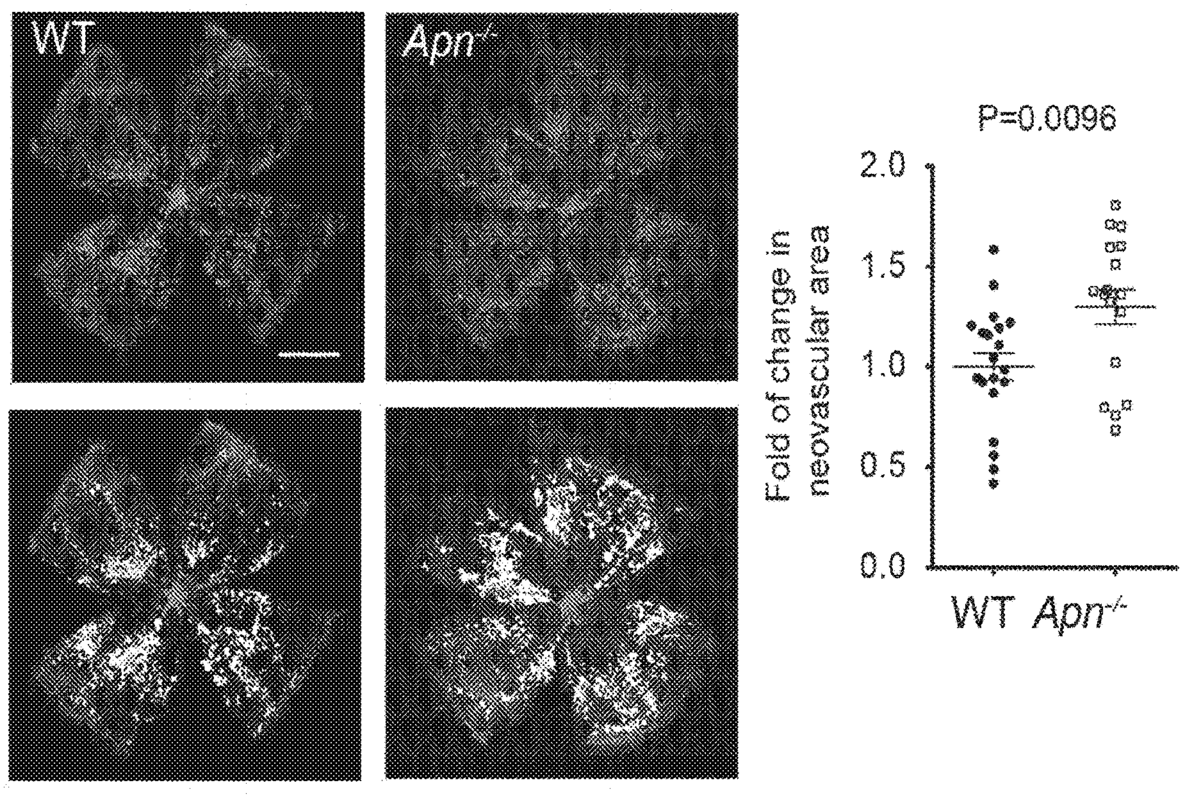
Figure 2D:
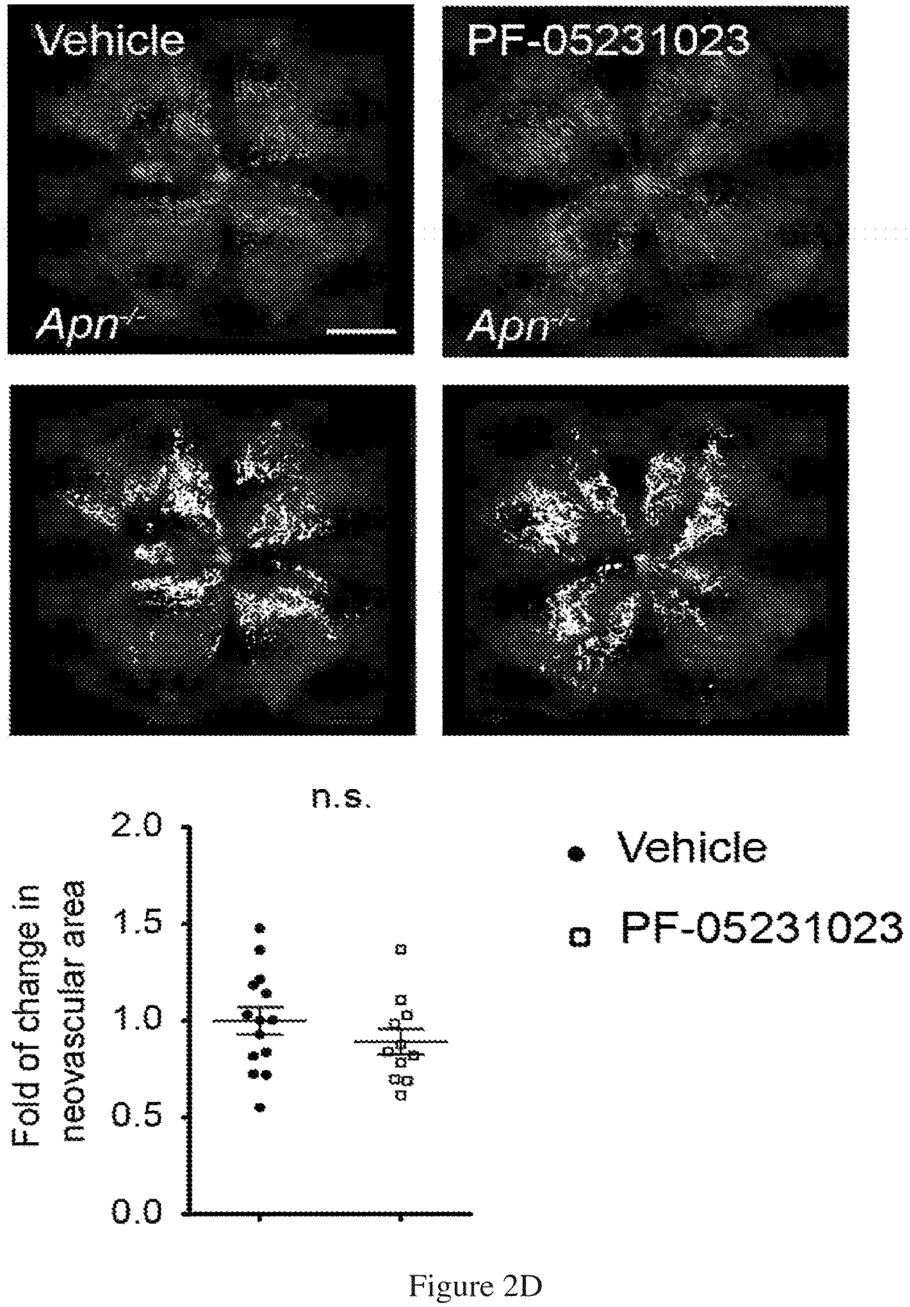
Figure 2E:
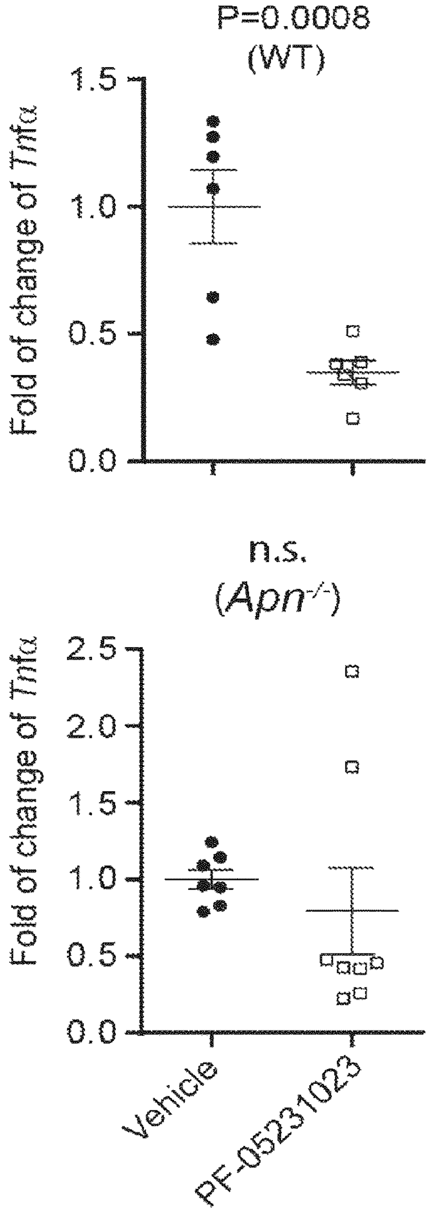
Figure 2F:
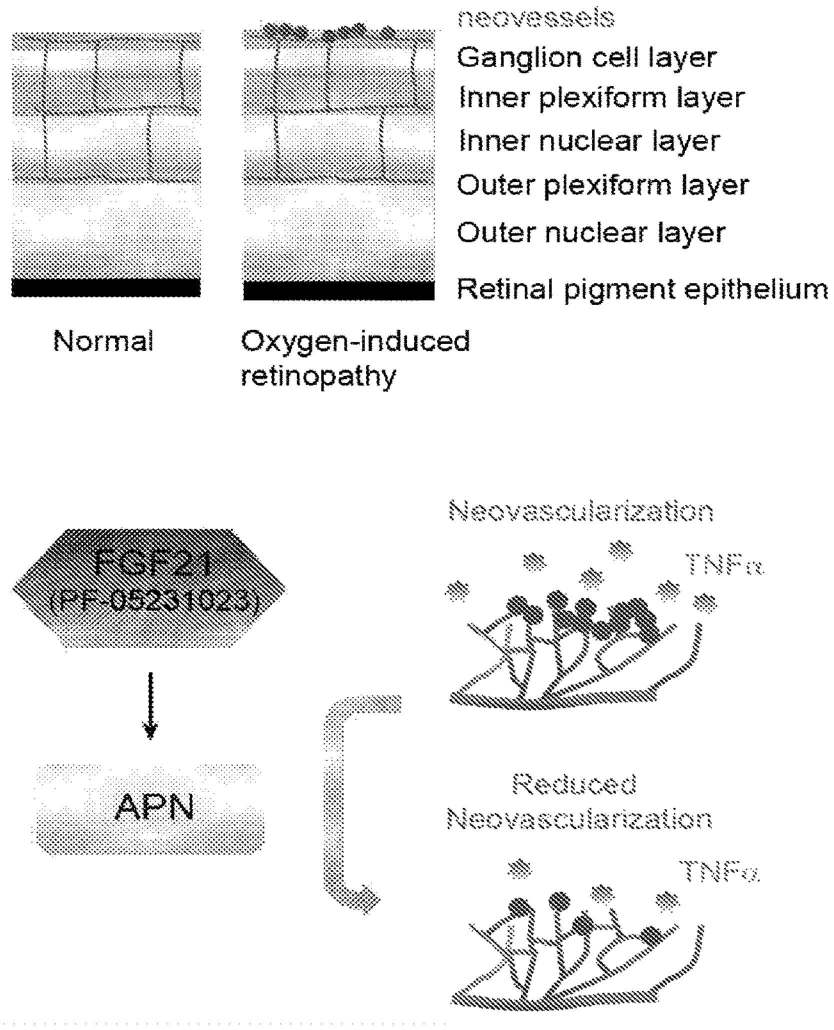
Figure 7A:
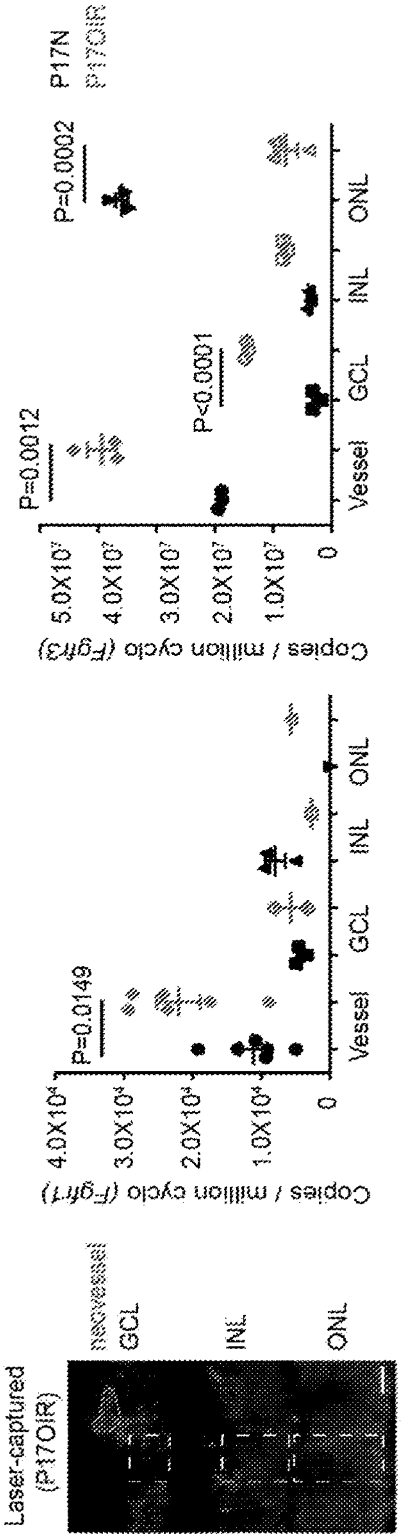
FIGS. 7A-7D depict micrographs and charts demonstrating that FGF21 receptors and adiponectin colocalized in retinal neovessels.
Figure 7B:
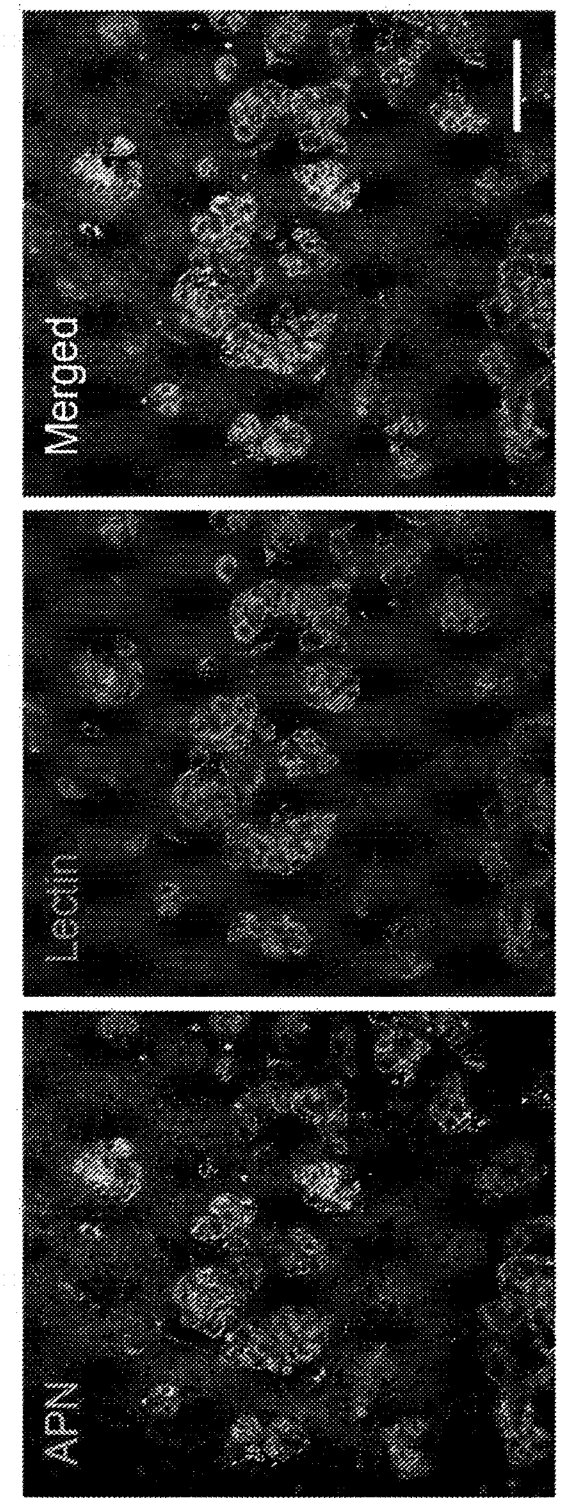
Figure 7C:
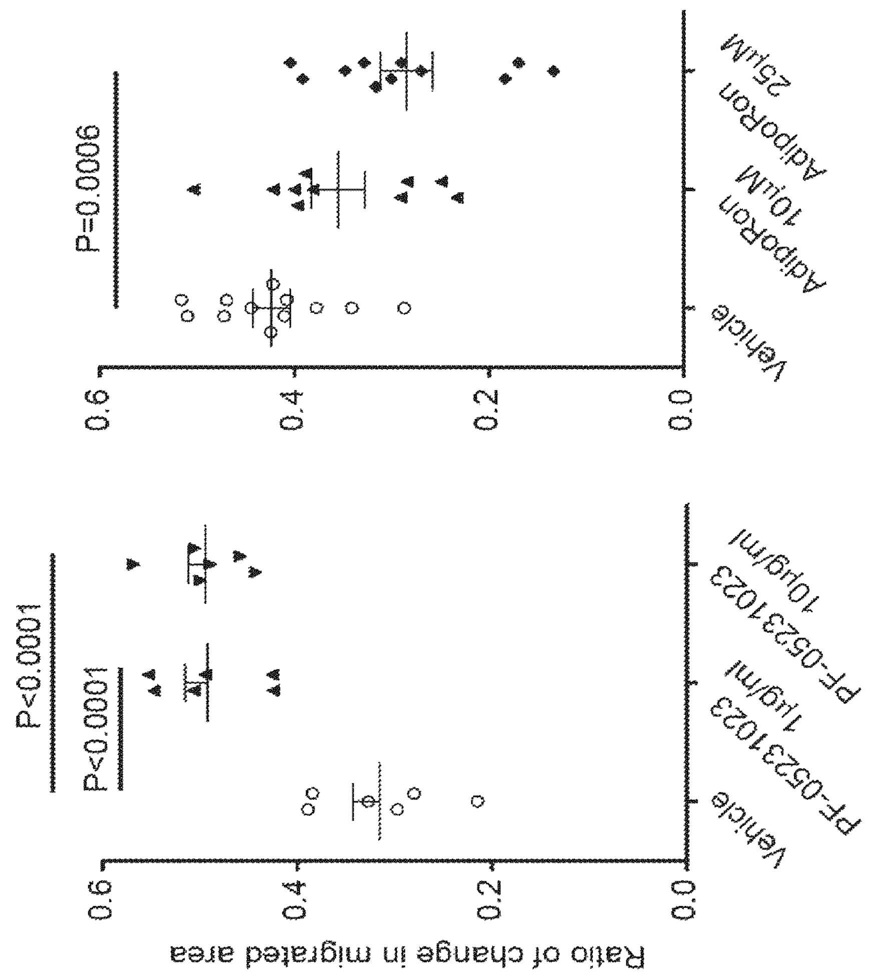
Figure 7D:
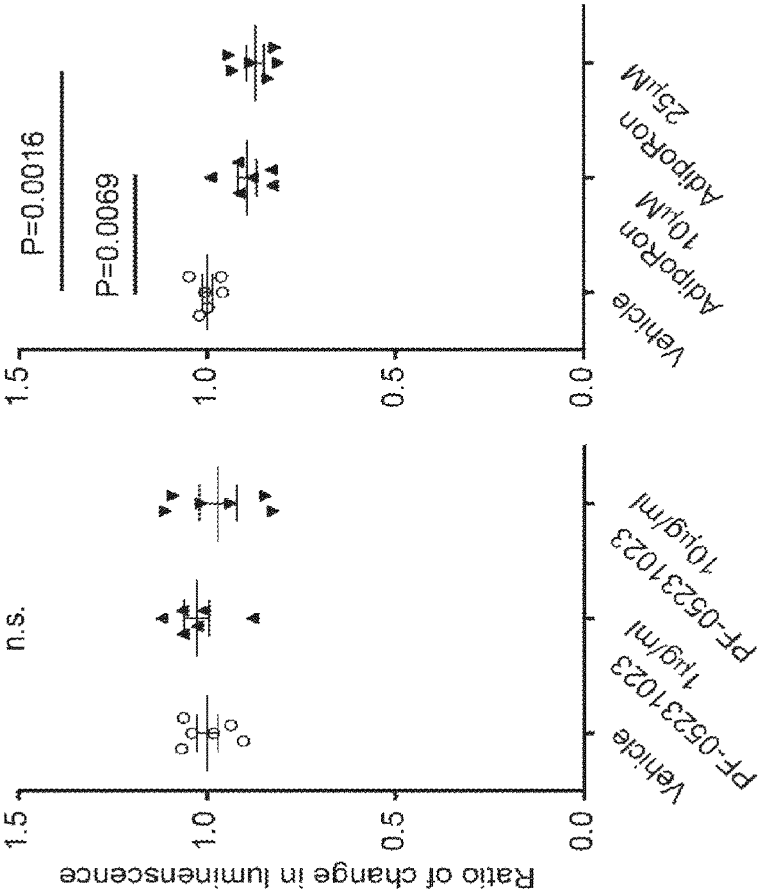

Without wishing to be bound by theory, in some embodiments, FGF21 apparently exerted its effects through interaction with its receptor, FGFR1, and co-receptor β-klotho (KLB) (Ding et al., 2012; Foltz et al., 2012; Suzuki et al., 2008). As described herein, FGF21 receptor 1, 2, 3, 4 and Klb mRNA were all expressed in the mouse retina (FIG. 2A). Fgfr1 and fgfr3 were highly expressed in neovessels, and co-localized with APN (FIG. 7A-7B). PF-05231023 administration at P17 increased retinal Apn (FIG. 2B), an important mediator of FGF21 effects on metabolic function (Holland et al., 2013; Lin et al., 2013). APN receptor agonist AdipoRon inhibited endothelial cell function in vitro (FIG. 7C-7D). To determine if APN also mediated the protection conferred by long-acting FGF21 against retinal neovascularization, the retinal vasculature in APN knockout ($Apn^{-/-}$) mice having oxygen-induced retinopathy was examined, in the presence or absence of PF-05231023 administration. APN deficiency worsened retinal neovascularization (FIG. 2C), and lack of APN completely abolished the beneficial effects of PF-05231023 otherwise exhibited in reducing neovascularization in hypoxic retinas (FIG. 2D). APN has been described as inhibiting retinal neovascularization by decreasing the levels of tumor necrosis factor (TNF)α (Higuchi et al., 2009). Consistent with such observations, PF-05231023 suppressed Tnfα expression in neovascular WT retina, but the suppression was abolished with APN deficiency (FIG. 2E). In some embodiments, long-acting FGF21 inhibited pathological retinal neovessel growth by targeting APN and reducing TNFα (FIG. 2F), a key risk factor for oxygen-induced retinopathy (Kociok et al., 2006).

Each year, over 15 million babies are born preterm and possessing an incompletely vascularized retina, which—if normal vascularization does not occur postnatally—sets the stage for the progression to proliferative retinopathy (Hellstrom et al., 2013). Retinopathy of prematurity is a leading cause of blindness in children (Gilbert et al., 1997). As described herein, low serum APN levels positively correlated with proliferative retinopathy in premature infants (Fu et al., 2015). Increasing circulating APN levels were associated with less retinal neovascularization in mice (Fu et al., 2015; Higuchi et al., 2010). In mouse oxygen-induced retinopathy, FGF21 administration increased retinal Apn levels and reduced Tnfα levels, and also suppressed pathologic neovessel growth (FIG. 2).

Diabetic retinopathy currently afflicts approximately 93 million people worldwide, and of those, 28 million have vision-threatening proliferative retinopathy (Abcouwer and Gardner, 2014). The levels of FGF21 in type 1 diabetes have been observed as lower than those in healthy controls (Xiao et al., 2012; Zibar et al., 2014). In streptozotocin-induced type 1 diabetic mice, a FGF21 analog reduced blood glucose levels with improved glucose uptake in brown adipose tissue (Kim et al., 2015). FGF21 prevented renal lipid accumulation, and attenuated renal dysfunction in type 1 diabetic mice (Zhang et al., 2013). In type 2 diabetes, serum FGF21 levels have been observed as higher in patients with retinopathy versus no retinopathy (Esteghamati et al., 2016; Lin et al., 2014). FGF21 treatment decreased body weight and improved the lipid profile (decreases triglycerides and increases HDL cholesterol levels) in type 2 diabetes patients, non-human primates and in obese rodents (Bernardo et al., 2015; Gaich et al., 2013; Schlein et al., 2016; Talukdar et al., 2016). It was hypothesized that FGF21 could play a beneficial role in diabetes and diabetic complications, such as diabetic retinopathy. The mouse model of oxygen-induced retinopathy has been commonly used to model hypoxia-induced neovascularization in proliferative diabetic retinopathy (Lai and Lo, 2013). As described elsewhere herein, long-acting FGF21 is also contemplated as helping to prevent proliferative diabetic retinopathy, optionally via a direct effect upon early diabetic retinal neurovascular loss and/or late neovascularization, optionally also related to the hyperglycemic aspect of diabetic retinopathy.

Figure 3A:
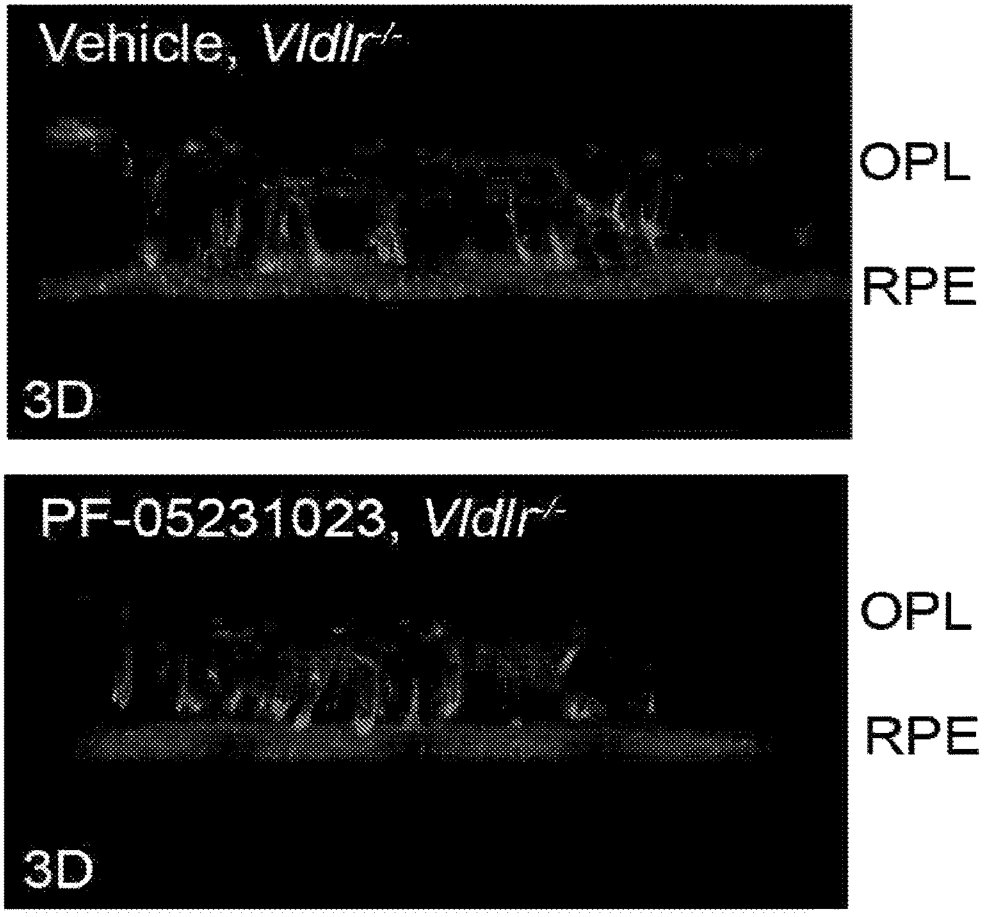
FIGS. 3A-3D depict micrographs and charts demonstrating that exogenous FGF21 decreased retinal neovascularization in $Vldlr^{-/-}$ mice.
Figure 3B:
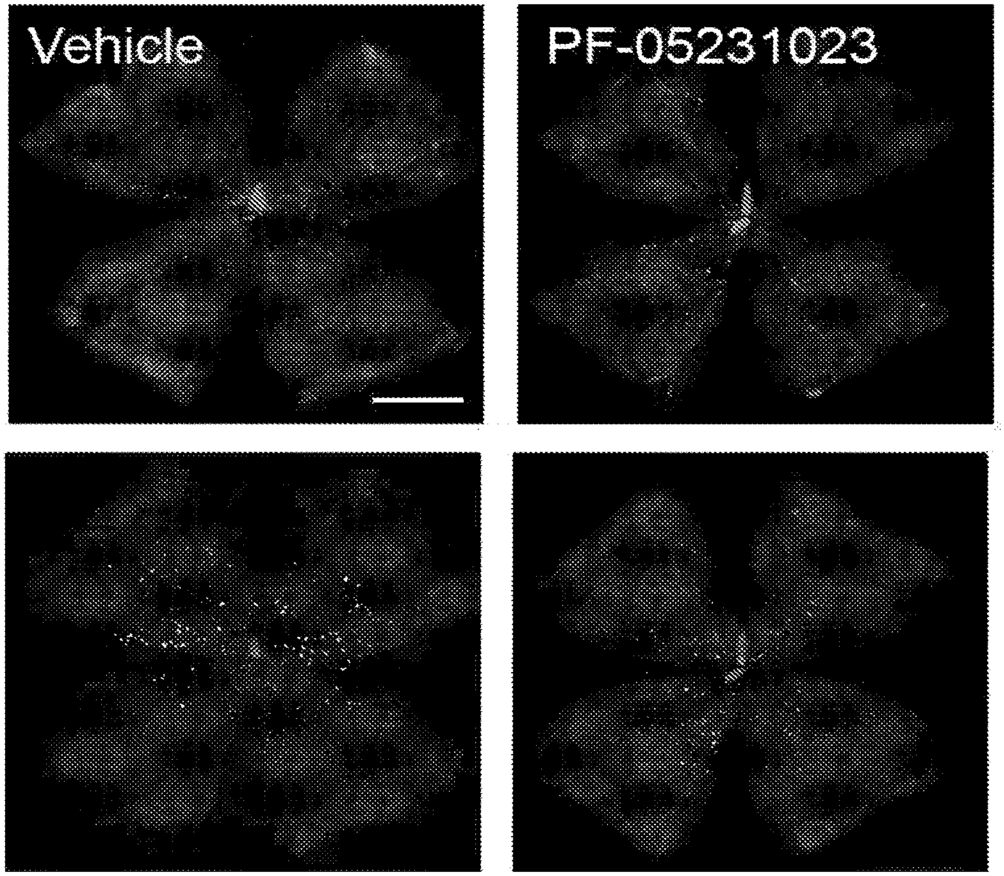
Figure 3C:
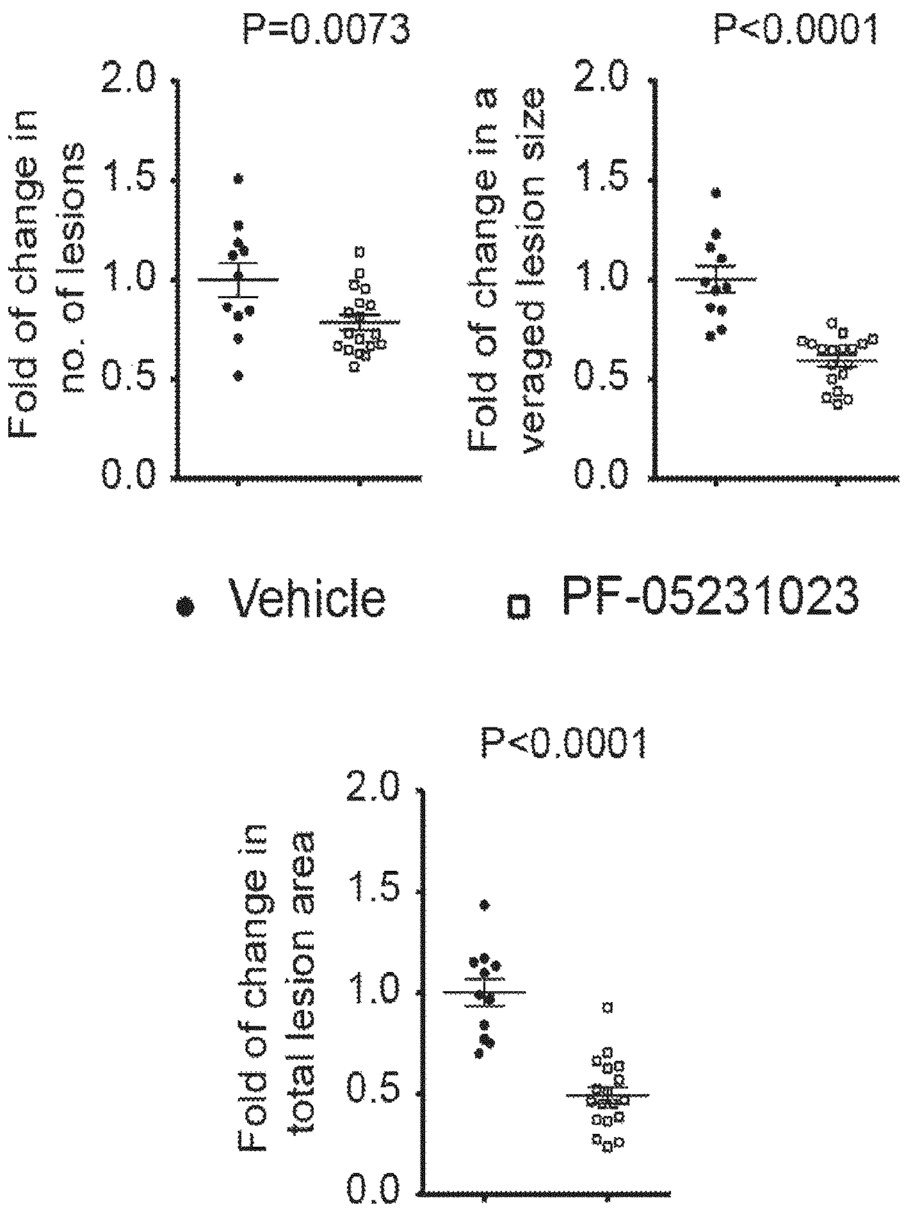
Figure 3D:
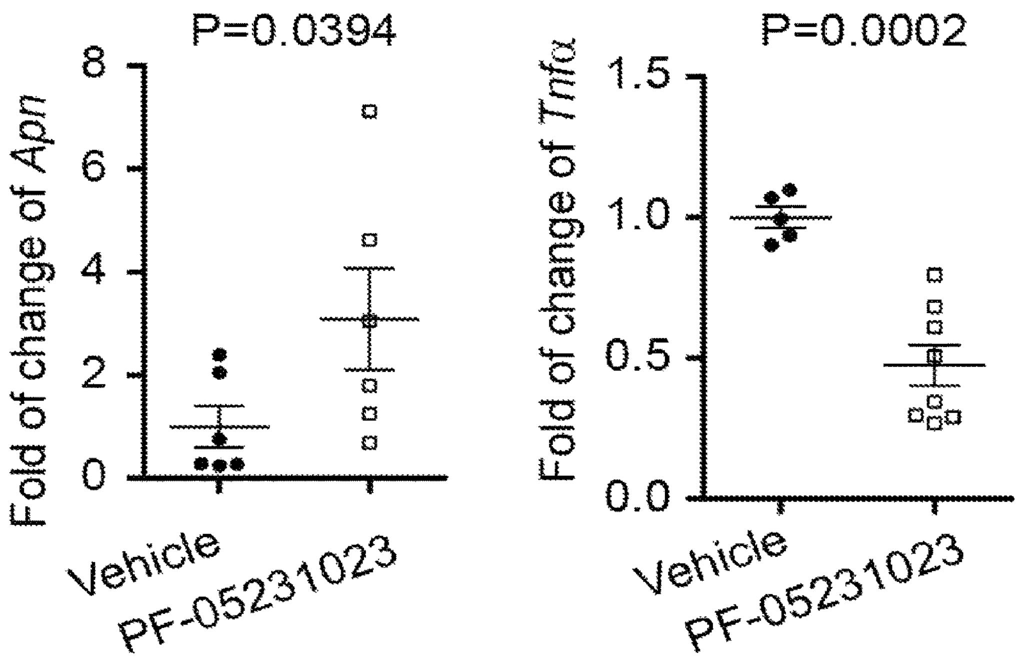

Example 3: Long-Acting FGF21 Administration Protected Against Retinal Neovascularization Induced by Energy-Deficiency in $Vldlr^{-/-}$ Mice In addition to lack of oxygen, an inadequate fuel supply can also drive retinal neovascularization (Joyal et al., 2016). Absence of the very low density lipoprotein receptor (VLDLR) has previously been described as associated with retinal angiomatous proliferation and choroidal neovascularization, similar to the neovascularization that has been seen with macular telangiectasia and late proliferative age-related macular degeneration (Engelbert and Yannuzzi, 2012; Lambert et al., 2016). In $Vldlr^{-/-}$ mice, abnormal blood vessels extended towards starved photoreceptors (Joyal et al., 2016) (FIG. 3A). To assess whether long-acting FGF21 protected against metabolism-induced pathologic neovessel growth, PF-05231023 was administered intraperitoneally at 0.5 mg/kg daily from P8 to P15 to $Vldlr^{-/-}$ mice. PF-05231023 administration attenuated the neovascular lesions (FIG. 3A, 3B, 3C) and increased retinal Apn, while decreasing Tnfα (FIG. 3D) in $Vldlr^{-/-}$ mice. Thus, long-acting FGF21 administration protected against retinal neovascularization induced by energy-deficiency in $Vldlr^{-/-}$ mice.

Figure 4A:
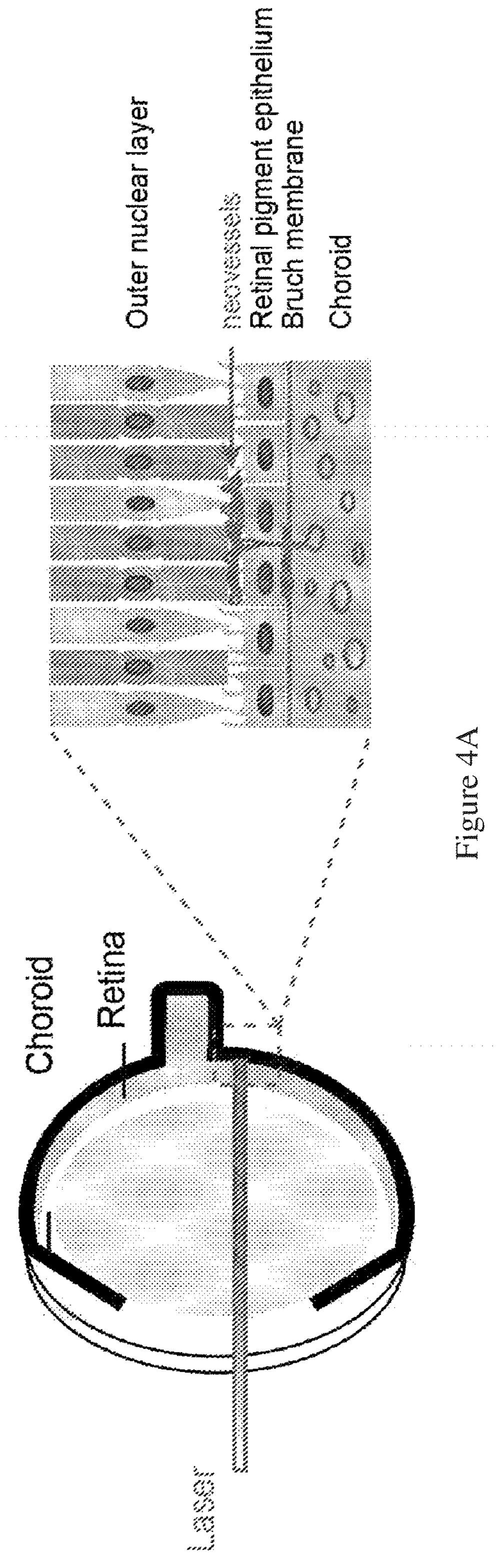
FIGS. 4A-4D depicts micrographs, charts, and schematics demonstrating that FGF21 administration decreased choroidal neovascularization in mice.
Figure 4B:
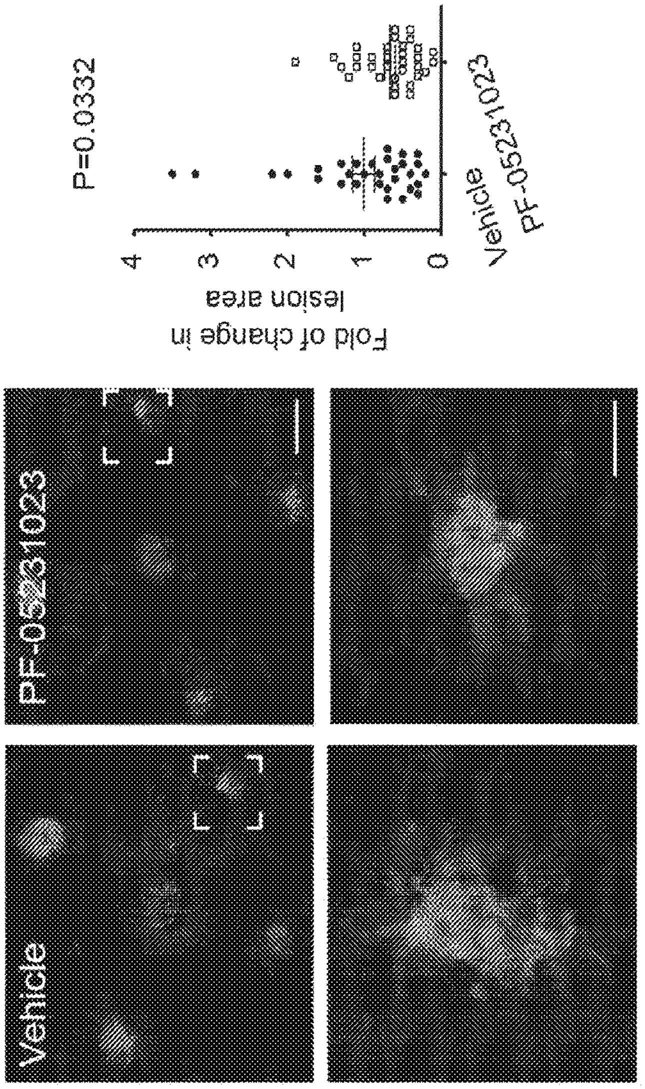
Figure 4C:
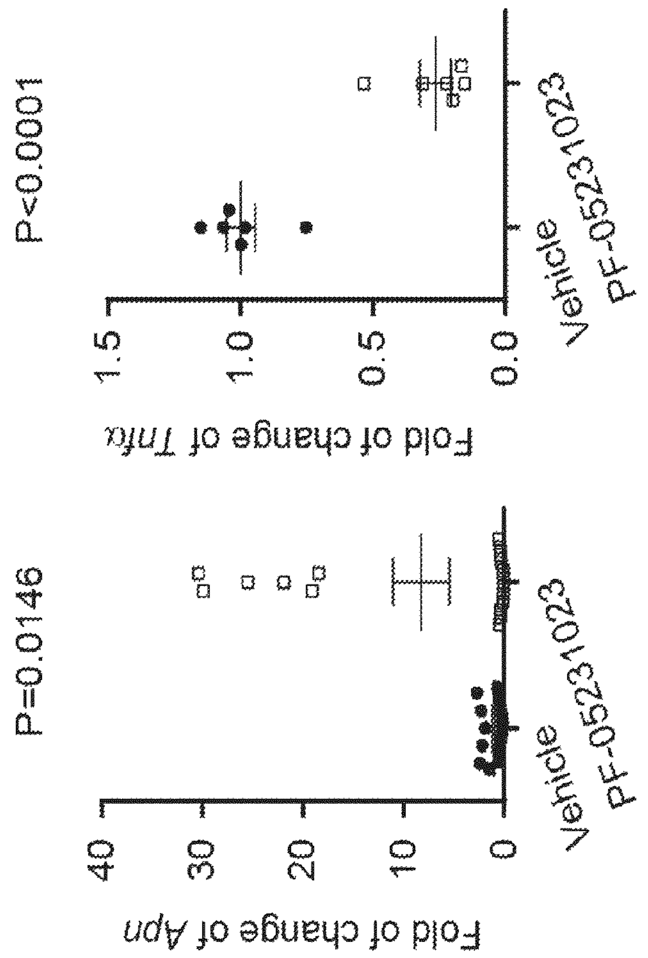

Example 4: Long-Acting FGF21 Inhibited Laser-Induced Choroidal Neovascularization in Mice Choroidal neovascularization, a condition in which neovessels extend from the choriocapillaris into the subretinal space, is vision-threatening in age-related macular degeneration. In a laser-induced choroidal neovascularization mouse model, laser burns disrupt Bruch's membrane to induce choroidal neovessel growth (Ryan, 1979) (FIG. 4A). To test the effects of long-acting FGF21 in such a model, 10 mg/kg PF-05231023 was administered every other day one week before and after the laser injury in 6-8-week-old C57B/6J mice. As shown in FIG. 4B, PF-05231023 administration inhibited choroidal neovessel formation. In the mouse choroidal neovascularization model, PF-05231023 also induced Apn and reduced Tnfα in the choroid-retina complex (FIG. 4C).

Neovascularization more generally is a leading cause of vision loss in both age-related macular degeneration and macular telangiectasia in the population over age 50 years (Heeren et al., 2014; Yonekawa et al., 2015). Metabolic alterations in retinal pigment epithelial cells and photoreceptors contribute to disease progression (Barron et al., 2001; Joyal et al., 2016). In Vldlr$^{-/-}$ mice, which have an inadequate fuel supply driving retinal neovascularization, long acting FGF21 administration was observed to reduce neovascular lesion formation. As described herein, long-acting FGF21 administration likely attenuated the development of metabolically driven retinal neovascularization, modeling macular telangiectasia and some aspects of neovascular age-related macular degeneration. Furthermore, in laser-induced choroidal neovascularization modeling inflammatory aspects of neovascular age-related macular degeneration (Parmeggiani et al., 2012), FGF21 also suppressed pathological choroidal angiogenesis in adult mice.

Figure 4D:
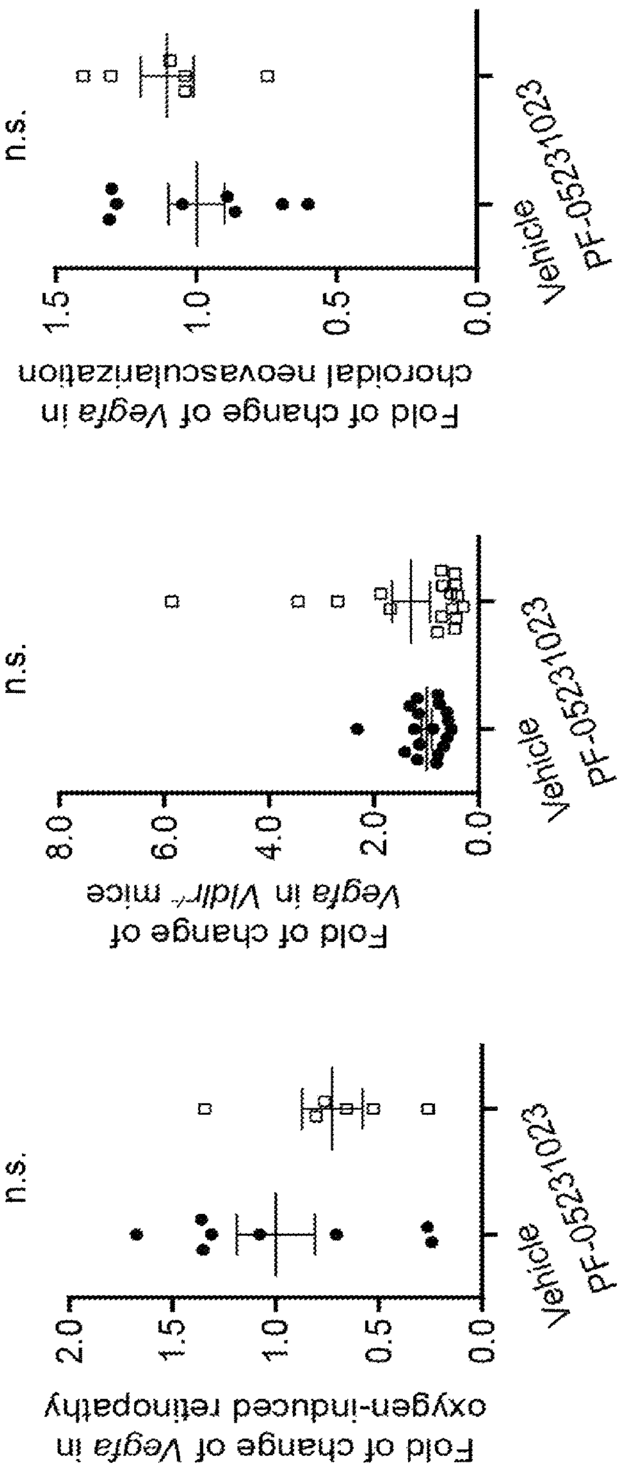

In summary, there is an unmet need for effective treatment of vision-threatening eye neovessel growth. As described herein, long-acting FGF21 inhibited retinal and choroidal neovascularization mediated by APN in mice. APN suppresses TNFα transcription and mRNA stability in macrophages (Park et al., 2008; Wulster-Radcliffe et al., 2004). Inhibition of TNFα has been previously characterized as leading to decreased retinal and choroidal neovascularization (Kociok et al., 2006; Shi et al., 2006), possibly through increased endothelial cell sprouting (Hangai et al., 2006; Sainson et al., 2008). Long-acting FGF21 was observed herein to have promoted migration in HRMECs in vitro (FIG. 7C). Different target systems are likely affected by long-acting FGF21 with opposite angiogenic responses. As described herein, long-acting FGF21 inhibitory effects on retinal and choroidal neovascularization were identified as independent of VEGFA (FIG. 4D). It has previously been reported in clinical data that little to no effect of long-acting FGF21 has been observed upon glycemic endpoints, which has tempered enthusiasm for potential further development of long-acting FGF21 in the clinic for metabolic diseases; however, the instant disclosure offers a phenotypic basis and some mechanistic insights into a new indication where long-acting FGF21 is likely to provide an effective prophylactic and/or therapeutic against retinopathy, thereby providing a next-generation standard of care for patients with pathological vascular proliferation in retinopathy of prematurity, diabetic retinopathy, macular telangiectasia and age-related macular degeneration.

Example 5: FGF21 in Retinopathy of Prematurity

Hyperglycemia is a recently described risk factor for retinopathy of prematurity (ROP) in premature infants. In streptozotocin (STZ)-induced hyperglycemic ROP mouse model, retinal vascular development was confirmed as delayed. Specifically, FGF21 deficiency delayed normal retinal vascular network formation and worsened hyperglycemic ROP in such mice. Native (nFGF21) and long-acting FGF21 (PF-05231023) treatment were both observed to have promoted retinal vessel growth in hyperglycemic ROP. The protection of FGF21 observed was also confirmed as dependent upon adiponectin (APN).

Figure 8A:
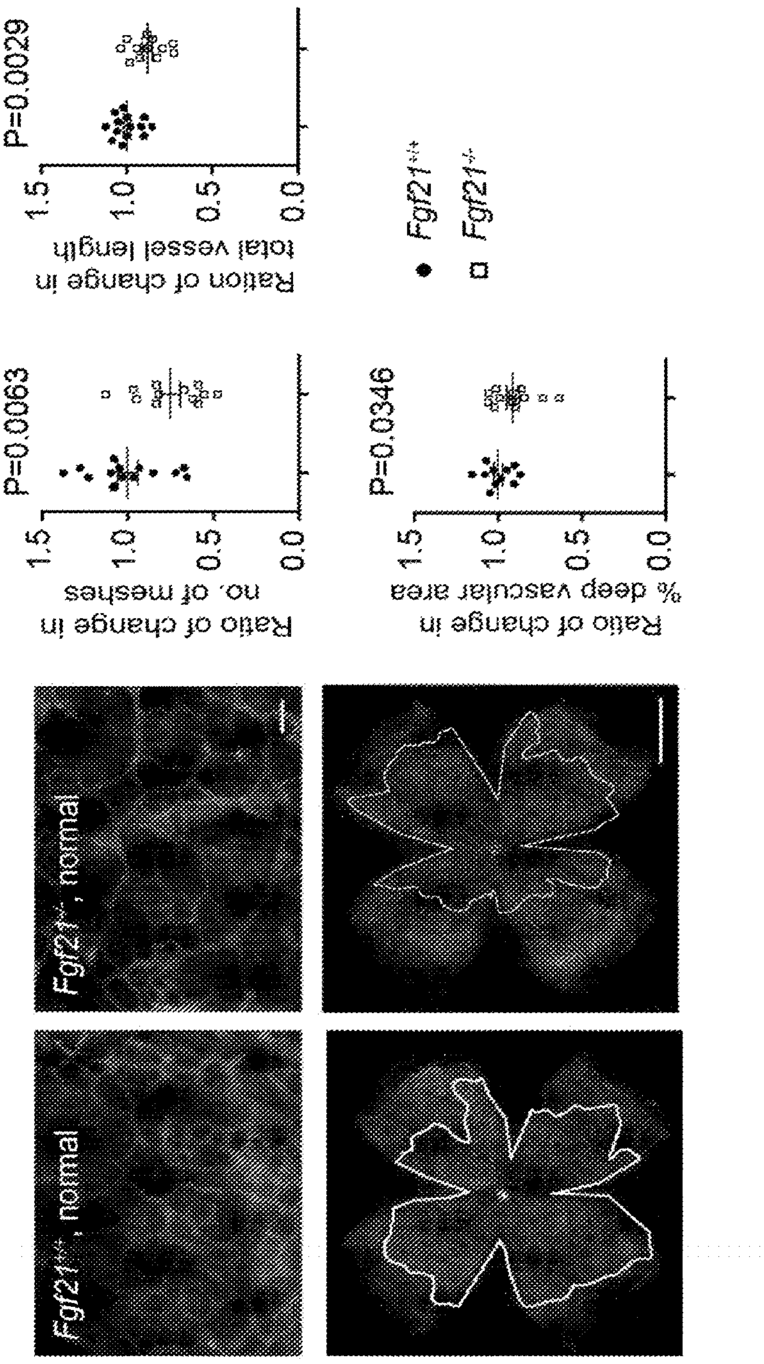
FIGS. 8A-8B depict micrographs and graphs demonstrating the observed impacts of FGF21 deficiency.
Figure 8B:
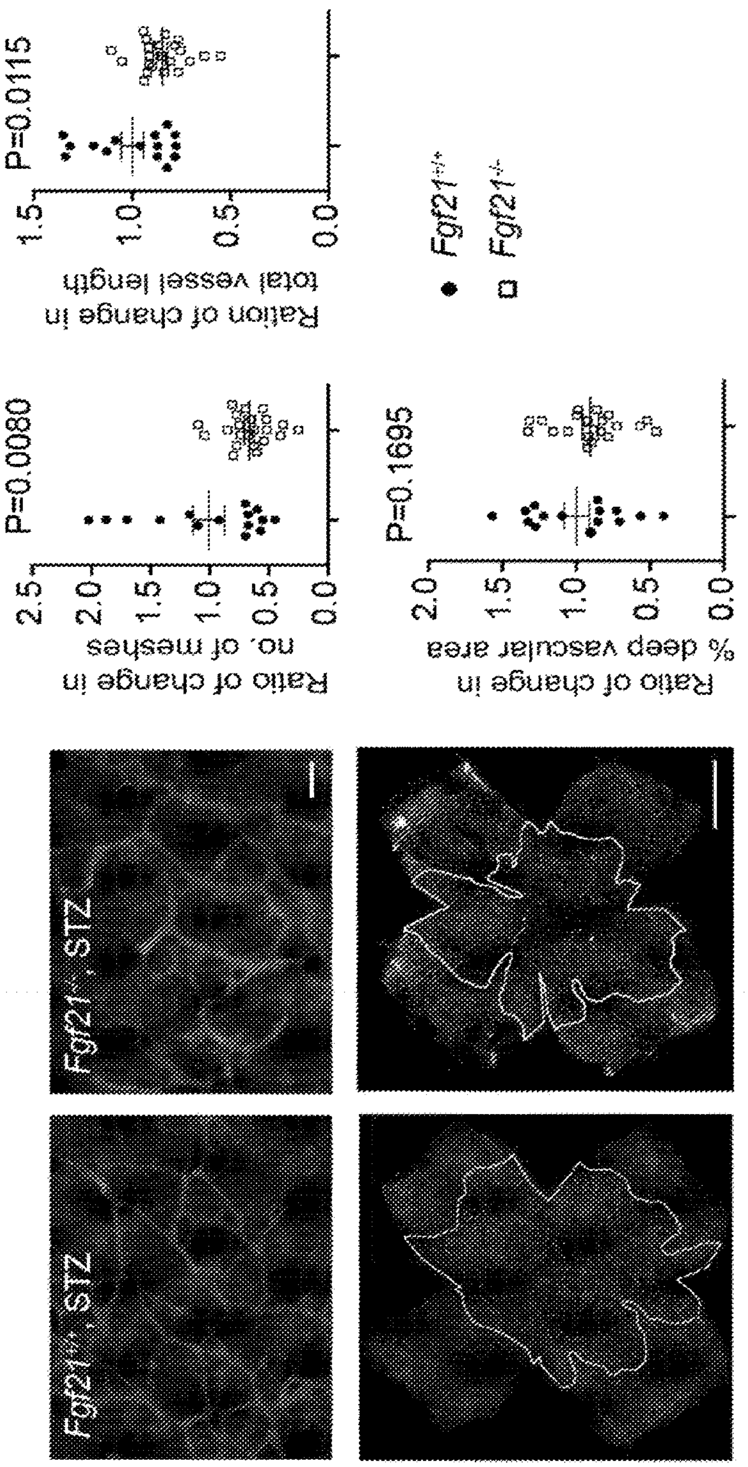
Figure 9A:
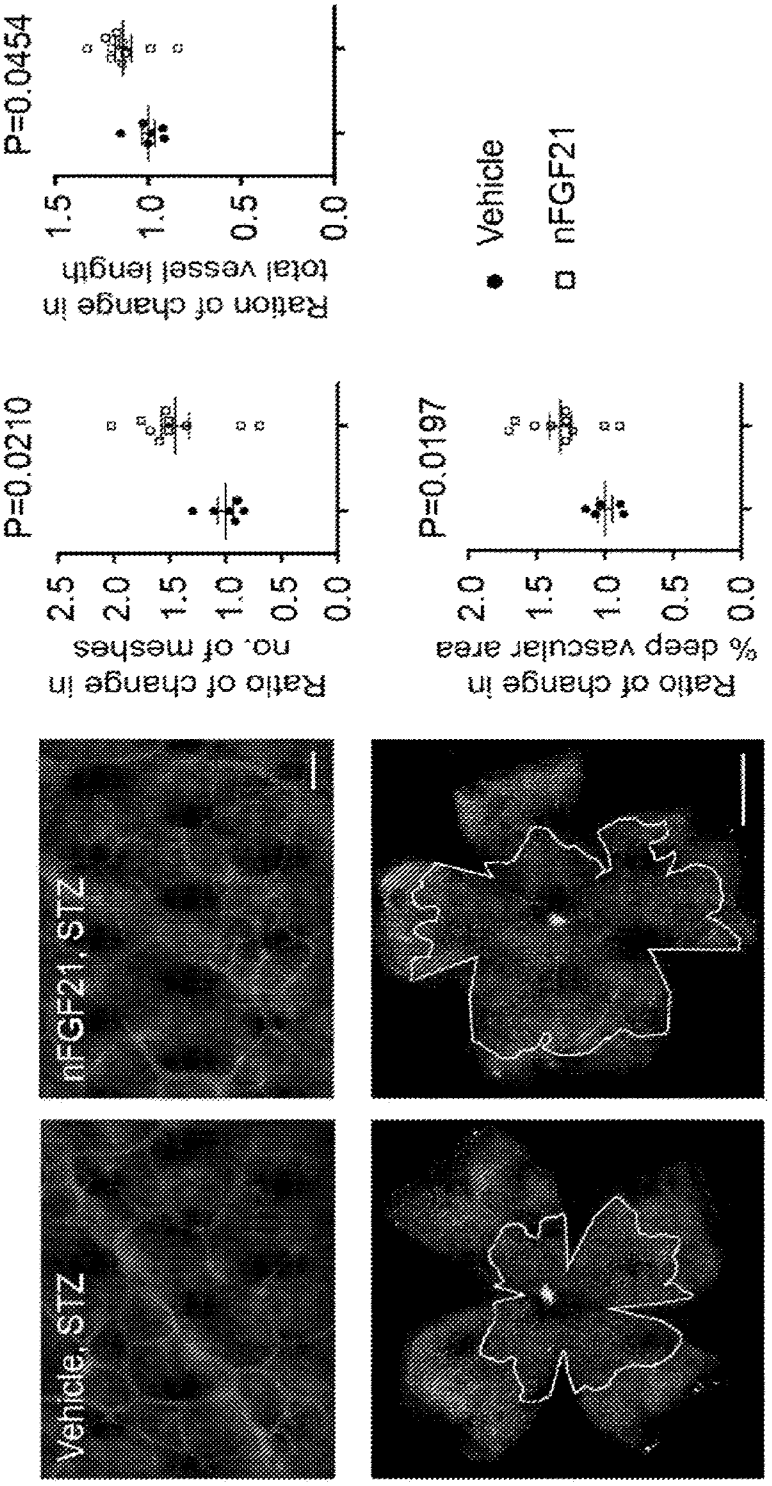
FIGS. 9A-9B show micrographs and graphs demonstrating that FGF21 promoted retinal vascular development in hyperglycemic mouse neonates.
Figure 9B:
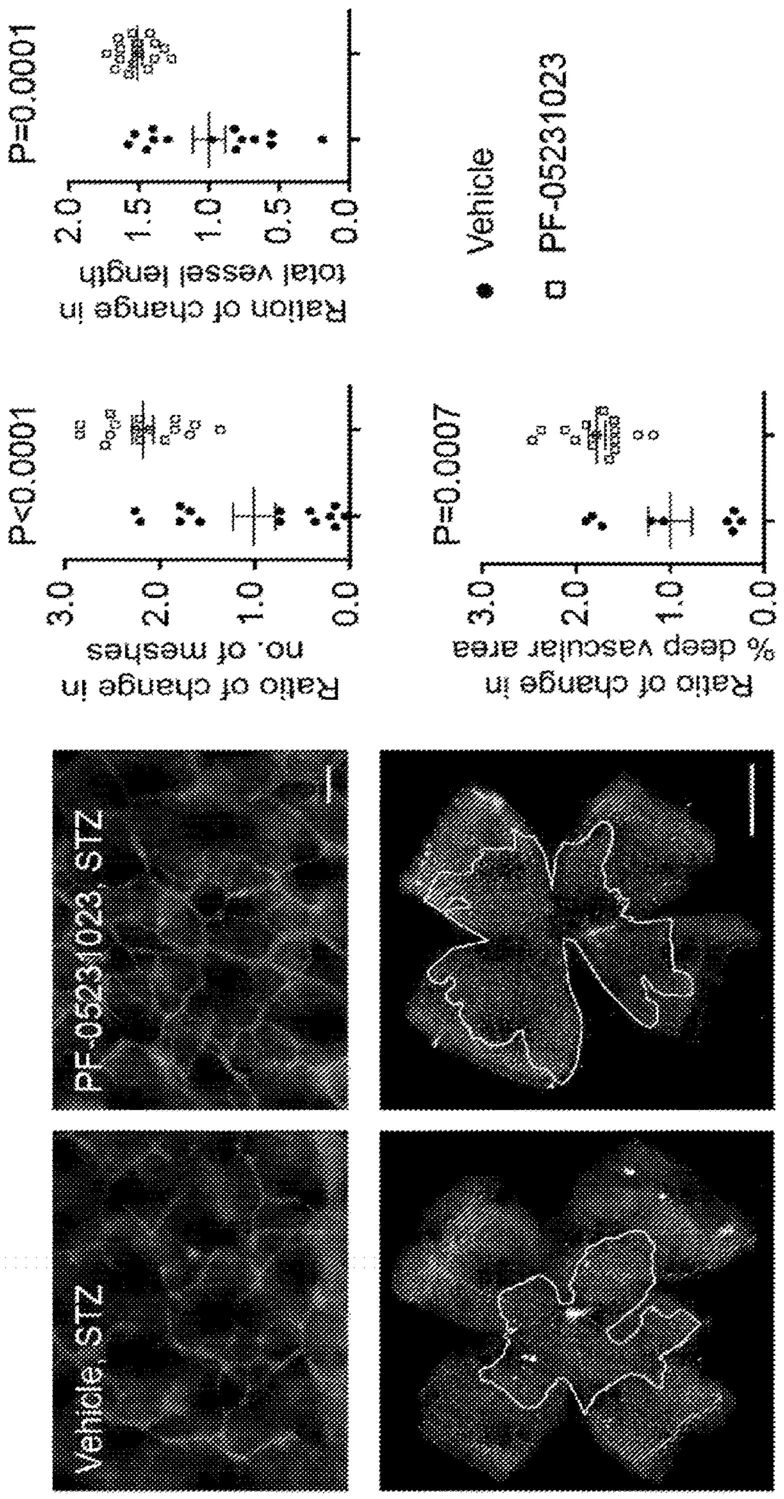

As seen in FIGS. 8A and 8B, FGF21 deficiency delayed normal retinal vascular development (FIG. 12A) and worsened hyperglycemic retinopathy (FIG. 8B) in neonatal mice. As seen in FIGS. 9A and 9B, FGF21 promoted retinal vascular development in hyperglycemic mouse neonates. Both native FGF21 (nFGF21; FIG. 9A) and long-acting FGF21 (PF-05231023, FIG. 9B) administration improved retinal vascular growth. In some embodiments, FGF21 promoted and/or improved retinal vascular growth. In some embodiments, long-acting FGF21 promoted and/or improved retinal vascular growth.

Figure 10A:
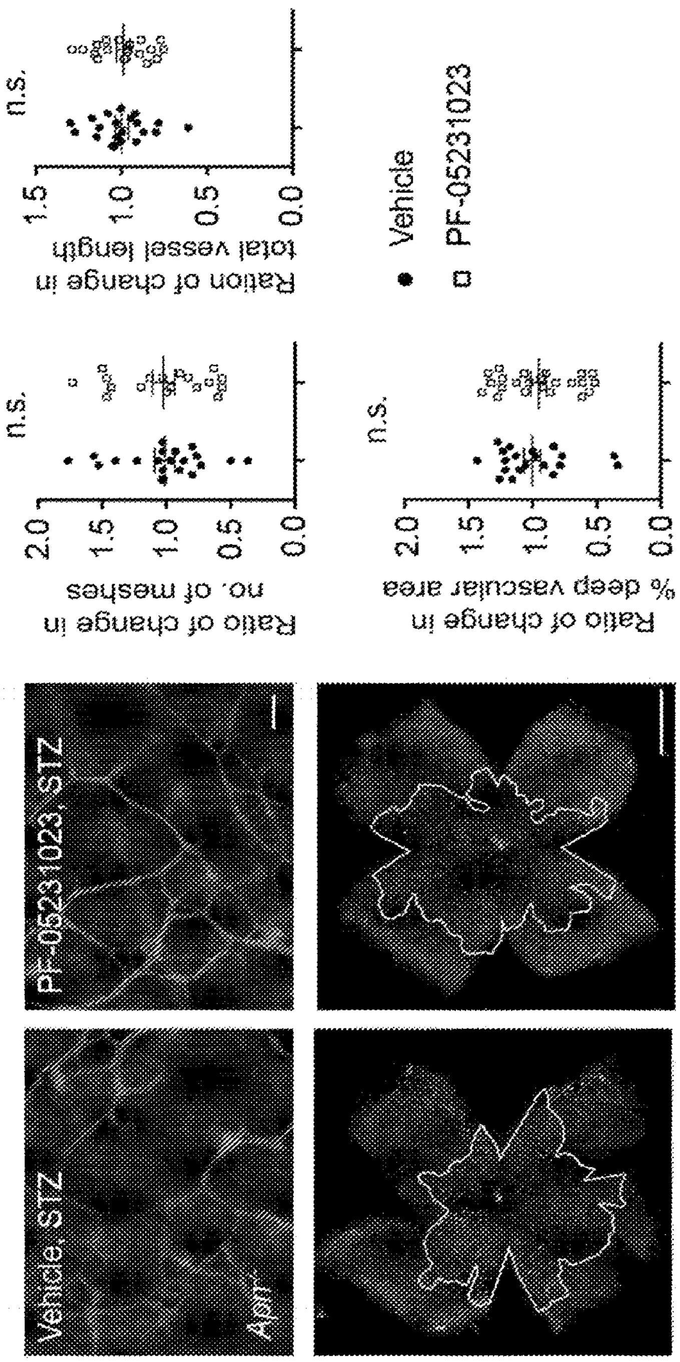
FIGS. 10A-10B depict micrographs and graphs demonstrating that long-acting FGF21 protection against hyperglycemic retinopathy was dependent on adiponectin (APN).
Figure 10B:
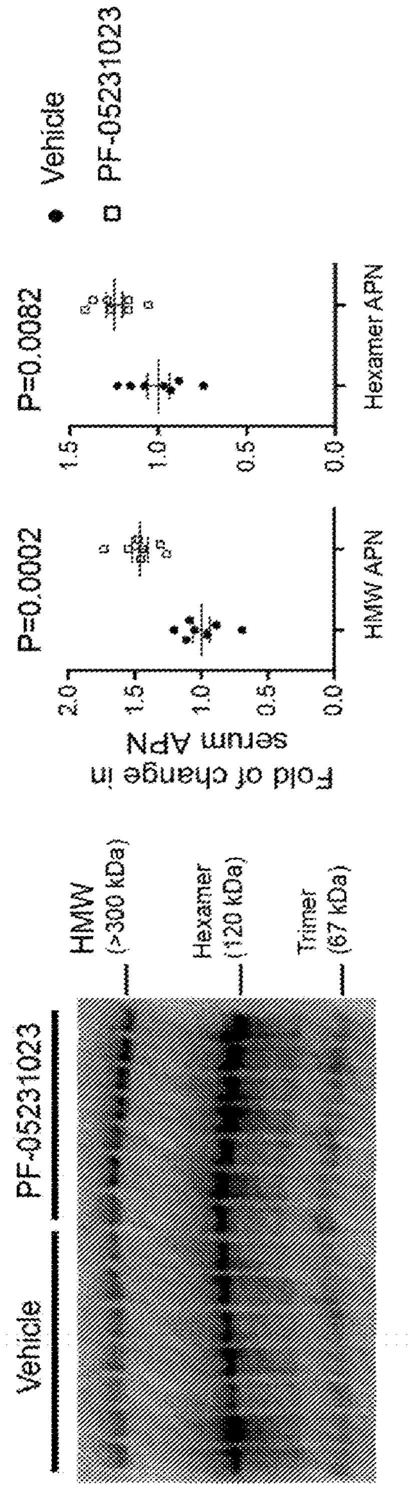

As seen in FIGS. 10A and 10B, FGF21 protection against hyperglycemic retinopathy was dependent on adiponectin (APN). As shown in FIG. 10A, APN deficiency completely abolished FGF21 effects on STZ-induced hyperglycemic retinopathy. As demonstrated in FIG. 10B, FGF21 increased APN levels in serum. In some embodiments, FGF21 therefore prevented and/or reduced retinopathy of prematurity. In certain embodiments, long-acting FGF21 therefore prevented and/or reduced retinopathy of prematurity.

Example 6: Long-Acting FGF21 in Retinitis Pigmentosa (RP)

Figure 11:
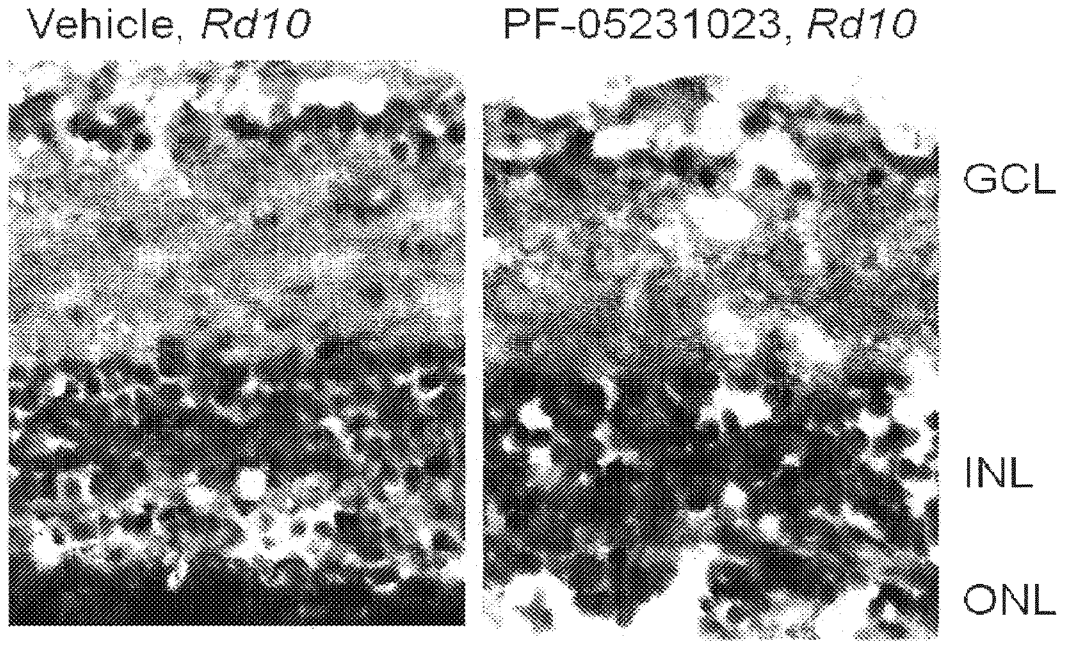
FIG. 11 demonstrates that long-acting FGF21 protection against the decrease in cone function in retinal degenerating mice (Rd10) modeling retinitis pigmentosa.

As seen in FIG. 11, long-acting FGF21 increased the photoreceptor layer thickness (ONL) in photoreceptor-degenerating mice rd10. To determine if FGF21 preserved photoreceptor function, rd10 mice are treated with long-acting FGF21 analog PF-05231023. Retinal histology, retinal function with electroretinogram (ERG), and cone survival with immunohistochemistry are used to assess preservation of photoreceptor function by long-acting FGF21. Retinal mitochondrial function and glycolysis with Seahorse Fx96 oxygen consumption rate (OCR) as well as an extracellular acidification rate (ECAR) analysis are also performed to assess preservation of photoreceptor function by long-acting FGF21. Furthermore, retinal key metabolic enzyme levels (Krebs cycle, glycolysis, fatty acid oxidation) are also performed with quantitative proteomic analysis to assess preservation of photoreceptor function by long-acting FGF21. Finally, mitochondrial function and glycolysis (Seahorse OCR, ECAR analysis) in cone-like photoreceptors (661W) in vitro are also assessed in concert with PF-05231023 treatment.

To determine if FGF21 administration improves retinal vascular development in rd10, as retinal vessels reflect photoreceptor metabolic needs, P30 deep vasculature in retinal whole mount in rd10 vs. control mice with PF-05231023 treatment is quantified. Neovascular growth in laser-captured microdissected retinal layers and vessels in WT and rd10 mice, as well as PF-05231023 versus vehicle-treated rd10 mice are also quantified.

In some embodiments, these analyses and quantifications thereby demonstrate that long-acting FGF21 preserves photoreceptor function. In some embodiments, these analyses and quantifications demonstrate that long-acting FGF21 improves retinal vascular development. Optionally, these analyses and quantifications demonstrate that long-acting FGF21 prevents and/or reduces retinitis pigmentosa in a subject having or at risk of developing RP.

Example 7: FGF21 Protects Against Early Diabetic Retinopathy (DR)

Retinal neuronal abnormalities occur before vascular changes in diabetic retinopathy. Accumulating experimental evidence suggests that neurons control vascular pathology in diabetic and other neovascular retinal disease. Whether fibroblast growth factor 21 (FGF21) prevented retinal neuronal dysfunction in insulin-deficient diabetic mice was investigated.

Materials and Methods

Animals: All animal studies adhered to the Association for Research in Vision and Ophthalmology Statement for the Use of Animals in Ophthalmic and Vision Research and were approved by the Institutional Animal Care and Use Committee at Boston Children's Hospital.

Mouse models of type 1 diabetes—Akita mice: $Ins2^{Akita}$ male mice have a spontaneous mutation in the insulin 2 gene which leads to incorrect folding of insulin protein. Heterozygous Akita mice develop diabetes within one month and retinal complications around 6-months of age (Lai A K, Lo A C. *Journal of Diabetes Research* 2013:106594). 7-to-8-month-old Akita mice were compared with littermate wild-type (WT) mice. Akita mice with retinal functional abnormalities were screened with electroretinography (ERG) and those with ERG changes were intraperitoneally injected with 10 mg/kg long-acting FGF21 analog, PF-05231023 (Pfizer) or vehicle control twice a week for four weeks. Retinal function was again examined with ERG after 4 weeks of treatment and body weight, blood glucose were recorded. Serum triglycerides levels were measured using the Wako L-Type TG M test.

Streptozotocin (STZ)-induced diabetic mice: 6-to-8-week-old male WT and adiponectin-deficient ($Apn^{-/-}$) mice were starved six hours prior to an intraperitoneal injection of 55 mg/kg/day STZ on day 1 and 2 followed by an injection of 60 mg/kg/day STZ from day 3 to 5. Diabetes was induced within one week of injection (Lai A K et al. 2013). 7-to-8-month-old diabetic WT and $Apn^{-/-}$ mice were screened with ERG. Mice with retinal functional abnormalities were intraperitoneally injected with 10 mg/kg PF-05231023 or control twice a week for four weeks. Retinal function was then re-examined with ERG.

Electroretinography (ERG): ERG was used to assess the function of retinal neurons. Flash ERGs were obtained using an Espion $e^2$ (Diagnosys LLC, Lowell, Mass.) in dark-adapted, mydriatic (Cyclomydril; Alcon, Fort Worth, Tex.), anesthetized (ketamine/xylazine) subjects. Stimuli were "green" light emitting diode flashes of doubling intensity from ~0.0064 to ~2.05 cd·s/$m^2$ and then "white" xenon-arc flashes from ~8.2 to ~1,050 cd·s/$m^2$ presented in an integrating sphere (Colordome, Diagnosys LLC). As shown (FIG. 14A), the saturating amplitude ($Rm_{P3}$) and sensitivity (S) of the rod photoreceptors was estimated from the a-waves elicited by the white flashes (Lamb T D, Pugh E N, Jr., *J Physiol* 1992; 449:719-758). The saturating amplitude ($Rm_{P2}$) and sensitivity ($1/K_{P2}$) of second-order neurons, principally bipolar cells (Wurziger K, et al., *Vision Res* 2001; 41:1091-1101), was measured by subtracting this model from the intact ERG waveform (Robson J G, et al., *Vis Neurosci* 1995; 12:837-850) and fitting the Naka-Rushton equation (Fulton A B, Rushton W A. *Vision Research* 1978; 18:793-800) to the response vs. intensity relationship of the resulting waveform, "P2." The oscillatory potentials (OPs), which characterize activity in inner retinal cells distinct from the generators of the a- and b-waves (Dong C J, et al., *Vis Neurosci* 2004; 21:533-543), were filtered from P2 (Lei B, et al., *Invest Ophthalmol Vis Sci* 2006; 47:2732-2738) and assessed in the frequency domain to determine their energy (Akula J D, et al., *Invest Ophthalmol Vis Sci* 2007; 48:5788-5797); the saturating energy (Em) and sensitivity ($1/i_{1/2}$) of the OPs were then assessed similarly to those of P2. Finally, retinal sensitivity at threshold (Sm), was calculated by scaling the amplitude of each P2 by the intensity used to elicit it and fitting a generalized logistic growth curve, with the exponent set to negative unity, to the resulting sensitivities, and determining the limit of this function as intensity approached zero (Akula J D, et al., *Mol Vis* 2008; 14:2499-2508).

Optical coherence tomography (OCT): Mice were anesthetized (ketamine/xylazine), and their pupils dilated (Cyclomydril; Alcon, Fort Worth, Tex.). Spectral domain OCT with guidance of bright-field live fundus image was performed with the image-guided OCT system (Micron IV, Phoenix Research Laboratories). Photoreceptor inner and outer segment thickness was measured using Insight (provided by Micron IV). The thickness of photoreceptor segments was plotted at six distances (50, 100, 150, 200, 250 and 300 μm) from the optic nerve head both on the nasal and on the temporal side.

Immunohistochemistry: For IHC on retinal cross-sections, eyes were fixed in 4% PFA, frozen in optimal cutting temperature compound (OCT, Tissue-Tek) and then were cut into 10-μm sections and rinsed with PBS. The sections with optic nerve were treated with ice-cold methanol for 15 minutes and then 0.1% triton PBS for 45 minutes at room temperature. The sections were blocked with 3% bovine serum albumin (BSA) for 1 hour at room temperature and stained with primary antibody against cone arrestin (1:500, AB15282, Millipore), rhodopsin (1:500, MABN15, Millipore) overnight at 4° C. The sections were stained with corresponding secondary antibody, covered in mounting medium with 4',6-Diamidine-2'-phenylindole dihydrochloride (DAPI, H-1200, Vector laboratories), and visualized with a Leica SP2 confocal microscope or a Zeiss AxioObserver.Z1 microscope at 200× magnification.

Laser-captured microdissection: Fresh mouse eyes were embedded in OCT compound and sectioned at 12 μm in a cryostat, mounted on RNase-free polyethylene naphthalate glass slides (11505189, Leica). Frozen sections were fixed in 70% ethanol for 15 seconds, followed by 30 seconds in 80% ethanol and 30 seconds in absolute ethanol, and then washed with DEPC-treated water for 15 seconds. Laser-dissection of retinal neuronal layers was performed immediately thereafter with the Leica LMD 6000 system (Leica Microsystems) and samples were collected directly into lysis buffer from the RNeasy Micro kit (Qiagen, Chatsworth, Calif.).

Photoreceptors (661W) cell culture: Photoreceptor 661W cells were cultured at 37° Celsius, 5% $CO_2$ in a humidified atmosphere in Dulbecco's modified Eagle's medium (DMEM, #1196502, Gibco) supplemented with 10% fetal bovine serum (#S12450, Atlanta Biologicals) and 1% antibiotic/antimycotic solution. An equal number of cells per well was plated on a 6-well dish. Oxidative stress was induced with 0.5 mM paraquat (PQ, Sigma, #856177) for 1 hour at 37° Celsius. The culture media were changed and the cells were treated with vehicle (PBS) or 500 ng/ml PF-05231023 for 24 hours. Cells were collected for protein and RNA.

Real-time PCR: Retinas or 661W cells were lysed with QIAzol lysis reagent and incubated on ice for 15 minutes.

20% chloroform was added and incubated for 5 minutes at room temperature. RNA was extracted according to the manufacturer's instructions using a PureLink® RNA Mini Kit (#12183018A, Ambion). RNA was then reverse transcribed using iScript™ cDNA synthesis kit (#1708891, Bio-Rad). qPCR were performed for Arrestin4: 5'-GAG CAA GGG CTG CTA CTC AAG-3' (SEQ ID NO: 32), 5'-AAC CGC AGG TTC AAG TAT TCC-3' (SEQ ID NO: 33); Rhodopsin: 5'-TCA TGG TCT TCG GAG GAT TCA C-3' (SEQ ID NO: 34), 5'-TCA CCT CCA AGT GTG GCA AAG-3' (SEQ ID NO: 35); IL-1β: 5'-TTC AGG CAG GCA GTA TCA CTC-3' (SEQ ID NO: 36), 5'-GAA GGT CCA CGG GAA AGA CAC-3' (SEQ ID NO: 37); IL-6: 5'-AAG AGC CGG AAA TCC ACG AAA-3' (SEQ ID NO: 38), 5'-GTC TCA AAA GGG TCA GGG TAC T-3' (SEQ ID NO: 39); Vegfa F: 5'-GGA GAT CCT TCG AGG AGC ACT T-3' (SEQ ID NO: 24), R: 5'-GCG ATT TAG CAG CAG ATA TAA GAA-3' (SEQ ID NO: 25); Tnfα 5'-AAG GAC CTG GTA CAT GAA CTG G-3' (SEQ ID NO: 26), 5'-GGT TCT GGG TGT CAA GTG TCG-3' (SEQ ID NO: 27); IL-10: 5'-CTT ACT GAC TGG CAT GAG GAT CA-3' (SEQ ID NO: 40), 5'-GCA GCT CTA GG AGC ATG TGG-3' (SEQ ID NO: 41); Apn: 5'-GAAGCCGCTTATGTGTATCGC-3' (SEQ ID NO: 42), 5'-GAATGGGTACATTGGGAACAGT-3' (SEQ ID NO: 43); Nrf2: 5'-TAG ATG ACC ATG AGT CGC TTG C-3' (SEQ ID NO: 44), 5'-GCC AAA CTT GCT CCA TGT CC-3' (SEQ ID NO: 45); Nfκb: F: 5'-GGA GAG TCT GAC TCT CCC TGA GAA-3' (SEQ ID NO: 46), R: 5'-CGA TGG GTT CCG TCT TGG T-3' (SEQ ID NO: 47). Quantitative analysis of gene expression was generated using an Applied Biosystems 7300 Sequence Detection System with the SYBR Green Master mix kit and gene expression was calculated relative to Cyclophilin A ((5'-CAG ACG CCA CTG TCG CTT T-3' (SEQ ID NO: 30); 5'-TGT CTT TGG AAC TTT GTC TGC AA-3'(SEQ ID NO: 31)) (retinas) or β-actin ((5'-CGG TTC CGA TGC CCT GAG GCT CTT-3' (SEQ ID NO: 48), 5'-CGT CAC ACT TCA TGA TGG AAT TGA-3' (SEQ ID NO: 49)) (photoreceptor 661W cells) using the ΔΔCt method. Each sample was repeated in triplicate.

Western blot: *protein lysate from photoreceptor 661W cells were used to detect the levels of NRF2 (1:500, R&D, MAB3925), phospho-NFκB (1:200, Cell Signaling, #3037S), NFκB (1:1000, Cell Signaling, #3034), p-AKT (1:500, Cell Signaling, #9271), AKT (1:1000, Cell Signaling, #4691) in 5% bovine serum albumin (BSA) overnight at 4° Celsius degree. Signals were detected using 1:5000 corresponding horseradish peroxidase-conjugated secondary antibodies and enhanced chemiluminescence (ECL, Pierce), then the digital images were visualized with Bio-Rad ChemiDoc Touch Imaging System. β-ACTIN (1:5000, Sigma; A1978) was used as internal control.

Statistical analysis: All ERG data were presented as the log change from control (Δ Log Normal); by expressing the data in log values, changes in observations of fixed proportion become linear, consistent with a constant fraction for physiologically meaningful changes in parameter values (Akula J D, et al., *Mol Vis* 2008; 14:2499-2508). Δ Log Normal ERG data were plotted as mean±SEM and evaluated for significant effects using mixed-effects linear models (MLMs) (Fitzmaurice G M, Laird N M, Ware J H: Applied longitudinal analysis. Hoboken, N.J., Wiley, 2011). In each analysis, two MLMs were employed. The first MLM, carried out on the saturating a-wave, P2 and OP parameters, had factors group (Akita vs. WT; or STZ vs. Control), treatment (before vs. after PF-05231023), parameter (Amplitude vs. Sensitivity), and retinal depth (photoreceptor vs. bipolar vs. inner retina). The second MLM, carried out on Sm, had factors group, and treatment. Data from both eyes was included in all analyses. Differences in ERG parameters were detected by ANOVA followed by Tukey's test. Two-tailed unpaired t-test, ANOVA with Bonferroni's multiple comparison test was used for comparison of results as specified (Prism v5.0; GraphPad Software, Inc., San Diego, Calif.). The threshold for statistical significance (α) was set at 0.05.

Results

Figure 13A:
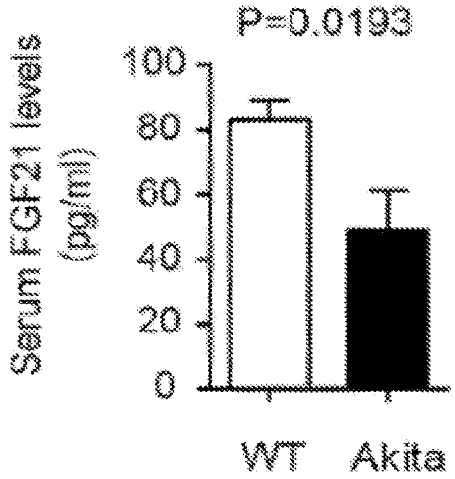
FIGS. 13A-13D depict graphs showing that serum FGF21 levels were decreased in Akita mice.
Figure 13B:
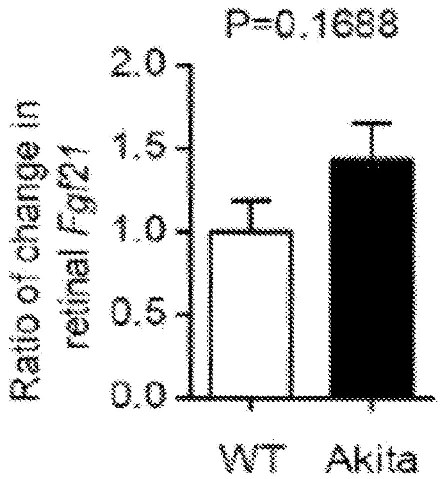
Figure 13C:
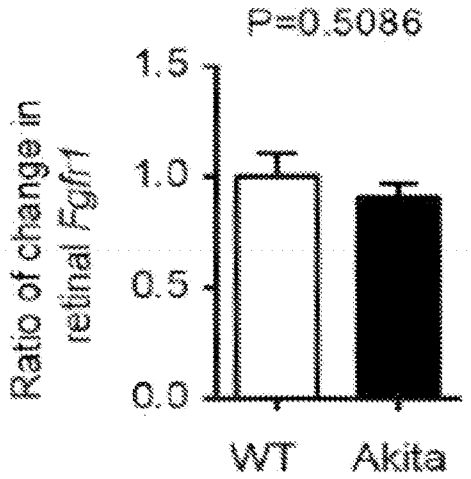
Figure 13D:
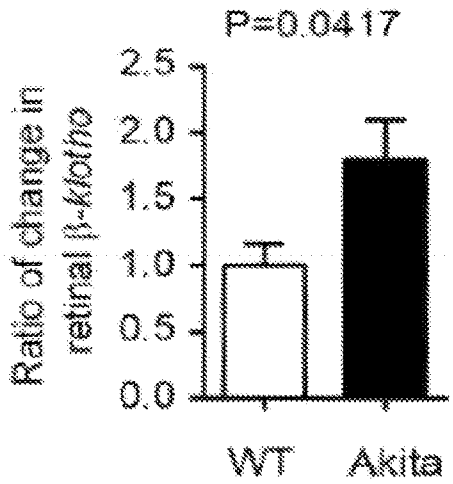
Figure 20:
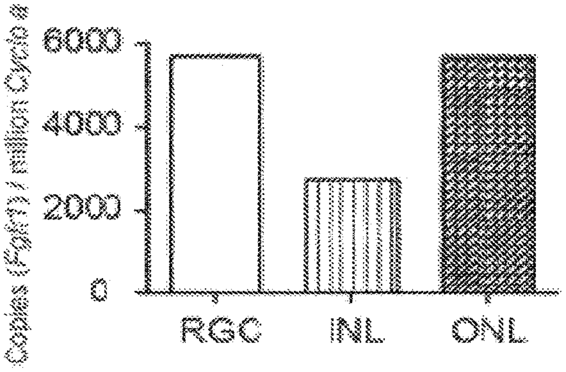
FIG. 20 depicts a graph showing FGF21 receptor Fgfr1 expression in retinal neuronal layers. RGC (retinal ganglion cells), INL (inner nuclear layer), and ONL (outer nuclear layer) were isolated using laser-captured microdissection and RNA was extracted. qPCR of Fgfr1 was conducted.
Figure 21A:
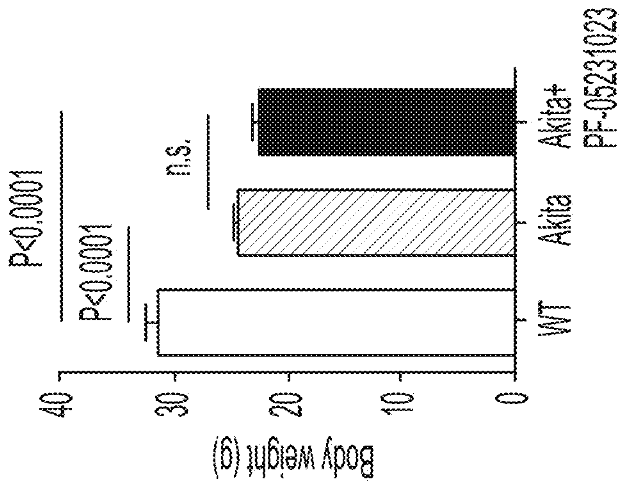
FIGS. 21A-21C depict graphs showing that PF-05231023 administration did not change body weight (FIG. 21A), blood glucose levels (FIG. 21B) or serum triglycerides (FIG. 21C) in Akita mice. Body weight was decreased, blood glucose levels and serum triglyceride (TG) levels were induced in diabetic Akita mice versus normal WT mice; PF-05231023 administration lowered blood glucose levels, but did not change the body weight and serum TG levels in Akita mice. Data is presented as Mean±SEM. n=5-12 mice per group. ANOVA followed by Bonferroni's multiple comparisons test. n.s., no significance.
Figure 21B:
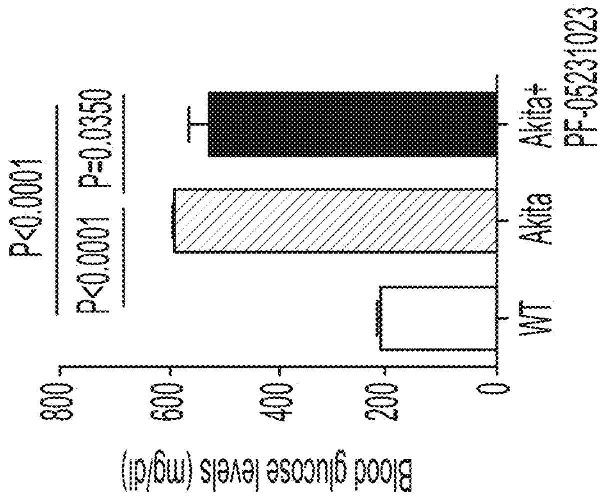
Figure 21C:
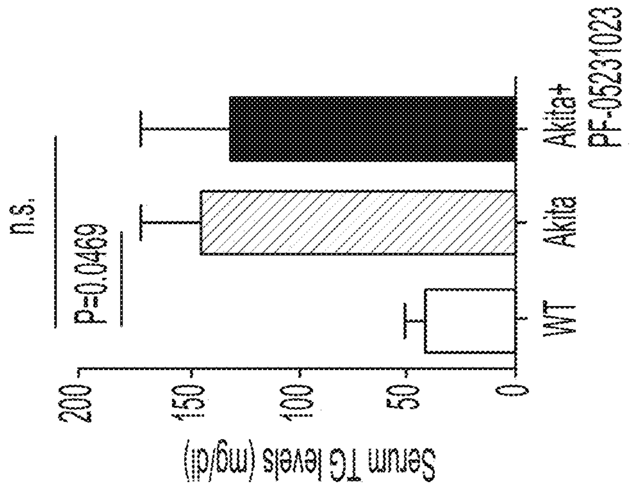

PF-05231023 administration restored retinal function in Akita mice: Circulating FGF21 levels (ELISA) were reduced in >7 month old Akita mice versus littermate wild-type (WT) control mice (FIG. 13A). Retinal expression of Fgf21 (qPCR) was not changed significantly (FIG. 13B). The physiologic and pharmacologic actions of FGF21 are dependent on the receptor FGFR1 and co-receptor β-klotho (Foltz I N, et al., *Science Translational Medicine* 2012; 4:162ra153; Ding X, et al., *Cell Metabolism* 2012; 16:387-393). Gene expression of FGF21 receptor Fgfr1 was comparable and β-klotho was mildly increased in Akita versus WT mouse retinas (FIGS. 13C-13D) (Foltz I N, et al., *Science Translational Medicine* 2012; 4:162ra153; Ding X, et al., *Cell Metabolism* 2012; 16:387-393). Fgfr1 was expressed in retinal neurons isolated from retinal cross sections with laser-captured microdissection (FIG. 20).

Figure 14A:
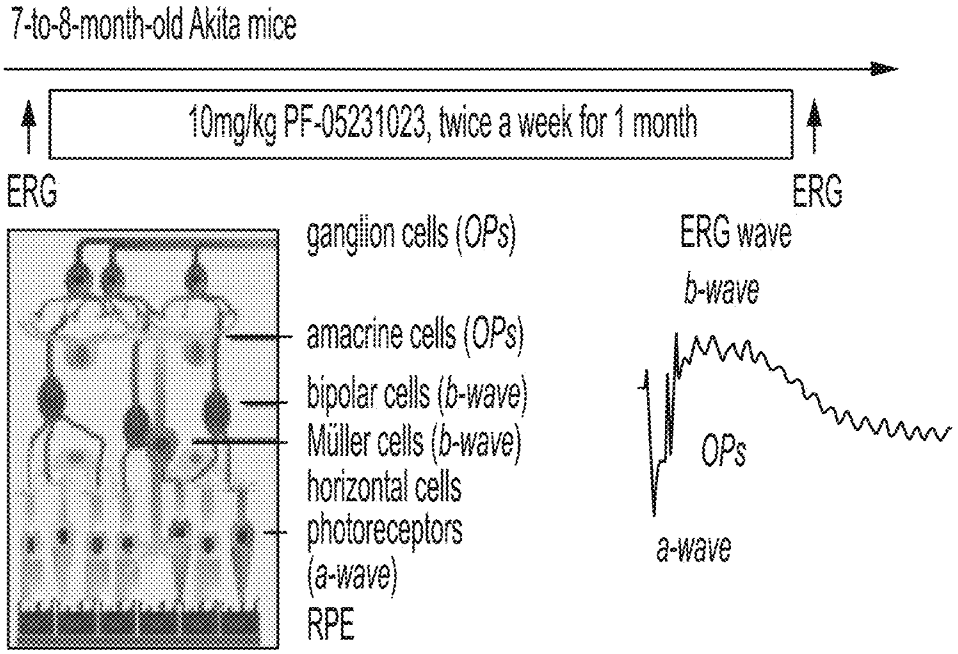
FIGS. 14A-14E depict a series of schematic illustrations and graphs showing that PF-05231023 administration improved retinal function in diabetic Akita mice.
Figure 14B:
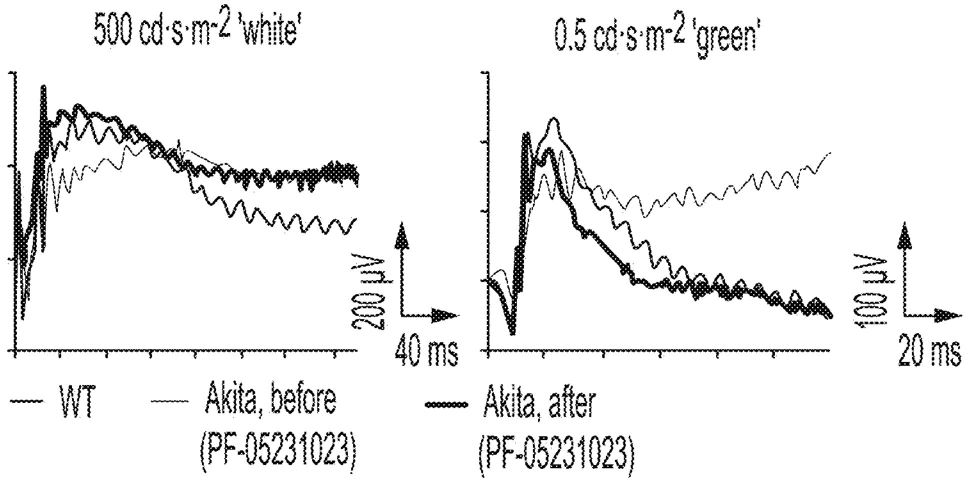
Figure 14C:
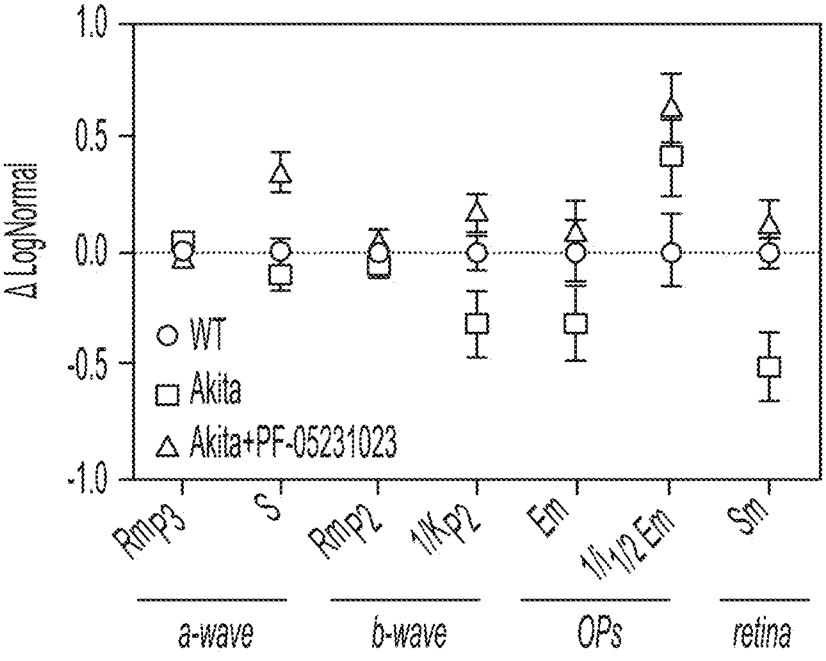
Figure 14D:
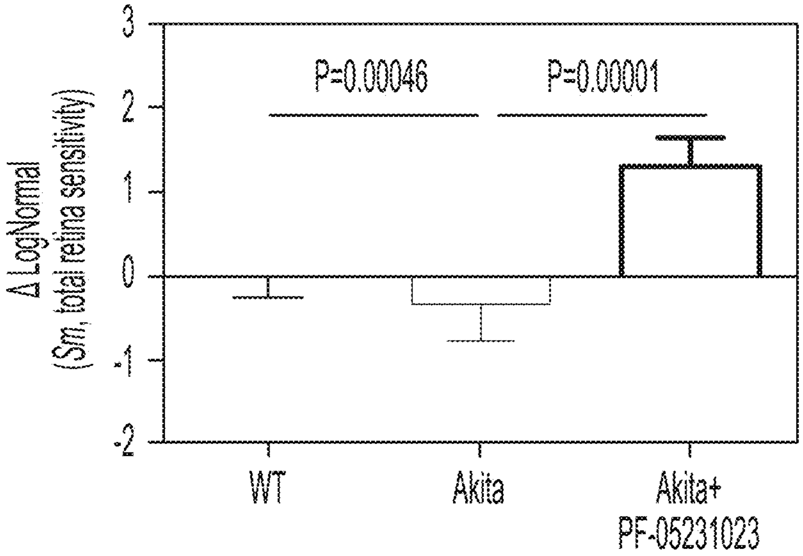
Figure 14E:
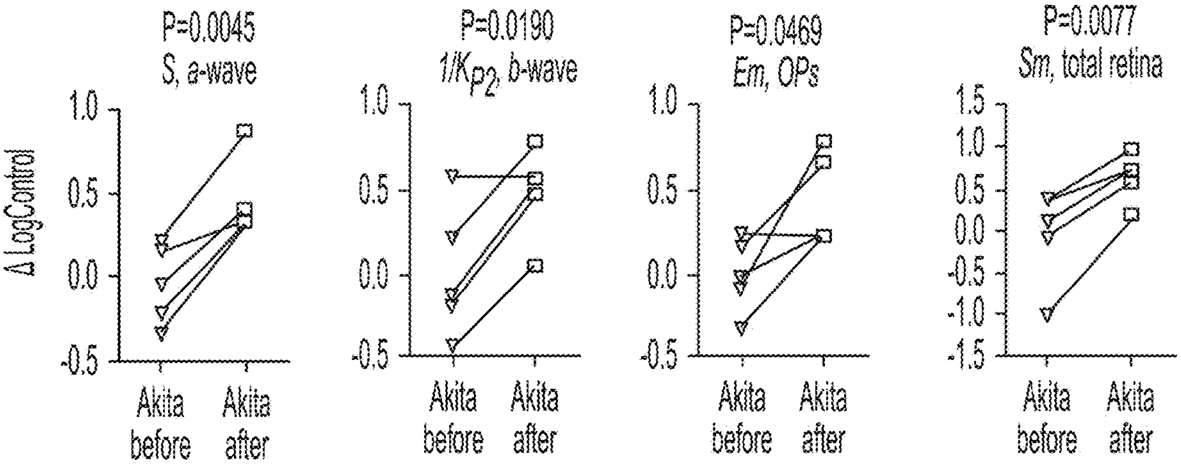
Figure 15A:
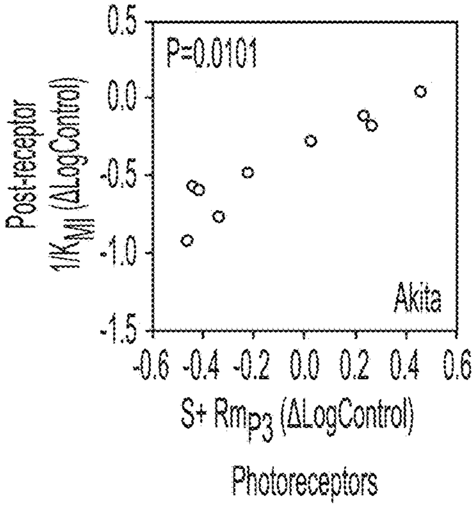
FIGS. 15A-15E depict a series of plots photographs and graphs showing that PF-05231023 administration restored the retinal morphology in Akita mice.
Figure 22:
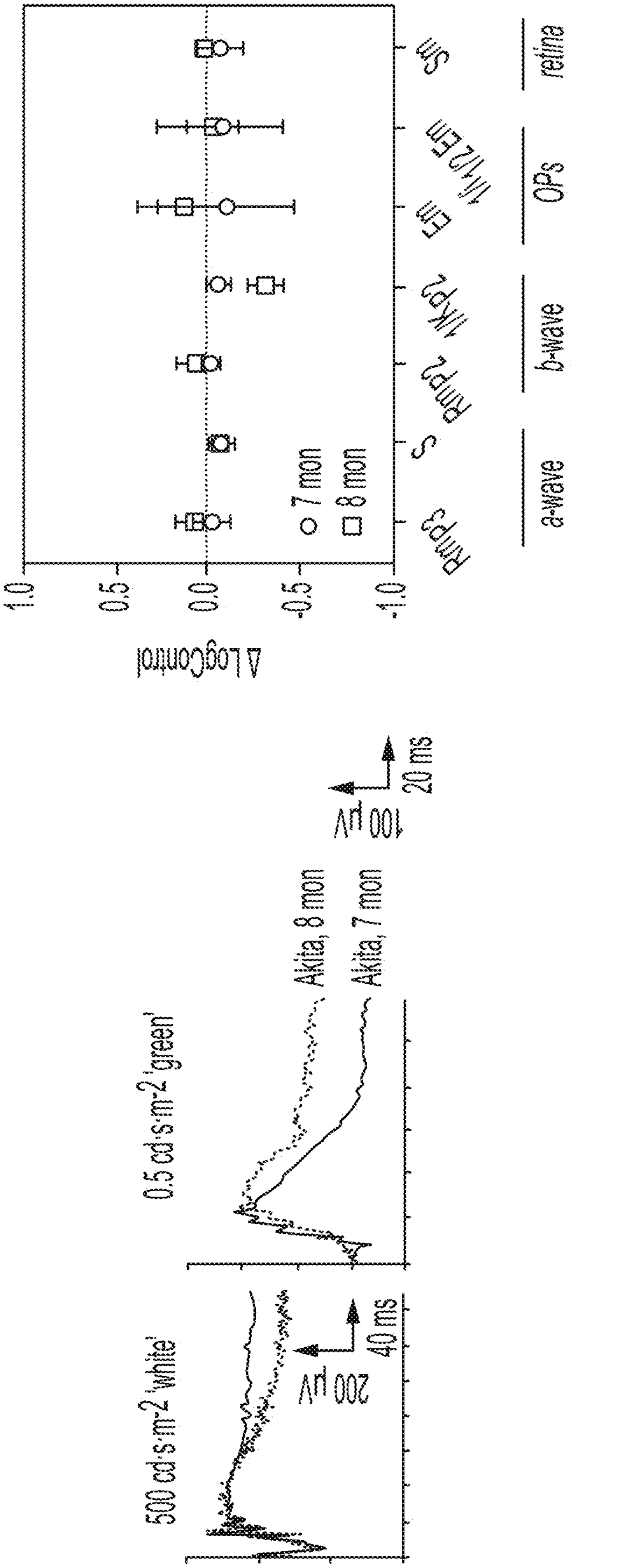
FIG. 22 is a series of plots and Comparison of ERG parameters in Akita mice measured at 7-month and 8-months of age. n=3 mice per group. ANOVA followed by Tukey's test. Representative ERG plot is shown. Data was presented as Mean±SEM.

To examine if FGF21 protects against retinal dysfunction in DR, PF-05231023 (10 mg/kg intraperitoneally was first administered, twice a week for a month) or vehicle control to those Akita mice which had ERG deficits at 7-8-month of age (50% of Akita mice (6/12) had ERG deficits versus their age-matched WT control mice). In Akita mice with ERG deficits, PF-05231023 administration did not change the body weight and serum triglyceride levels versus controls but mildly reduced blood glucose levels (FIGS. 14A-14C). Prior to PF-05231023 treatment, ERG responses were examined in Akita mice. Although the Akita mouse responses were slightly attenuated overall compared to WT controls (FIGS. 14A-14C), retinal sensitivity (Sm), as determined by mixed-linear modeling, was significantly attenuated ($F=15.9$; $df=1, 27.0$; $p=0.00046$) relative to WT. PF-05231023 showed protective effects on Akita retinas (FIGS. 14B-14C). Notably, retinal sensitivity (Sm) in Akita mice was improved following treatment (FIG. 14D) ($F=27.9$, $df=1, 29.8$, $p=1.1\times10^{-5}$) to levels that were supranormal, a result of better a-wave (S) and b-wave ($1/K_{P2}$) sensitivities (FIG. 14E). There was no decline in baseline retinal function (ERG signals) in any individual mouse between 7 and 8 months of age ($F=0.166$, $df=1, 2$, $p=0.723$, FIG. 22). In Akita mice, the change in post-receptor sensitivity ($\log 1/K_{P2}$) was positively correlated with the sum of changes in photoreceptor sensitivity and saturated amplitudes ($\log S+\log Rm_{P3}$, a-wave) (FIG. 15A), providing evidence that the changes in post-receptor cells were reflecting the deficits in photoreceptor function (Hansen R M, et al., Progress in Retinal and Eye Research 2017; 56:32-57; Hood D C, et al., *Visual Neuroscience* 1992; 8:107-126).

Figure 15B:
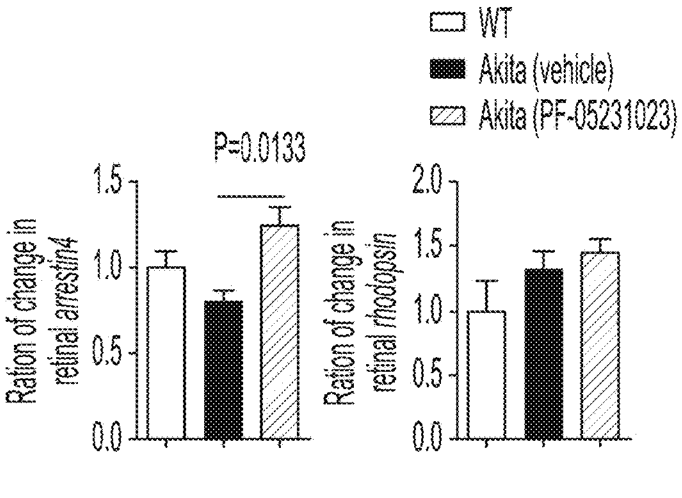
Figure 15C:
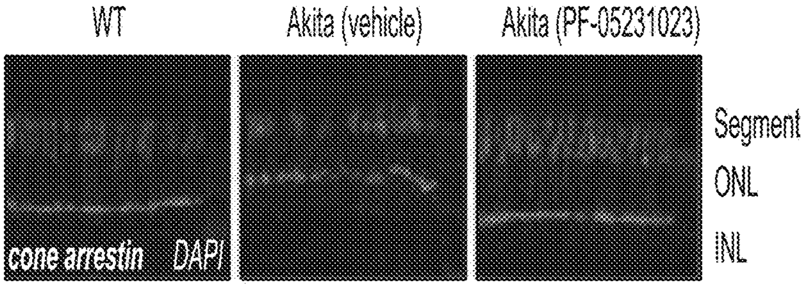
Figure 15D:
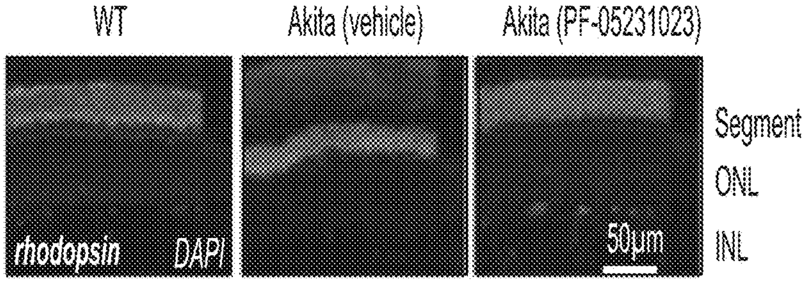
Figure 15E:
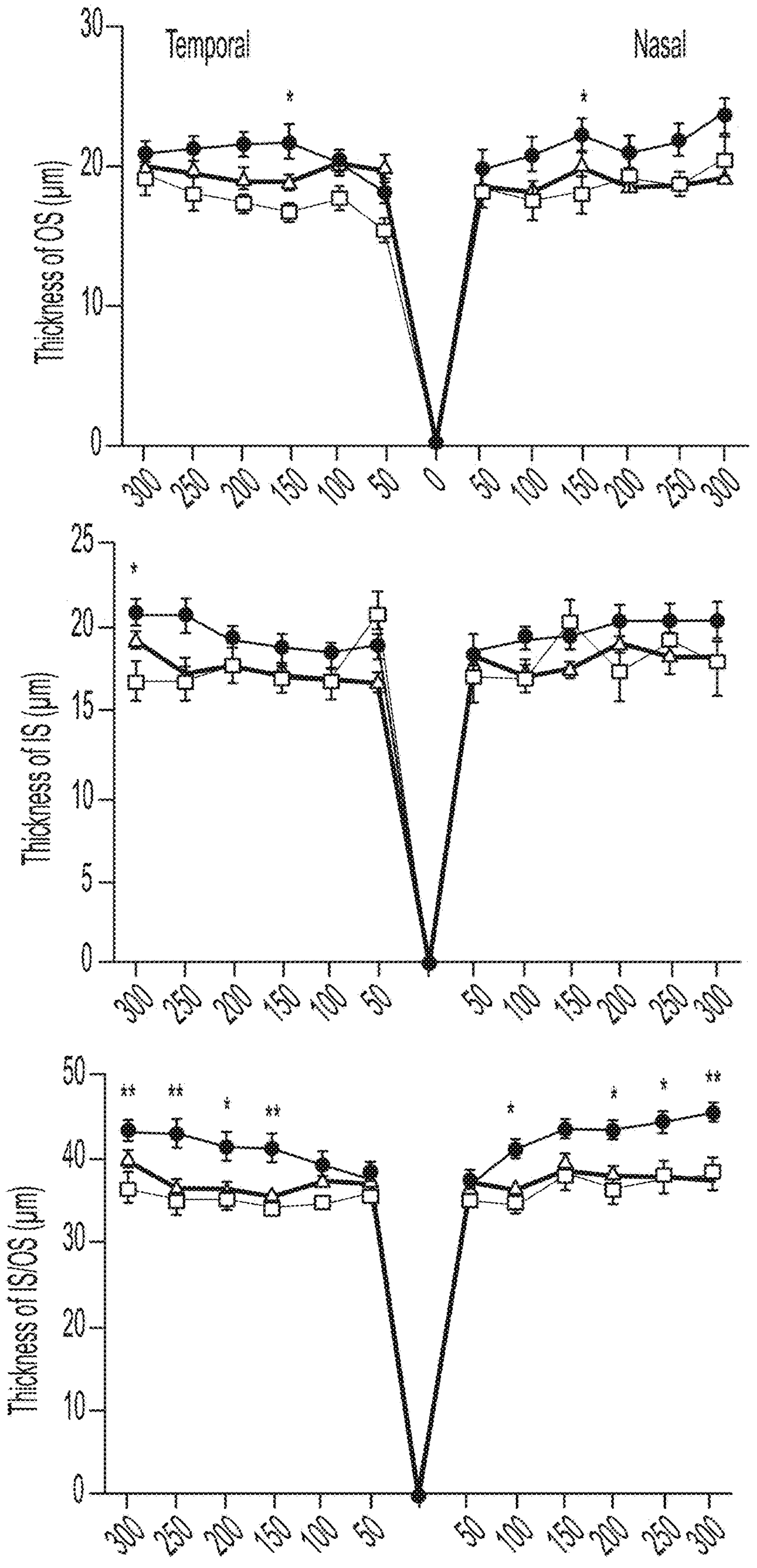

PF-05231023 administration restored photoreceptor morphology in Akita mice: In addition to neuronal function, cone and rod photoreceptor structure was examined to determine if it was influenced by PF-05231023 administration. PF-05231023 administration increased cone-specific arrestin4 expression (Craft C M, et al., *The Journal of Biological Chemistry* 1994; 269:4613-4619) and did not change rhodopsin expression at the mRNA levels in Akita mice (FIG. 15B). Cone photoreceptor outer and inner segments were oriented in parallel in WT mice but disorganized in Akita mice. PF-05231023 administration normalized the photoreceptor segment arrangement (FIG. 15C). Rhodopsin staining was comparable between WT and PF-05231023-treated Akita mouse retinas, while there appeared to be a reduction in the thickness of rod photoreceptor segments in Akita mice (FIG. 15D). With OCT measurements, there was a significant reduction in the total thickness of photoreceptor inner and outer segment in Akita (blue line) versus WT (black line) mice, but the inner and outer segment thickness was restored with PF-05231023 administration (orange line), particularly the photoreceptor outer segments (FIG. 15E). These observations provide evidence that PF-05231023 protection against DR is through the restoration of photoreceptor function and structure. The possibility of the contribution from other retinal cells was not excluded as Fgfr1 is also expressed in INL and RGC (FIG. 20).

Figure 16A:
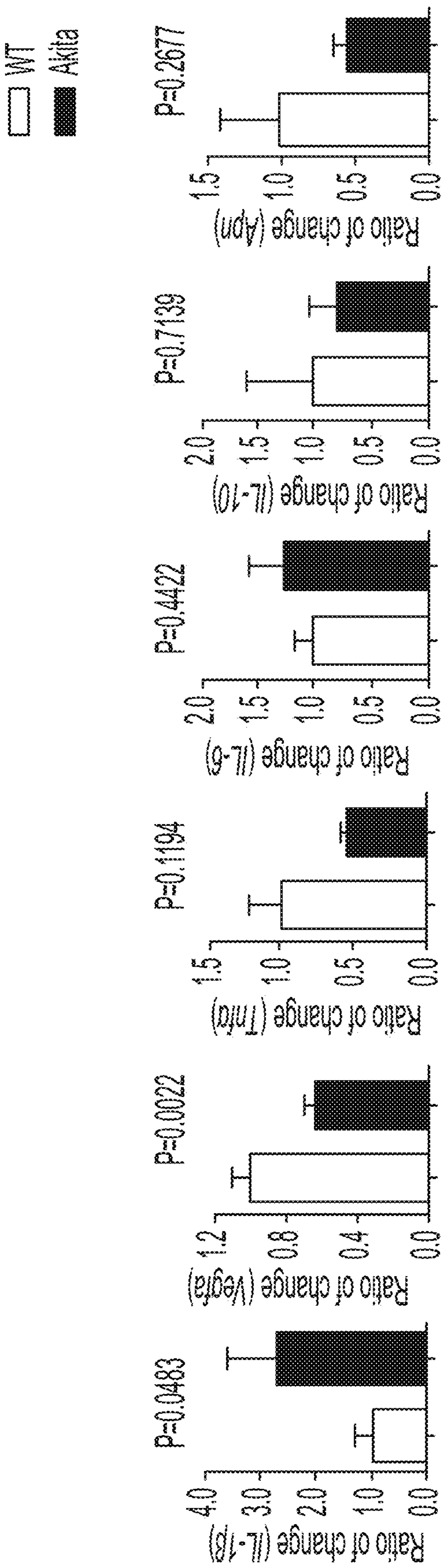
FIGS. 16A-16B depict graphs showing that PF-05231023 administration decreased IL-1β expression in diabetic retinas.
Figure 16B:
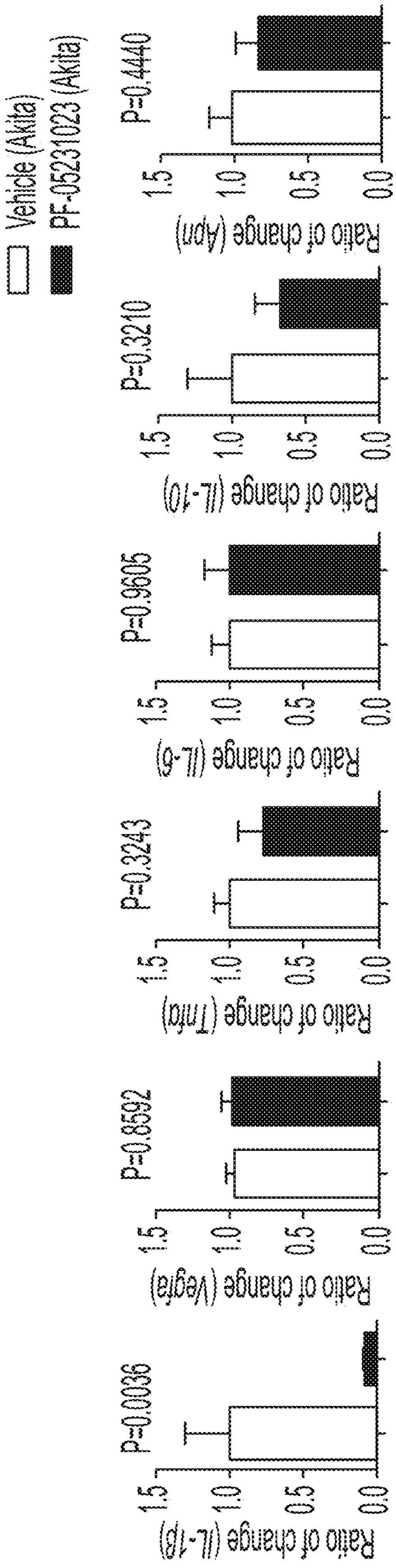

PF-05231023 decreased retinal inflammation in diabetic mice: Retinal inflammation induces retinal neurovascular abnormalities in diabetes (Du Y, et al., *Proc. Nat'l. Acad. Sci. USA* 2013; 110:16586-16591; Liu H, et al., *Inv. Ophthal. & Vis. Sci.* 2016; 57:4272-4281; Tonade D. et al., *Invest. Ophthal. & Vis. Sci.* 2016; 57:4264-4271; Joussen A M, et al., *FASEB J.* 2004; 18:1450-1452). Significantly increased retinal IL-1β and decreased Vegfa mRNA expression was observed in Akita versus WT mice (FIG. 16A). PF-05231023 administration reduced retinal IL-1β mRNA expression in Akita mice (FIG. 16B). IL-1β inhibits energy production in retinal neurons and induces retinal microvascular changes in rats. PF-05231023 administration did not change the expression levels of Vegfa, Tnfα, IL-6, IL-10 and Apn in Akita mouse retinas (FIG. 16B).

Figure 17A:
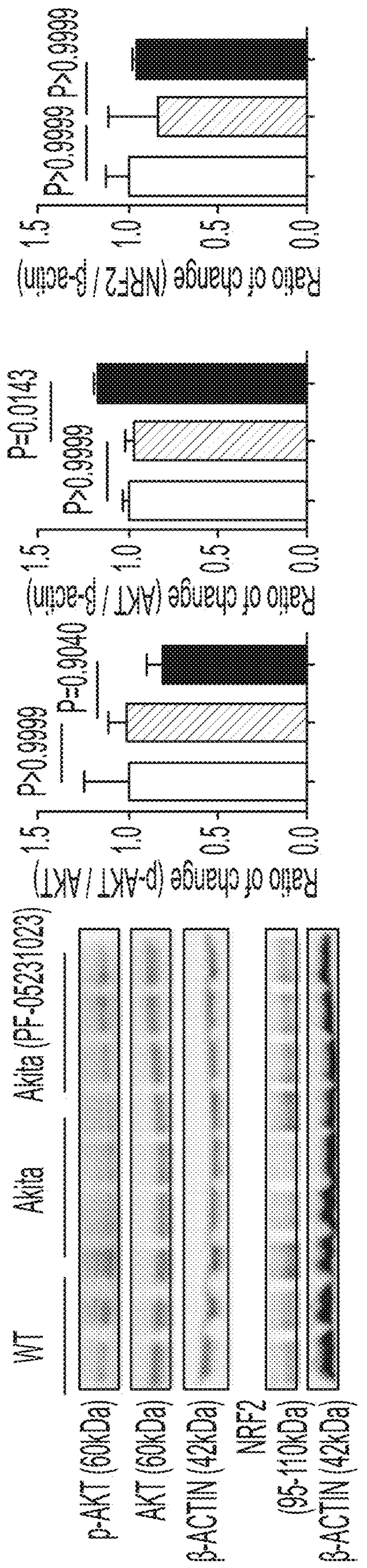
FIGS. 17A-17E depict a series of graphs and photographs of Western blots showing that PF-05231023 administration induced NRF2 levels by activating the AKT pathway and decreased photoreceptor-derived IL-1β.
Figures 17B, 17C, 17D, 17E:
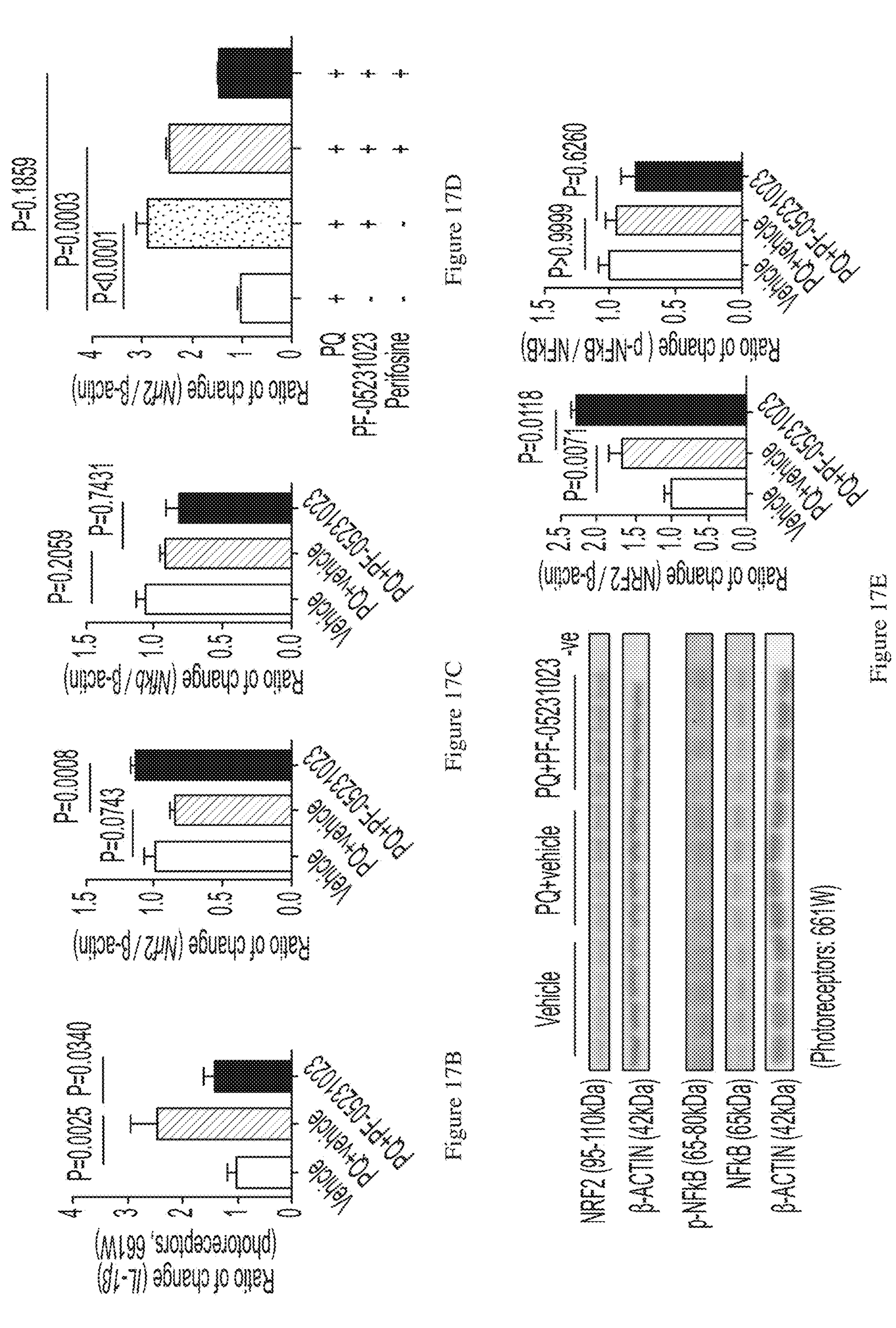

PF-05231023 inhibited oxidative-stress-induced inflammation in photoreceptors: Hyperglycemia induces oxidative stress, a crucial contributor to diabetic retinopathy (Madsen-Bouterse S A, Kowluru R A. *Reviews in Endocrine & Metabolic Disorders* 2008; 9:315-327). Photoreceptors are the most metabolically active cell in the body and very susceptible to metabolic derangement and resulting oxidative stress (Kern T S, Berkowitz B A. *J. Diabetes Invest.* 2015; 6:371-380). Modulating photoreceptor oxidative stress protects against retinal neurodegeneration (Xiong W, et al., *J. Clin. Invest.* 2015; 125:1433-1445). In PF-05231023—versus vehicle-treated Akita mouse retinas, there was a significant increase in total AKT levels although there was no significant change in the ratio of p-AKT/AKT (FIG. 17A), evidencing that the absolute level of p-AKT was higher in PF-05231023-treated mouse retinas. Activation of the AKT pathway regulates NRF2 activity in retinal pigment epithelium in vitro (Wang L, et al., *Invest. Ophthal. & Vis. Sci.* 2008; 49:1671-1678). There was a large variation of NRF2 protein levels in Akita versus WT mice. PF-05231023 administration decreased the variability of retinal NRF2 levels in Akita (FIG. 17A). Taken together, the results provide evidence that PF-05231023 modulates retinal NRF2 levels by activating the AKT pathway. To test if PF-05231023 protects photoreceptors against oxidative stress, oxidative stress was induced with the use of paraquat (PQ), a nonselective herbicide to induce the production of reactive oxygen species in mitochondria (McCarthy S, et al., *Toxicol. Applied Pharma.* 2004; 201:21-31). In 661W cells (the only photoreceptor cell line available currently) in vitro, oxidative stress induced with PQ increased IL-1β expression; PF-05231023 treatment prevented IL-1β induction (FIG. 17B). Both the activation of antioxidant transcriptional factor NRF2 and the phosphorylation of NFκB modulate IL-1β transcription, which can be modulated by FGF21 (Yu Y, et al., *International Immunopharmacology* 2016; 38:144-152; Kobayashi E H, et al., *Nature Communications* 2016; 7:11624; Cogswell J P, et al., *J Immunol* 1994; 153:712-723). PF-05231023 treatment increased gene expression of Nrf2 but not Nfκb in 661W (FIG. 17C). In PQ (to induce oxidative stress)-treated 661W cells, the induction of NRF2 expression by PF-05231023 was dose-dependently inhibited by perifosine, an AKT inhibitor (Zitzmann K, et al., *Endocrine-Related Cancer* 2012; 19:423-434) (FIG. 17D). PF-05231023 treatment also increased NRF2 production at the protein level but did not change NFκB phosphorylation in photoreceptors with PQ-induced oxidative stress (FIG. 17E), providing evidence that FGF21 inhibition of IL-1β was through activation of the NRF2 pathway.

Figure 18A:
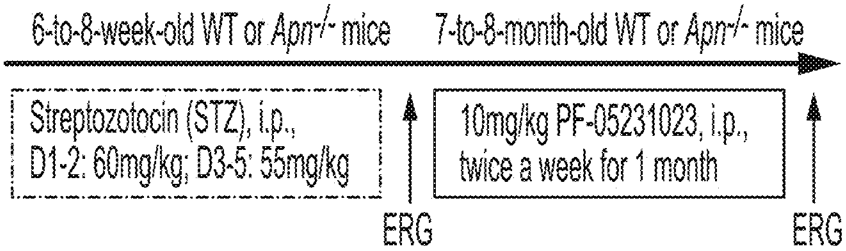
Figure 18B:
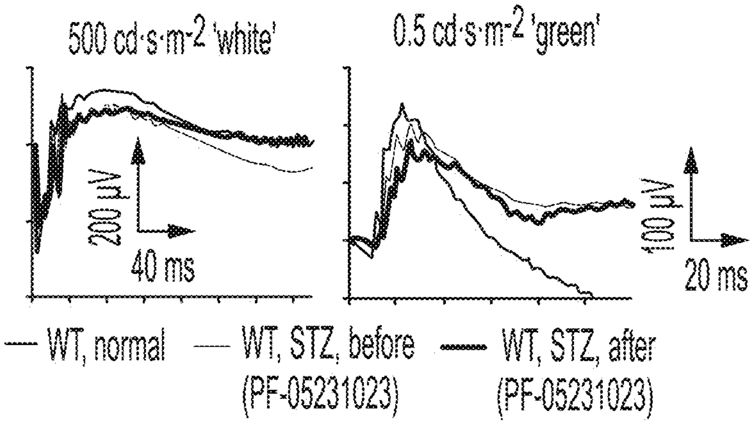
Figure 18C:
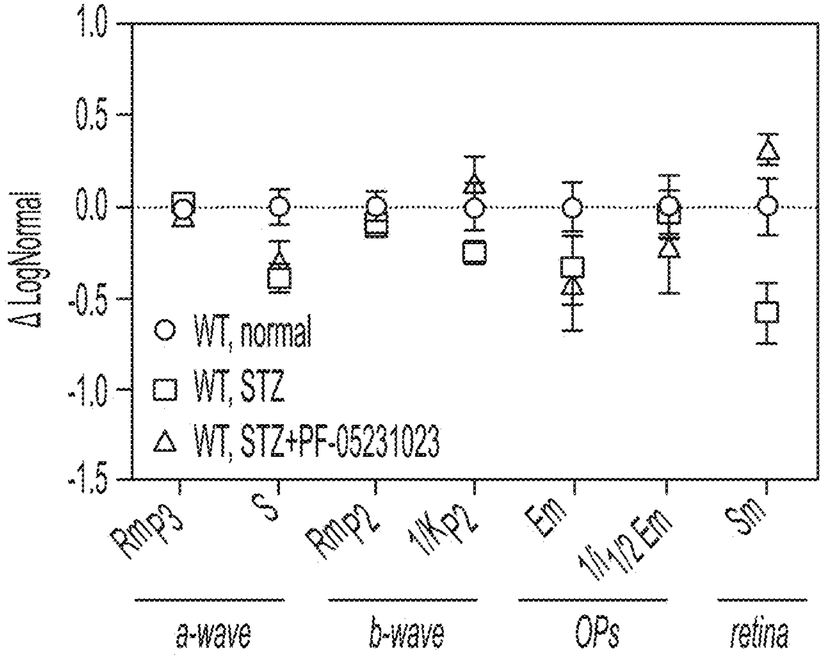
Figure 18D:
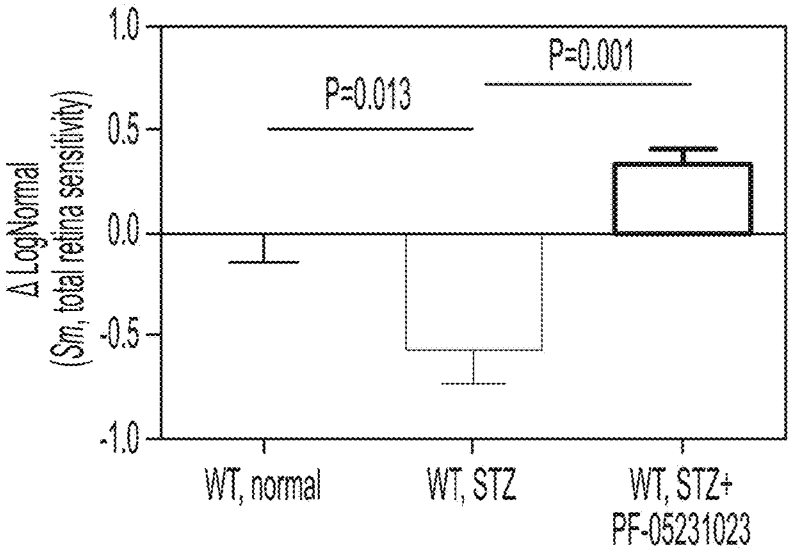
Figure 18E:
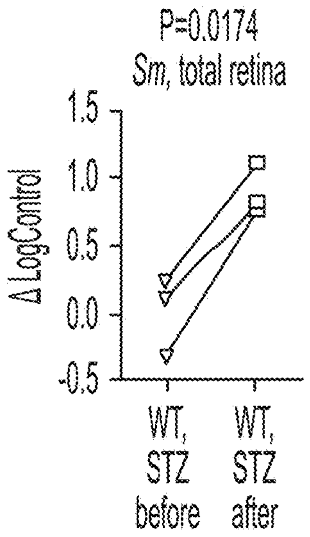
FIG. 18E shows plots of ERG parameters in 7-to-8-month-old Akita mice before and after PF-05231023 administration. n=5 mice per group. Paired t test. Data was presented as Mean±SEM.
Figure 18F:
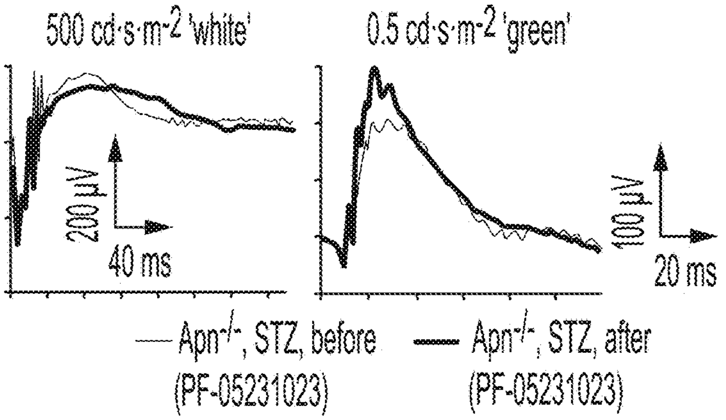
Figure 18G:
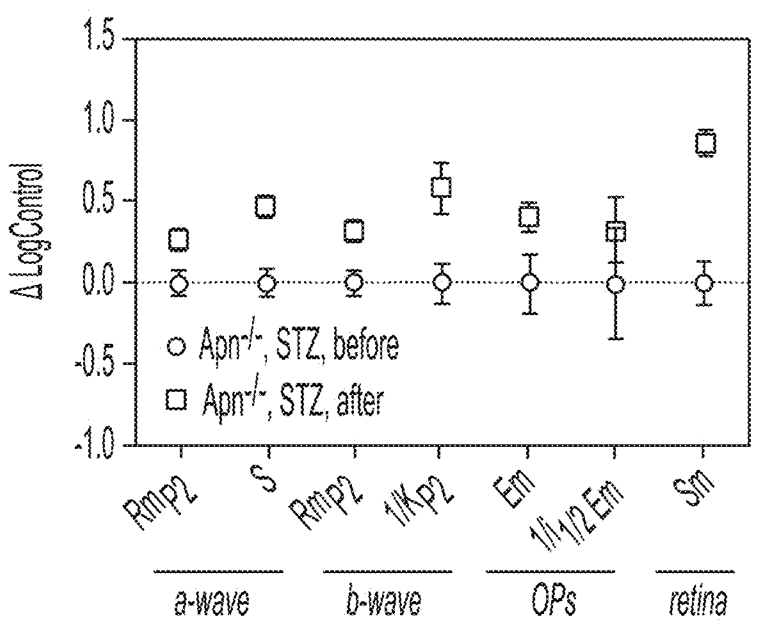
Figure 18H:
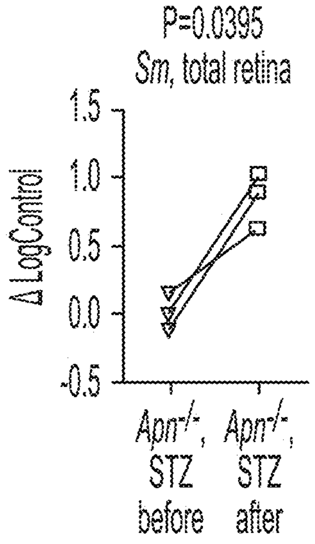
Figure 18I:
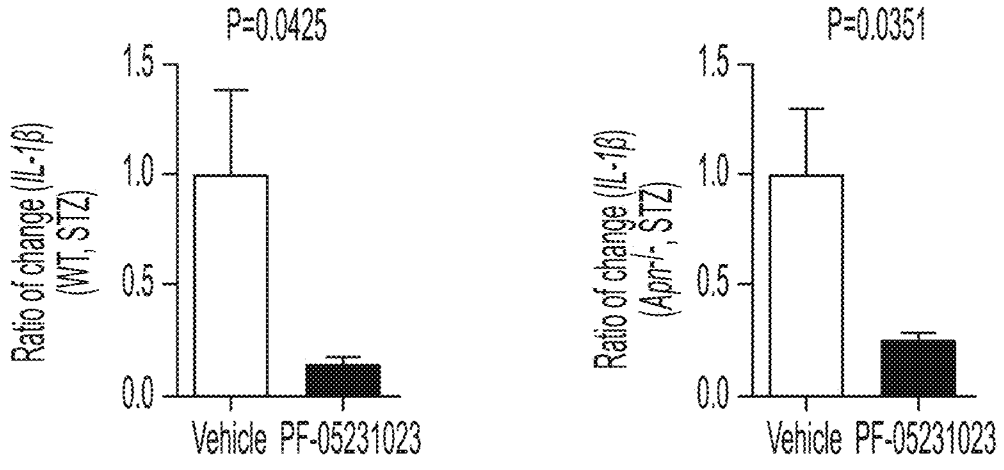
Figure 23C:
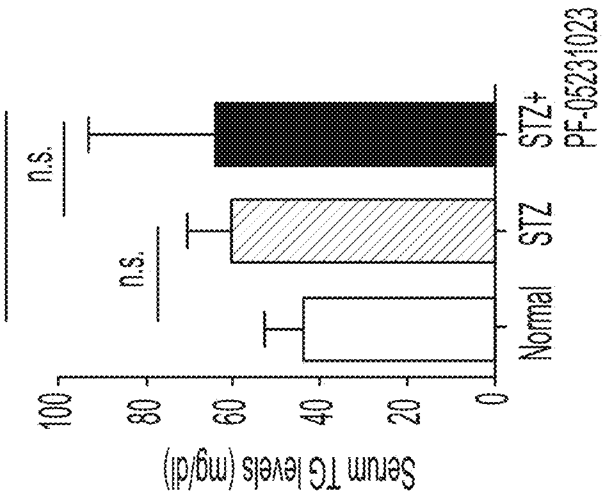
FIGS. 23A-23C are graphs showing that blood glucose levels (FIG. 23B) were increased, body weight (FIG. 23A) and serum TG levels (FIG. 23C) were not changed in STZ-induced diabetic WT mice versus normal WT mice; PF-05231023 administration did not change the body weight, blood glucose levels or serum TG levels in STZ-induced diabetic WT mice. Data is presented as Mean±SEM. n=3-5 mice per group. ANOVA followed by Bonferroni's multiple comparisons test. n.s., no significance.
Figure 23B:
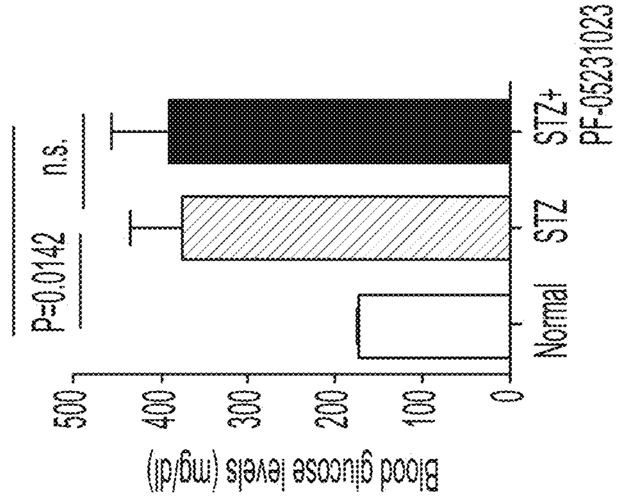
Figure 23A:
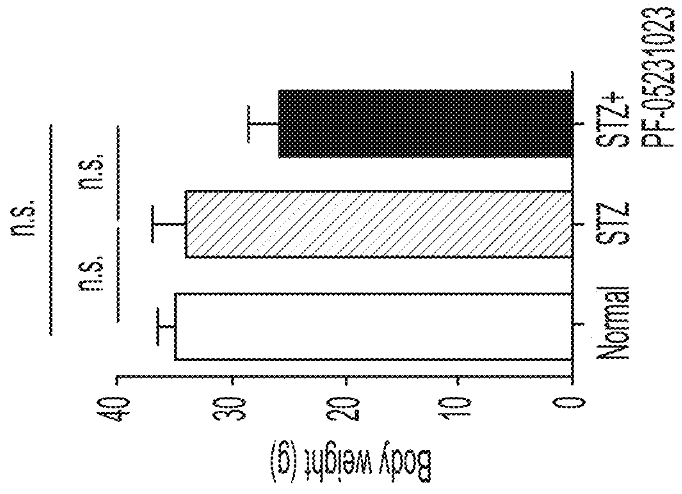

PF-05231023 administration protected STZ-induced diabetic mice against DR, partly independent of adiponectin (APN): APN is a key mediator of FGF21 modulation of glucose and lipid metabolism in mice (Lin Z, et al. *Cell Metabolism* 2013; 17:779-78947; Holland W L, et al., *Cell Metabolism* 2013; 17:790-797). Changes in the APN pathway may contribute to the development of neovascular eye diseases (Fu Z, et al., Biochimica et Biophysica Acta 2016; 1862:1392-1400). To test if APN mediated the protective effects of PF-05231023, diabetes was induced with injection of STZ in 6-8-week-old WT and in APN-deficient ($Apn^{-/-}$) mice. Retinal function was then examined by ERG at 7-8-months of age. Again, PF-05231023 administration did not change body weight, blood glucose levels or serum triglyceride levels (FIGS. 23A-23C). Furthermore, neither the amplitude nor sensitivity of the a-wave, b-wave, or the OPs differed significantly between STZ-treated mice (FIGS. 18A-18C) but, retinal sensitivity at threshold, Sm, was significantly attenuated following STZ-treatment (F=12.2, df=1, 6.0, p=0.013, FIG. 18D). PF-05231023, administered as above, again improved Sm (F=45.2, df=1, 5.9, p=0.001) in the STZ treated mice to levels that were supranormal (FIGS. 18D-18E). The protective effects of PF-05231023 on retinal sensitivity (Sm) in STZ-induced WT diabetic mice were again found in $Apn^{-/-}$ diabetic mice (F=23.8, df=1, 2, p=0.040, FIGS. 18F-18H), providing evidence that the rescue was partly independent of APN. In the STZ-induced diabetic mice, PF-05231023 decreased IL-1β expression in diabetic WT and $Apn^{-/-}$ retinas (FIG. 18I), suggesting that PF-05231023-induced reduction in IL-1β was independent of APN, in line with the phenotypic observation above (FIGS. 18F-18H).

Discussion

Figure 19:
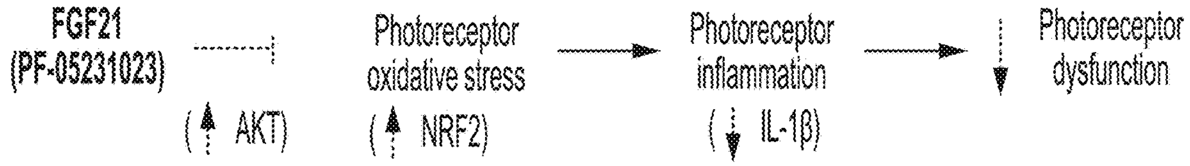
FIG. 19 is a schematic of a flow chart for PF-05231023 protection against DR in type 1 diabetic mice. Schematic of signaling pathway that PF-05231023 may improve retinal neurovascular activity in diabetic mice by activating the AKT pathway and inducing anti-oxidative NRF2, which in turn decreases photoreceptor-derived pro-inflammatory marker IL-1β.

Dysfunction in photoreceptors and post receptor neurons are among the early retinal changes seen in diabetic patients, anteceding ophthalmoscopic signs of retinopathy (Pescosolido N. et al., *J. Diabetes Research* 2015; 2015: 319692). In diabetes, hyperglycemia induces oxidative stress, a crucial contributor leading to diabetic retinopathy (Madsen-Bouterse S A, Kowluru R A.: Oxidative stress and diabetic retinopathy: pathophysiological mechanisms and treatment perspectives. *Reviews in Endocrine & Metabolic Disorders* 2008; 9:315-327). Activation of the anti-oxidant protein NRF2 protects against retinal neuronal degeneration (Xiong W., et al. *The Journal of Clin. Invest.* 2015; 125:1433-1445), particularly in photoreceptors, as photoreceptors are the most metabolically active cells in the body (Wong-Riley M T. *Eye and Brain* 2010; 2:99-116; Okawa H, et al., *Current Biology:* CB 2008; 18:1917-1921) and more vulnerable to oxidative stress damage. It was demonstrated herein that, in insulin-deficient diabetic mice, administration of the long-acting FGF21 analog PF-05231023 reversed diabetes-induced retinal neuronal deficits with improved photoreceptor function and morphology, and decreased photoreceptor-derived inflammation (FIG. 19). PF-05231023 administration regulated retinal NRF2 levels through activation of the AKT pathway, and suppression of pro-inflammatory IL-1β expression. IL-1β causes neurovascular damages in the retina (Abcouwer S F, et al., *Invest. Ophthal. & Vis. Sci.* 2008; 49:5581-5592; Kowluru R A, Odenbach S. *Invest. Ophthal. & Vis. Sci.* 2004; 45:4161-4166; Liu Y. et al., *PloS one* 2012; 7:e36949). Therefore, it was proposed that FGF21 (PF-05231023) regulates retinal NRF2 levels to reduce IL-1β production and photoreceptor dysfunction in DR.

Photoreceptor high energy consumption makes it susceptible to neurovascular disease. Blood vessels supply nutrients and oxygen to neurons, and evacuate waste. Disturbances in neuronal activity trigger vascular remodeling (Fulton A B, et al., *Documenta Ophthalmologica Advances in Ophthalmology* 2009; 118:55-61). In diabetic animal models, photoreceptor responses to hyperglycemia induce retinal blood vessel loss (Du Y. et al., *Proc. Nat'l. Acad. Sci.* USA 2013; 110:16586-165916; Liu H., et al., *Invest. Ophthal. & Vis. Sci.* 2016; 57:4272-4281; Tonade D. et al., *Invest. Ophthal. & Vis. Sci.* 2016; 57:4264-4271). In addition, low rod sensitivity is associated with abnormal retinal vasculature. Rod photoreceptor demands contribute to the vascular recovery in hypoxia-induced retinal neovascularization (Akula J D et al., *Invest. Ophthal. & Vis. Sci.* 2007; 48:4351-4359). Photoreceptor metabolic dysfunction dictates pathological retinal angiogenesis (Joyal J S et al., *Nature Medicine* 2016; 22:439-445). Therefore, maintaining photoreceptor function may prevent vascular abnormalities in DR. In insulin-deficient Akita mice, reduced sensitivity was found in the post-receptor retina, in line with clinical observations (Pescosolido N., et al., *J. Diabetes Res.* 2015; 2015:319692). Meanwhile, the changes in post-receptor cells were actually reflecting the deficits in photoreceptor function (Hansen R M, et al., *Prog. Retinal and Eye Res.* 2017; 56:32-57; Hood D C, et al. *Vis. Neurosci.* 1992; 8:107-126). Administration of a FGF21 analogue, PF-05231023, reversed the diabetes-induced morphological changes in photoreceptors and restored retinal sensitivity; it also reduced disorganization of the photoreceptor segments. This provides evidence that PF-05231023"s effect on retinal function ERG may be due to improved photoreceptor structure and function.

There is a strong correlation between hyperglycemia and the development of DR. Hyperglycemia leads to many cellular metabolic alterations that could serve as therapeutic targets. However, while pharmacologic interventions that disrupt putative biochemical signaling pathways between hyperglycemia and DR, an effective and safe drug is not yet available. Type 1 diabetic patients have low circulating FGF21 levels (Zibar K, et al., *Endocrine* 2014; Xiao Y, et al., *J. Clin. Endocrinol. Metabol.* 2012; 97:E54-58) and FGF21 administration reduces hyperglycemia and lessens renal dysfunction in type 1 diabetic mice (Jiang X, et al., *Toxicol. Letters* 2013; 219:65-76). FGF21 also improves the lipid profile (decreased triglycerides) of obese monkeys and type 2 diabetic patients (Talukdar S, et al., *Cell Metabolism* 2016; 23:427-440), indicating that FGF21 may have positive effects on diabetes and diabetic complications.

No significant impact of PF-05231023 administration on serum triglyceride levels in either Akita or STZ-induced diabetic mice. Although PF-05231023 slightly reduced hyperglycemia in Akita mice, this finding was not replicated in STZ-induced mice. The protective effects of PF-05231023 on retinal neurons is, therefore, likely to be independent of circulating glucose and lipid modulation. It was also discovered that PF-05231023 protection against retinal neuronal deficits was preserved with APN deficiency. In the oxygen-induced retinopathy mouse model of late vaso-proliferative retinopathy, FGF21 inhibits pathologic neovessel growth mediated by APN (Fu Z, et al., *Cell Reports* 2017; 18:1606-1613). The current findings indicate that FGF21 regulates retinal neuron and neovessel growth through other mechanisms.

Oxidative stress resulting from highly metabolic photoreceptors induces inflammation, which induces DR (Du Y, et al., *Proc. Nat'l. Acad. Sci.* USA 2013; 110:16586-16591; Liu H, et al., *Inv. Ophthal. & Vis. Sci.* 2016; 57:4272-4281; Tonade D. et al., *Invest. Ophthal. & Vis. Sci.* 2016; 57:4264-4271; Joussen A M et al., *FASEB J.* 2004; 18:1450-1452; Kern T S, Berkowitz B A: *J. Diabetes Invest.* 2015; 6:371-380). Modulating oxidative stress prevents the progression of DR (Williams M, et al., *Current Diabetes Reports* 2013; 13:481-487). PF-05231023 administration attenuated the diabetes-induced IL-1β expression in Akita mice. FGF21 reduces oxidative stress and inhibits the NFκB pathway in mice (Yu Y, et al., *International Immunopharmacology* 2016; 38:144-152). In photoreceptors in vitro with paraquat-induced oxidative stress, it was observed that PF-05231023 treatment decreased IL-1β expression through the activation of the NRF2 pathway, which is known for its antioxidant capability (Xiong W, et al., *J. Clin. Invest.* 2015; 125:1433-1445) and regulation of IL-1β transcription (Yu Y, et al., 2016; Kobayashi E H, et al., *Nature Communications* 2016; 7:1162443; 44). Additionally, PF-05231023-induced effect on IL-1β was independent of APN in diabetic retinas, in line with the neuronal observation. APN inhibits retinal neovessel growth via TNFα (Higuchi A, et al., *Circulation Research* 2009; 104:1058-1065) and FGF21 also reduces TNFα in neovascular mouse retinas (Fu Z, et al., 2017). However, in Akita mice, there was no significant change in retinal Tnfα expression between PF-05231023—and vehicle-treated groups. Taken together, it was concluded that in diabetic retinas, PF-05231023 protected neuronal activity through the NRF2-IL-1β pathway, which was at least to some degree independent of the APN-TNFα pathway that the inventors showed to be involved in retinal neovascularization in OIR (Fu Z, et al., *Am. J. Clin. Nutrition* 2015; 101:879-888). IL-1β causes a decline in mitochondrial membrane potential and ATP production in retinal neurons (Abcouwer S F, et al., *Invest. Ophthal. & Vis. Sci.* 2008; 49:5581-5592). Reduction of retinal IL-1β may prevent the induction of early vessel loss in DR as IL-1β induces retinal microvascular abnormalities in rats (Kowluru R A, Odenbach S. *Invest. Ophthal. & Vis. Sci.* 2004; 45:4161-4166; Liu Y, et al., *PloS one* 2012; 7:e36949).

Figure 24A:
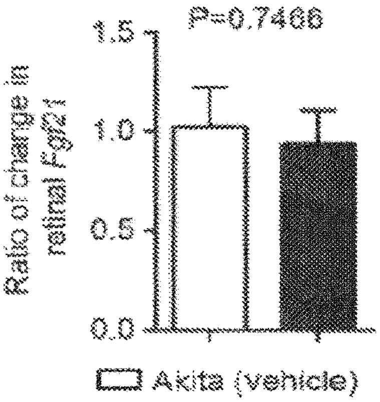
FIGS. 24A-24C are graphs showing results from a qPCR of retinal Fgf21 (FIG. 24A), Fgfr1 (FIG. 24B) and Klb (FIG. 24C) in Akita mice with PF-05231023 or vehicle treatment. n=3-4 mice per group. Unpaired t test.
Figure 24B:
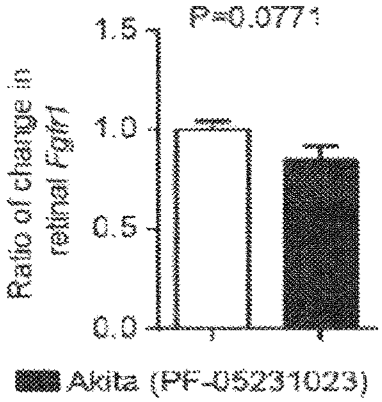
Figure 24C:
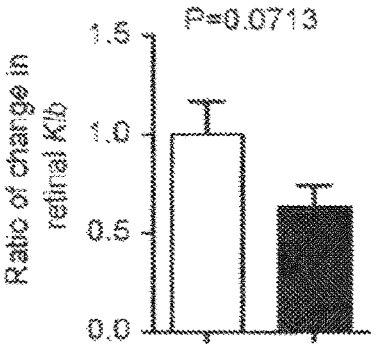

In this study, PF-05231023 was administrated intraperitoneally and circulating FGF21 levels were measured. PF-05231023 administration did not alter retinal Fgf21, Fgfr1 and Klb expression in Akita mice (FIGS. 24A-24C). These data implicate circulating/peripheral FGF21 as a primary driver of retinal protection rather than autocrine/paracrine effects of FGF21 in the retina. Although FGF21 is expressed in liver, white adipose tissue and brown adipose tissue, it is a hepatokine and liver is the primary source of circulating FGF21 under fasting and refeeding conditions (Markan K R, et al., *Diabetes* 2014; 63:4057-4063). In humans, liver is also the primary source of circulating FGF21 in a pattern consistent with a hormonal response (Yang C, et al., *BMC Gastroenterology* 2013; 13:67). While liver-derived FGF21 is critical for the adaptive response to fasting or starvation in rodents, in humans, FGF21 plays an important role in fructose metabolism (Dushay J R, et al. *Molecular Metabolism* 2015; 4:51-57). Circulating FGF21 has been shown to cross the blood brain barrier in humans in a non-saturable, unidirectional manner (Hsuchou H, et al., *Peptides* 2007; 28:2382-2386). FGF21 regulates metabolism and circadian behavior, sweet and alcohol preferences by directly acting on the nervous system (Bookout A L, et al. *Nature Medicine* 2013; 19:1147-1152; Talukdar S, et al. *Cell Metabolism* 2016; 23:344-349). The blood retinal barrier (BRB), which is essential for normal visual function (Cunha-Vaz J: The Blood-Retinal Barrier in the Management of Retinal Disease: EURETINA Award Lecture. *Ophthalmologica Journal international d'ophtalmologie International journal of ophthalmology Zeitschrift fur Augenheilkunde* 2017; 237:1-10), is broken down in DR (Klaassen I, et al. *Progress in Retinal and Eye Research* 2013; 34:19-48). The leaky BRB potentiates the transport of FGF21 from blood into retina. As local expression of FGF21 receptors has been detected in total retina and in retinal neurons, circulating FGF21 could directly act on retinal neurons to exert protective effects in DR.

In summary, there is an unmet need for the prevention and treatment of DR. Maintaining retinal structure and function particularly photoreceptor activity improves retinal vascular stability, which can be achieved by two ways: i) modulating photoreceptor metabolism to match the energy supply; ii) slowing down the visual cycle to reduce the energy demand.

REFERENCES

Abcouwer, S. F., and Gardner, T. W. (2014). Diabetic retinopathy: loss of neuroretinal adaptation to the diabetic metabolic environment. Annals of the New York Academy of Sciences 1311, 174-190.

Arevalo, J. F. (2013). Intravitreal bevacizumab as anti-vascular endothelial growth factor in the management of complications of proliferative diabetic retinopathy. Medical hypothesis, discovery and innovation in ophthalmology 2, 20-24.

Barron, M. J., Johnson, M. A., Andrews, R. M., Clarke, M. P., Griffiths, P. G., Bristow, E., He, L. P., Durham, S., and Turnbull, D. M. (2001). Mitochondrial abnormalities in ageing macular photoreceptors. Investigative ophthalmology & visual science 42, 3016-3022.

Bernardo, B., Lu, M., Bandyopadhyay, G., Li, P., Zhou, Y., Huang, J., Levin, N., Tomas, E. M., Calle, R. A., Erion, D. M., Rolph, T. P., Brenner, M., and Talukdar, S. (2015). FGF21 does not require interscapular brown adipose tissue and improves liver metabolic profile in animal models of obesity and insulin-resistance. Scientific reports 5, 11382.

Chen, J., and Smith, L. E. (2007). Retinopathy of prematurity. Angiogenesis 10, 133-140.

Cheung, N., Lam, D. S., and Wong, T. Y. (2012). Anti-vascular endothelial growth factor treatment for eye diseases. Bmj 344, e2970.

Ciulla, T. A., Amador, A. G., and Zinman, B. (2003). Diabetic retinopathy and diabetic macular edema: pathophysiology, screening, and novel therapies. Diabetes care 26, 2653-2664.

Connor, K. M., Krah, N. M., Dennison, R. J., Aderman, C. M., Chen, J., Guerin, K. I., Sapieha, P., Stahl, A., Willett, K. L., and Smith, L. E. (2009). Quantification of oxygen-induced retinopathy in the mouse: a model of vessel loss, vessel regrowth and pathological angiogenesis. Nature protocols 4, 1565-1573.

Cross, M. J., and Claesson-Welsh, L. (2001). FGF and VEGF function in angiogenesis: signalling pathways, biological responses and therapeutic inhibition. Trends in pharmacological sciences 22, 201-207.

Ding, X., Boney-Montoya, J., Owen, B. M., Bookout, A. L., Coate, K. C., Mangelsdorf, D. J., and Kliewer, S. A. (2012). betaKlotho is required for fibroblast growth factor 21 effects on growth and metabolism. Cell metabolism 16, 387-393.

Engelbert, M., and Yannuzzi, L. A. (2012). Idiopathic macular telangiectasia type 2: the progressive vasculopathy. European journal of ophthalmology, 0.

Esteghamati, A., Momeni, A., Abdollahi, A., Khandan, A., Afarideh, M., Noshad, S., and Nakhjavani, M. (2016). Serum fibroblast growth factor 21 concentrations in type 2 diabetic retinopathy patients. Annales d'endocrinologie.

Fernando Arevalo, J. (2013). Intravitreal bevacizumab as anti-vascular endothelial growth factor in the management of complications of proliferative diabetic retinopathy. Medical hypothesis, discovery and innovation in ophthalmology 2, 20-24.

Foltz, I. N., Hu, S., King, C., Wu, X., Yang, C., Wang, W., Weiszmann, J., Stevens, J., Chen, J. S., Nuanmanee, N., Gupte, J., Komorowski, R., Sekirov, L., Hager, T., Arora, T., Ge, H., Baribault, H., Wang, F., Sheng, J., Karow, M., Wang, M., Luo, Y., McKeehan, W., Wang, Z., Veniant, M. M., and Li, Y. (2012). Treating diabetes and obesity with an FGF21-mimetic antibody activating the betaKlotho/FGFR1c receptor complex. Science translational medicine 4, 162ra153.

Fu, Z., Gong, Y., Lofqvist, C., Hellstrom, A., and Smith, L. E. (2016). Review: adiponectin in retinopathy. Biochimica et biophysica acta 1862, 1392-1400.

Fu, Z., Lofqvist, C. A., Shao, Z., Sun, Y., Joyal, J. S., Hurst, C. G., Cui, R. Z., Evans, L. P., Tian, K., SanGiovanni, J. P., Chen, J., Ley, D., Hansen Pupp, I., Hellstrom, A., and Smith, L. E. (2015). Dietary omega-3 polyunsaturated fatty acids decrease retinal neovascularization by adipose-endoplasmic reticulum stress reduction to increase adiponectin. The American journal of clinical nutrition 101, 879-888.

Gaich, G., Chien, J. Y., Fu, H., Glass, L. C., Deeg, M. A., Holland, W. L., Kharitonenkov, A., Bumol, T., Schilske, H. K., and Moller, D. E. (2013). The effects of LY2405319, an FGF21 analog, in obese human subjects with type 2 diabetes. Cell metabolism 18, 333-340.

Gilbert, C., Rahi, J., Eckstein, M., O'Sullivan, J., and Foster, A. (1997). Retinopathy of prematurity in middle-income countries. Lancet 350, 12-14.

Gong, Y., Li, J., Sun, Y., Fu, Z., Liu, C. H., Evans, L., Tian, K., Saba, N., Fredrick, T., Morss, P., Chen, J., and Smith, L. E. (2015). Optimization of an Image-Guided Laser-Induced Choroidal Neovascularization Model in Mice. PloS one 10, e0132643.

Hangai, M., He, S., Hoffmann, S., Lim, J. I., Ryan, S. J., and Hinton, D. R. (2006). Sequential induction of angiogenic growth factors by TNF-alpha in choroidal endothelial cells. Journal of neuroimmunology 171, 45-56.

Heeren, T. F., Holz, F. G., and Charbel Issa, P. (2014). First symptoms and their age of onset in macular telangiectasia type 2. Retina 34, 916-919.

Hellstrom, A., Smith, L. E., and Dammann, O. (2013). Retinopathy of prematurity. Lancet 382, 1445-1457.

Higuchi, A., Ohashi, K., Kihara, S., Walsh, K., and Ouchi, N. (2009). Adiponectin suppresses pathological microvessel formation in retina through modulation of tumor necrosis factor-alpha expression. Circulation research 104, 1058-1065.

Higuchi, A., Ohashi, K., Shibata, R., Sono-Romanelli, S., Walsh, K., and Ouchi, N. (2010). Thiazolidinediones reduce pathological neovascularization in ischemic retina via an adiponectin-dependent mechanism. Arteriosclerosis, thrombosis, and vascular biology 30, 46-53.

Holland, W. L., Adams, A. C., Brozinick, J. T., Bui, H. H., Miyauchi, Y., Kusminski, C. M., Bauer, S. M., Wade, M., Singhal, E., Cheng, C. C., Volk, K., Kuo, M. S., Gordillo, R., Kharitonenkov, A., and Scherer, P. E. (2013). An FGF21-adiponectin-ceramide axis controls energy expenditure and insulin action in mice. Cell metabolism 17, 790-797.

Huang, J., Ishino, T., Chen, G., Rolzin, P., Osothprarop, T. F., Retting, K., Li, L., Jin, P., Matin, M. J., Huyghe, B., Talukdar, S., Bradshaw, C. W., Palanki, M., Violand, B. N., Woodnutt, G., Lappe, R. W., Ogilvie, K., and Levin, N. (2013). Development of a novel long-acting antidiabetic FGF21 mimetic by targeted conjugation to a scaffold antibody. The Journal of pharmacology and experimental therapeutics 346, 270-280.

Joyal, J. S., Sun, Y., Gantner, M. L., Shao, Z., Evans, L. P., Saba, N., Fredrick, T., Burnim, S., Kim, J. S., Patel, G., Juan, A. M., Hurst, C. G., Hatton, C. J., Cui, Z., Pierce, K. A., Bherer, P., Aguilar, E., Powner, M. B., Vevis, K., Boisvert, M., Fu, Z., Levy, E., Fruttiger, M., Packard, A., Rezende, F. A., Maranda, B., Sapieha, P., Chen, J., Friedlander, M., Clish, C. B., and Smith, L. E. (2016). Retinal lipid and glucose metabolism dictates angiogenesis through the lipid sensor Ffar1. Nature medicine 22, 439-445.

Kaarniranta, K., Paananen, J., Nevalainen, T., Sorri, I., Seitsonen, S., Immonen, I., Salminen, A., Pulkkinen, L., and Uusitupa, M. (2012). Adiponectin receptor 1 gene (ADIPOR1) variant is associated with advanced age-related macular degeneration in Finnish population. Neuroscience letters 513, 233-237.

Kim, J. H., Bae, K. H., Choi, Y. K., Go, Y., Choe, M., Jeon, Y. H., Lee, H. W., Koo, S. H., Perfield, J. W., 2nd, Harris, R. A., Lee, I. K., and Park, K. G. (2015). Fibroblast growth factor 21 analogue LY2405319 lowers blood glucose in streptozotocin-induced insulin-deficient diabetic mice by restoring brown adipose tissue function. Diabetes, obesity & metabolism 17, 161-169.

Kociok, N., Radetzky, S., Krohne, T. U., Gavranic, C., and Joussen, A. M. (2006). Pathological but not physiological retinal neovascularization is altered in TNF-Rp55-receptor-deficient mice. Investigative ophthalmology & visual science 47, 5057-5065.

Lai, A. K., and Lo, A. C. (2013). Animal models of diabetic retinopathy: summary and comparison. Journal of diabetes research 2013, 106594.

Lambert, N. G., ElShelmani, H., Singh, M. K., Mansergh, F. C., Wride, M. A., Padilla, M., Keegan, D., Hogg, R. E., and Ambati, B. K. (2016). Risk factors and biomarkers of age-related macular degeneration. Progress in retinal and eye research 54, 64-102.

Lin, Y., Xiao, Y. C., Zhu, H., Xu, Q. Y., Qi, L., Wang, Y. B., Li, X. J., Zheng, M. L., Zhong, R. S., Zhang, Y., Xu, X. D., Wu, B. L., Xu, Z. M., and Lu, X. H. (2014). Serum fibroblast growth factor 21 levels are correlated with the severity of diabetic retinopathy. Journal of diabetes research 2014, 929756.

Lin, Z., Tian, H., Lam, K. S., Lin, S., Hoo, R. C., Konishi, M., Itoh, N., Wang, Y., Bornstein, S. R., Xu, A., and Li, X. (2013). Adiponectin mediates the metabolic effects of FGF21 on glucose homeostasis and insulin sensitivity in mice. Cell metabolism 17, 779-789.

Lyzogubov, V. V., Tytarenko, R. G., Bora, N. S., and Bora, P. S. (2012). Inhibitory role of adiponectin peptide I on rat choroidal neovascularization. Biochimica et biophysica acta 1823, 1264-1272.

Mao, D., Peng, H., Li, Q., Wang, J., Li, P., Hu, K., Zhang, X., and Lei, B. (2012). Aqueous humor and plasma adiponectin levels in proliferative diabetic retinopathy patients. Current eye research 37, 803-808.

Omae, T., Nagaoka, T., and Yoshida, A. (2015). Relationship Between Retinal Blood Flow and Serum Adiponectin Concentrations in Patients With Type 2 Diabetes Mellitus. Investigative ophthalmology & visual science 56, 4143-4149.

Osaadon, P., Fagan, X. J., Lifshitz, T., and Levy, J. (2014). A review of anti-VEGF agents for proliferative diabetic retinopathy. Eye (Lond) 28, 510-520.

Park, P. H., Huang, H., McMullen, M. R., Mandal, P., Sun, L., and Nagy, L. E. (2008). Suppression of lipopolysaccharide-stimulated tumor necrosis factor-alpha production by adiponectin is mediated by transcriptional and post-transcriptional mechanisms. The Journal of biological chemistry 283, 26850-26858.

Parmeggiani, F., Romano, M. R., Costagliola, C., Semeraro, F., Incorvaia, C., D'Angelo, S., Perri, P., De Palma, P., De Nadai, K., and Sebastiani, A. (2012). Mechanism of inflammation in age-related macular degeneration. Mediators of inflammation 2012, 546786.

Ryan, S. J. (1979). The development of an experimental model of subretinal neovascularization in disciform macular degeneration. Transactions of the American Ophthalmological Society 77, 707-745.

Sainson, R. C., Johnston, D. A., Chu, H. C., Holderfield, M. T., Nakatsu, M. N., Crampton, S. P., Davis, J., Conn, E., and Hughes, C. C. (2008). TNF primes endothelial cells for angiogenic sprouting by inducing a tip cell phenotype. Blood 111, 4997-5007.

Sato, T., Wada, K., Arahori, H., Kuno, N., Imoto, K., Iwahashi-Shima, C., and Kusaka, S. (2012). Serum concentrations of bevacizumab (avastin) and vascular endothelial growth factor in infants with retinopathy of prematurity. American journal of ophthalmology 153, 327-333 e321.

Schlein, C., Talukdar, S., Heine, M., Fischer, A. W., Krott, L. M., Nilsson, S. K., Brenner, M. B., Heeren, J., and Scheja, L. (2016). FGF21 Lowers Plasma Triglycerides by Accelerating Lipoprotein Catabolism in White and Brown Adipose Tissues. Cell metabolism 23, 441-453.

Shi, X., Semkova, I., Muther, P. S., Dell, S., Kociok, N., and Joussen, A. M. (2006). Inhibition of TNF-alpha reduces laser-induced choroidal neovascularization. Experimental eye research 83, 1325-1334.

Shin, E. S., Sorenson, C. M., and Sheibani, N. (2014). Diabetes and retinal vascular dysfunction. Journal of ophthalmic & vision research 9, 362-373.

Smith, L. E., Wesolowski, E., McLellan, A., Kostyk, S. K., D'Amato, R., Sullivan, R., and D'Amore, P. A. (1994). Oxygen-induced retinopathy in the mouse. Investigative ophthalmology & visual science 35, 101-111.

Suzuki, M., Uehara, Y., Motomura-Matsuzaka, K., Oki, J., Koyama, Y., Kimura, M., Asada, M., Komi-Kuramochi, A., Oka, S., and Imamura, T. (2008). betaKlotho is required for fibroblast growth factor (FGF) 21 signaling through FGF receptor (FGFR) 1c and FGFR3c. Mol Endocrinol 22, 1006-1014.

Talukdar, S., Zhou, Y., Li, D., Rossulek, M., Dong, J., Somayaji, V., Weng, Y., Clark, R., Lanba, A., Owen, B. M., Brenner, M. B., Trimmer, J. K., Gropp, K. E., Chabot, J. R., Erion, D. M., Rolph, T. P., Goodwin, B., and Calle, R. A. (2016). A Long-Acting FGF21 Molecule, PF-05231023, Decreases Body Weight and Improves Lipid Profile in Non-human Primates and Type 2 Diabetic Subjects. Cell metabolism 23, 427-440.

Wulster-Radcliffe, M. C., Ajuwon, K. M., Wang, J., Christian, J. A., and Spurlock, M. E. (2004). Adiponectin differentially regulates cytokines in porcine macrophages. Biochemical and biophysical research communications 316, 924-929.

Xiao, Y., Xu, A., Law, L. S., Chen, C., Li, H., Li, X., Yang, L., Liu, S., Zhou, Z., and Lam, K. S. (2012). Distinct changes in serum fibroblast growth factor 21 levels in different subtypes of diabetes. The Journal of clinical endocrinology and metabolism 97, E54-58.

Yaqoob, U., Jagavelu, K., Shergill, U., de Assuncao, T., Cao, S., and Shah, V. H. (2014). FGF21 promotes endothelial cell angiogenesis through a dynamin-2 and Rab5 dependent pathway. PloS one 9, e98130.

Yonekawa, Y., Miller, J. W., and Kim, I. K. (2015). Age-Related Macular Degeneration: Advances in Management and Diagnosis. Journal of clinical medicine 4, 343-359.

Zhang, C., Shao, M., Yang, H., Chen, L., Yu, L., Cong, W., Tian, H., Zhang, F., Cheng, P., Jin, L., Tan, Y., Li, X., Cai, L., and Lu, X. (2013). Attenuation of hyperlipidemia- and diabetes-induced early-stage apoptosis and late-stage renal dysfunction via administration of fibroblast growth factor-21 is associated with suppression of renal inflammation. PloS one 8, e82275.

Zibar, K., Blaslov, K., Bulum, T., Cuca, J. K., and Smircic-Duvnjak, L. (2014). Basal and postprandial change in serum fibroblast growth factor-21 concentration in type 1 diabetic mellitus and in healthy controls. Endocrine.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for decreasing neovascularization or angiogenesis in the eye of a subject, the method comprising:

(a) identifying a subject having neovascularization or angiogenesis in the eye; and (b) administering a pharmaceutical composition comprising a stabilized fibroblast growth factor 21 (FGF21) agent to the subject, and thereby treating neovascularization or angiogenesis in the eye of the subject, wherein the stabilized FGF21 agent comprises an FGF21 polypeptide conjugated to an antibody scaffold.

2. The method of claim 1, wherein the subject has neovascular retinopathy.

3. The method of claim 1, wherein the subject has a condition selected from the group consisting of diabetic retinopathy in type I diabetes, hyperglycemic retinopathy of prematurity (ROP), retinitis pigmentosa (RP) and macular telangiectasia (MacTel).

4. The method of claim 1, wherein neovascularization and/or angiogenesis in the choroid cells or in the retinal cells of the eye is treated.

5. The method of claim 1, wherein two or more FGF21 polypeptide molecules are conjugated to one antibody scaffold.

6. The method of claim 1, wherein the stabilized FGF21 agent possesses a half-life of at least 1.5× the half-life of a native FGF21 peptide when assayed for stability under identical conditions, optionally at least 2× the half-life of a native FGF21 peptide when assayed for stability under identical conditions, optionally at least 3× the half-life of a native FGF21 peptide when assayed for stability under identical conditions, optionally at least 4× the half-life of a native FGF21 peptide when assayed for stability under identical conditions, optionally at least 5× the half-life of a native FGF21 peptide when assayed for stability under identical conditions, optionally at least 8× the half-life of a native FGF21 peptide when assayed for stability under identical conditions, optionally at least 10× the half-life of a native FGF21 peptide when assayed for stability under identical conditions, optionally at least 12× the half-life of a native FGF21 peptide when assayed for stability under identical conditions, optionally at least 15× the half-life of a native FGF21 peptide when assayed for stability under identical conditions, optionally at least 20× the half-life of a native FGF21 peptide when assayed for stability under identical conditions, optionally at least 30× the half-life of a native FGF21 peptide when assayed for stability under identical conditions, optionally at least 40× the half-life of a native FGF21 peptide when assayed for stability under identical conditions, optionally at least 50× the half-life of a native FGF21 peptide when assayed for stability under identical conditions, optionally at least 60× the half-life of a native FGF21 peptide when assayed for stability under identical conditions or optionally at least 70× the half-life of a native FGF21 peptide when assayed for stability under identical conditions.

7. The method of claim 1, wherein the stabilized FGF21 agent possesses a half-life of at least 0.8 h in the circulation of a mammal, optionally at least 1 h, at least 2 h, at least 3 h, at least 4 h, at least 5 h, at least 7 h, at least 10 h, at least 15 h, at least 20 h, at least 25 h, at least 28 h or at least 30 h in the circulation of a mammal, optionally wherein the mammal is human.

8. The method of claim 1, wherein the pharmaceutical composition is administered to the eye of the subject, optionally by intravitreal injection.

9. The method of claim 1 wherein the subject suffers from diabetic retinopathy, retinitis pigmentosa, or age-related macular degeneration.

10. The method of claim 9, wherein the age-related macular degeneration is wet macular degeneration or dry macular degeneration, or wherein the diabetic retinopathy is proliferative diabetic retinopathy or non-proliferative diabetic retinopathy, or wherein the retinitis pigmentosa is autosomal recessive, autosomal dominant or X-linked.

11. The method of claim 9, wherein the stabilized FGF-21 agent is two delHis1/A129C modified FGF-21 peptides each conjugated to a Fab region of a humanized IgG1k mAb.

12. The method of claim 9, wherein the subject suffers from hyperglycemic retinopathy of prematurity.

* * * * *

SEQUENCE LISTING

```
<160> NUMBER OF SEQ ID NOS: 49

<210> SEQ ID NO 1
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
    50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro His Arg Asp Pro Cys
        115                 120                 125

Pro Arg Gly Pro Ala Arg Phe Leu Pro Leu Pro Gly Leu Pro Pro Ala
    130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180


<210> SEQ ID NO 2
<211> LENGTH: 5324
```

-continued

<212> TYPE: DNA
<213> ORGANISM: Homo sapiens

<400> SEQUENCE: 2

```
cacagcacag caggatgact gcgggcaggc ctagataata cccagcctcc cacaagaagc     60
tggtggagca gagtgttccc tgactcctcc aagaaaagga gattcccttt cgtggtctgc    120
tgagtaacgg gtgccttccc agacactggc gttcccgctt gaccaaggag ccctcaagag    180
gcccttatgc cggtgtgaca gaaggctcac ctcttgcctt ctaggtcact tctcacaatg    240
tcccttcagt acctgaccct atacccaccg gttgtttcct ggttatatta gttatacaac    300
aaagaataaa agtaatagct aatgattaat aatgtttaca ctaatgattg atactgtcca    360
tgatcatctc tatatctaat ttgtatgata actattctta ttctaactat tttctttatt    420
atactgaaac agtttgtgcc ttcagtctct tgcctcggca cctgggtaat ccttccccac    480
agactgaccc tcccattcaa gatacatcaa tgtcaaagac tcaggagttt gacttgattc    540
ccagaagttt aaccatcatc tccccaggct cgggactccc agcacccaga cccttctgct    600
cacacccagc agtccaggcc cccagaccct cctccctcag acttaggagt ccaggctccc    660
ggcccctcct tcctcagacc caggagtcca agccccctgc ccctccttcc tcagacccag    720
gagtccagga ccccagcccc tccttcctca cacccacgag tccagatccc tagcccctac    780
tccctcagac ccaggagtcc agaccaaagc tccctcctcc ctcagaccca ggagcccaag    840
ttccccagcc cctcctccct cagatccagg agtacaggcc cagcccctcc tccctcagac    900
ccctcctccc tcagatccag gagtacaggc ccagaccctc ctccctcaga cccaggagtc    960
caggccccc  acccctcctc cctcagaccc aggagtccag agccccagcc ctcctccctc   1020
agacacagaa ggcctaccct tgcaccctta ggggctccag gaaattagcc aacctgtctt   1080
ccctctgggt gcccactcca gggcctggct tggctgccaa ctccagtcag ggactttcag   1140
ccacccctcc ccccaggtta tttcaggagc acctgcctgg gcctgggatg gcttctctgg   1200
tgaaagaaac accaggattg catcagggag gaggaggctg ggatgtccag ggtctgagca   1260
tctgagcagg gacagatgag gttgaggttg gcccacggcc aggtgagagg cttccaaggc   1320
aggatacttg tgtctcagat gcggtcgctt ctttcataca gcaattgccg ccttgctgag   1380
gatcaaggaa cctcagtgtc agatcacgcc ctccccccaa acttagaaat tcagatgggg   1440
cgcagaaatt tctcttgttc tgcgtgatct gcatagatgg tccaagaggt ggtttttcca   1500
ggagcccagc acccctcctc cctccgactc aggtgcttga gaccccagat ccttctctct   1560
gagactcagg aatgtgggcc cccagcccct ttcacctggg tcccagctaa cccgatcctc   1620
ccctccctca tcccctagac ccaggagtct ggccctccat tgaaaggacc ccaggttaca   1680
tcatccattc aggctgccct tgccacgatg gaattctgta gctcctgcca aatgggtcaa   1740
atatcatggt tcaggcgcag ggagggtgat tgggcgggcc tgtctgggta taaattctgg   1800
agcttctgca tctatcccaa aaaacaaggg tgttctgtca gctgaggatc cagccgaaag   1860
aggagccagg cactcaggcc acctgagtct actcacctgg acaactggaa tctggcacca   1920
attctaaacc actcagcttc tccgagctca caccccggag atcacctgag gacccgagcc   1980
attgatggac tcggacgaga ccgggttcga gcactcaggg ctgtgggttt ctgtgctggc   2040
tggtcttctg ctgggagcct gccaggcaca ccccatccct gactccagtc ctctcctgca   2100
attcgggggc caagtccggc agcggtacct ctacacagat gatgcccagc agacagaagc   2160
ccacctggag atcagggagg atgggacggt ggggggcgct gctgaccaga gccccgaaag   2220
```

-continued

```
tgagtgtggg ccagagcctg ggtctgaggg aggaggggct gtgggtctgg attcctgggt   2280
ctgagggagg aggggctggg ggccttggcc cctgggtctg agggaggagg ggctggggat   2340
ctggactcct gggtctgagg gaggaggggc tggggatctg ggcccctggg tctgagggag   2400
gaggggctgg gtctggaccc ctgggtctga gggaggaggg gctgggggtc tggactcttg   2460
ggtttgaaga aggaagggct ggggtcctgg actcttgggt ctgagttggg agggggcttt   2520
ggcttgggct tctcctgggt ctgagggagg aggtaggctg tgggcttgga ctcccagggc   2580
tgggacagag ccggatggtg ggacagagtc gggtggtggg acagtcccgg gtgggagagg   2640
tcctcgaacc accttatcgc tttcacccct taggtctcct gcagctgaaa gccttgaagc   2700
cgggagttat tcaaatcttg ggagtcaaga catccaggtt cctgtgccag cggccagatg   2760
gggccctgta tggatcggtg agtttccagg accctcctca ccacccacca tgctcctcct   2820
atatgtcgcc ctcacagcct ggggtgcctt gtcttgctca tcccccccgg agccagactt   2880
gattctattt gctctgcacg cccccagctg caacatttgg aggttgaagt tgtcatcagt   2940
gtttgcaaga tgaggaaact gaggcccagg ccggggcgcc agtgacctca atcatgtgat   3000
gtgtggatgc tggagcggcc tgaggctcag gttattggga gtctcgtgat tcagtaaccc   3060
ctgctcctgc ccacacggcc cctgtgtgca cggctcatgc tgggcacagg gacactcggg   3120
gaagccatgg ccagtaaagt gaccaggacc ttgagtgcta gggagacacc ccgcctggcc   3180
tgagagagca ctgatggctc cgagggctgg aatgttctct gtgaagtctg aactgggagg   3240
caggtccctg caggagagcc ctggggtaaa aaacaaaacc tgccttgctg ttttgtttcc   3300
tagaggaggg gctgggggcc tggactcctg ggtctgaggg aggaggggct gggggcctgg   3360
acccctgggt ctgagggagg aggggctggg ggcctggaac cccgggtctg agggaggaga   3420
ggctggggcc tggaaccccg ggtctgaggg aggagaggct ggggcctgga accccgggtc   3480
tgagggagga ggcgctgggg gcctggactc ctgggtcgga tggaggagaa actagggtct   3540
ggacccctgg gtctgaggga ggaggcgctg gggggcctgga cccctgggtc tgagggaggc   3600
agggctgggg cctggatcct gggtcttaca tcaggaaaac agaggaaccc tgtctctgat   3660
cctgtttttg tcccctagct ccactttgac cctgaggcct gcagcttccg ggagctgctt   3720
cttgaggacg gatacaatgt ttaccagtcc gaagcccacg gcctcccgct gcacctgcca   3780
gggaacaagt ccccacaccg ggaccctgca ccccgaggac cagctcgctt cctgccacta   3840
ccaggcctgc cccccgcacc cccggagcca cccggaatcc tggcccccca gcccccccgat   3900
gtgggctcct cggaccctct gagcatggtg ggaccttccc agggccgaag ccccagctac   3960
gcttcctgaa gccagaggct gtttactatg acatctcctc tttatttatt aggttattta   4020
tcttatttat ttttttattt ttcttacttg agataataaa gagttccaga ggaggataag   4080
aatgagcatg tgtgagtgtc tgagggaaga catggcagct gttttgtctc ccttggcccg   4140
gacaatcccc tctacacctc ccctcacgtg gtccgagggt cctggcttcc cactgggcct   4200
cactttttc ttttcttttc ttttttttt tttgagacgg agtctcgctc tgtcacccag   4260
gctggagtgc agtggcgcga tcttggctca ctccaacctc cgcctcccag gttcaagcaa   4320
ttctcctgcc tcagccaccc gagtagctgt gattacaggc gtgcgccacc acacccagct   4380
aattttgtaa ttttagtaga gacagggttt cgccatgttg gccaggatgc tctccatctc   4440
ttgacttcat gacctgcctg ccttggcctc ccaaagtgct gggattacag gcttgagtca   4500
ctgtgcccag cccagcctca cttttctact ctgctaaagt gtccccaggg actgtggact   4560
atccctgctc tctgaaagga caagactggc cgggagtggt ggcttacgcc tgtaatccca   4620
```

```
gcactttggg aggccgaggc aggtggatca cgaggtcagg agattgagac tatcctggct   4680

aatacgatga aaccccgtct ctactaaaaa tacaaaaaca aaattagctg ggcgtggtgg   4740

cgggcgcctg tagtcccagc tactccggag gctgaggcag aatggcgtga atgcgggagg   4800

cggagcttgc agtgagccga gatcgcgcca ctgcactcca gcccaggcca cagagcgaga   4860

ttccatctca aaaaaataaa taaataaata aataaataaa taaatataaa aataaaatga   4920

aagagcagga cttctttcta caacccctca acttgtgtga gcgttgtgta actatttcat   4980

agagctacct caataacagg ggagctttta cgaggtgaca cagcacactc acatcctcat   5040

gggagatgta gttttctggc atcatttagc agcaggaatg agatctgttg ggcctcaaat   5100

ctgggacaag gactcctggg tcctggagta ggtttggggc tagtgtaaca cccaagttct   5160

ggggaatcag tgggctggac atctggacac ctggatcaca ggagaactgg ggactgcaga   5220

cttaggcatc ctggtctgag aaaaaagggg ctggagggtg ggagtttggg ttctcaggaa   5280

aaggagctga aacctggaat tcttccatct gggtccttat gaac                    5324


<210> SEQ ID NO 3
<211> LENGTH: 1332
<212> TYPE: DNA
<213> ORGANISM: Homo sapiens

<400> SEQUENCE: 3

gaggcttcca aggcaggata cttgtgtctc agatgcggtc gcttctttca tacagcaatt     60

gccgccttgc tgaggatcaa ggaacctcag tgtcagatca cgccctcccc ccaaacttag    120

aaattcagat ggggcgcaga aatttctctt gttctgcgtg atctgcatag atggtccaag    180

aggtggtttt tccaggagcc cagcacccct cctccctccg actcagaccc aggagtctgg    240

ccctccattg aaaggacccc aggttacatc atccattcag gctgcccttg ccacgatgga    300

attctgtagc tcctgccaaa tgggtcaaat atcatggttc aggcgcaggg agggtgattg    360

ggcgggcctg tctgggtata aattctggag cttctgcatc tatcccaaaa aacaagggtg    420

ttctgtcagc tgaggatcca gccgaaagag gagccaggca ctcaggccac ctgagtctac    480

tcacctggac aactggaatc tggcaccaat tctaaaccac tcagcttctc cgagctcaca    540

ccccggagat cacctgagga cccgagccat tgatggactc ggacgagacc gggttcgagc    600

actcaggact gtgggtttct gtgctggctg gtcttctgct gggagcctgc caggcacacc    660

ccatccctga ctccagtcct ctcctgcaat tcgggggcca agtccggcag cggtacctct    720

acacagatga tgcccagcag acagaagccc acctggagat cagggaggat gggacggtgg    780

ggggcgctgc tgaccagagc cccgaaagtc tcctgcagct gaaagccttg aagccgggag    840

ttattcaaat cttgggagtc aagacatcca ggttcctgtg ccagcggcca gatggggccc    900

tgtatggatc gctccacttt gaccctgagg cctgcagctt ccgggagctg cttcttgagg    960

acggatacaa tgtttaccag tccgaagccc acggcctccc gctgcacctg ccagggaaca   1020

agtccccaca ccgggaccct gcaccccgag gaccagctcg cttcctgcca ctaccaggcc   1080

tgccccccgc actcccggag ccacccggaa tcctggcccc ccagcccccc gatgtgggct   1140

cctcggaccc tctgagcatg gtgggacctt cccagggccg aagccccact acgcttcctg   1200

aagccagagg ctgtttacta tgacatctcc tctttattta ttaggttatt tatcttattt   1260

atttttttat ttttcttact tgagataata aagagttcca gaggaggata aaaaaaaaaa   1320

aaaaaaaaaa aa                                                       1332
```

<210> SEQ ID NO 4
<211> LENGTH: 947
<212> TYPE: DNA
<213> ORGANISM: Mus musculus

<400> SEQUENCE: 4

```
agacagcctt agtgtcttct cagctgggga ttcaacacag gagaaacagc cattcacttt     60

gcctgagccc cagtctgaac ctgacccatc cctgctgggc accggagtca gaacacaatt    120

ccagctgcct tggctcctca gccgctcgct tgccaggggc tctcccgaac ggagcgcagc    180

cctgatggaa tggatgagat ctagagttgg gaccctggga ctgtgggtcc gactgctgct    240

ggctgtcttc ctgctggggg tctaccaagc ataccccatc cctgactcca gccccctcct    300

ccagtttggg ggtcaagtcc ggcagaggta cctctacaca gatgacgacc aagacactga    360

agcccacctg gagatcaggg aggatggaac agtggtaggc gcagcacacc gcagtccaga    420

aagtctcctg gagctcaaag ccttgaagcc aggggtcatt caaatcctgg gtgtcaaagc    480

ctctaggttt ctttgccaac agccagatgg agctctctat ggatcgcctc actttgatcc    540

tgaggcctgc agcttcagag aactgctgct ggaggacggt tacaatgtgt accagtctga    600

agcccatggc ctgcccctgc gtctgcctca gaaggactcc ccaaaccagg atgcaacatc    660

ctggggacct gtgcgcttcc tgcccatgcc aggcctgctc cacgagcccc aagaccaagc    720

aggattcctg cccccagagc cccagatgt gggctcctct gaccccctga gcatggtaga    780

gcctttacag ggccgaagcc ccagctatgc gtcctgactc ttcctgaatc tagggctgtt    840

tctttttggg tttccactta tttattacgg gtatttatct tatttattta ttttagtttt    900

tttttcttac ttggaataat aaagagtctg aaagaaaaat gtgtgtt                 947
```

<210> SEQ ID NO 5
<211> LENGTH: 210
<212> TYPE: PRT
<213> ORGANISM: Mus musculus

<400> SEQUENCE: 5

```
Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
            20                  25                  30

Pro Asp Ser Ser Pro Leu Leu Gln Phe Gly Gly Gln Val Arg Gln Arg
        35                  40                  45

Tyr Leu Tyr Thr Asp Asp Asp Gln Asp Thr Glu Ala His Leu Glu Ile
    50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
    130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
```

-continued

```
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210


<210> SEQ ID NO 6
<211> LENGTH: 208
<212> TYPE: PRT
<213> ORGANISM: Homo sapiens

<400> SEQUENCE: 6

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Gln Thr Glu Ala His Leu Glu Ile Arg Glu
    50                  55                  60

Asp Gly Thr Val Gly Gly Ala Ala Asp Gln Ser Pro Glu Ser Leu Leu
65                  70                  75                  80

Gln Leu Lys Ala Leu Lys Pro Gly Val Ile Gln Ile Leu Gly Val Lys
                85                  90                  95

Thr Ser Arg Phe Leu Cys Gln Arg Pro Asp Gly Ala Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala His Gly Leu Pro Leu His
    130                 135                 140

Leu Pro Gly Asn Lys Ser Pro His Arg Asp Pro Ala Pro Arg Gly Pro
145                 150                 155                 160

Ala Arg Phe Leu Pro Leu Pro Gly Leu Pro Pro Ala Leu Pro Glu Pro
                165                 170                 175

Pro Gly Ile Leu Ala Pro Gln Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205


<210> SEQ ID NO 7
<211> LENGTH: 3247
<212> TYPE: DNA
<213> ORGANISM: Homo sapiens

<400> SEQUENCE: 7

accctgggcc tggcccaaga aactatacat tcctcctggg aatctggggc tgtgatggga     60

ggggttgcca tgaagacttc tgacatgccc tggagacatt ttccccatgg tcttggggat    120

taacattcag ctccttgtta cttatgcaaa tttctgcagc tggcttgaat ttctcctcag    180

aaaatgagat tttcttttct atcgcattgt caggctgcaa attttccaaa cttttgtgct    240

ctgcttccct tataaaactg aaggcctggc caggtgtggt ggctcacgcc tgtaatccca    300

gcactttggg gagctgagac gggcgaatca cgaggtcagg agttcgagac cagcctggcc    360

aacatggtga aaccctgtct ctactaaaaa tacaaaaagt tagctgggca tagtcatggg    420
```

-continued

```
tgcctttaat cccagctact tgggagactg aggcaggaga atcgtttgaa tccaggaggc    480
ggaggttgca gtgagtcgag atcacaccac tgcactccag ccctggtaac atagtaagac    540
tctgtctcaa aaaaaaaaaa aaaaaaaaca aactgaatgc ctttaacaac acccaagttg    600
cttcttgaat gctttgctgc ttagaaattt cttctgccag ataccctaaa tcatctctct    660
taggttccaa gttccacaaa tctctagggc agggacaaaa cgctgccagt ctctttacta    720
aaacataaca agagtcaccc ttgctctagt tcccaaaaag ttcctcatct ccatctgaaa    780
ccacccccgc ctagatttcg ttgtccatat cattatcagc attttggtca aagtcattca    840
acaggcctct agggagttcc aaacttgctc acattctcct gtcttcttct gagccctcca    900
aactgttcca atccctacct gttacccagt tccaaagtcg cttccacatt tttggttatc    960
ttttcagccg tgccccactc tactggtacc agtttactgt attagtcgat tttcatgctg   1020
ctgataaaga catacctgaa actggacaat ttacaaaaga aagaggttta ttggacttac   1080
aattctacat cacttgggag gcctcacaat catgatggaa ggagaaaggc acatctcaca   1140
tggcagcaga caagaaaaga gcttgtgcag ggaaactcct ctttttaaaa ccatcagatc   1200
tcatgaaatt tattcattat catgacaata gcacaggaaa gaactgcacc cataattcag   1260
tcacctccta ccaggttcct cccacaacac gtgagaattc aagatgagat ttggatgggg   1320
acacagccaa accatgtcac actaccatgc ctgacttcct ttccattttt gtatatttgc   1380
ttgttcttca tttgcccgag aagtaactct aaagggctgt attatttgga tattagattg   1440
gcattttatc tgactgggat atcttgctgt gattgtccat gtataagatc agcttttcta   1500
taaaccatat ttttaaaaag atatattaat tttttaaaaa tccacctgtc taaataaatg   1560
cacaaagccc cccaaaaacc tagattctaa gaaaaatcta tgtactgcca tacaatgatt   1620
gatattaata tttatggtga taaattacac acaaaaaatg tgtgatctct gtttaaacag   1680
gcaaaaacaa aaaacacatg aaataaatct atggcatcta tagccaaaac tggaaacaac   1740
ccacatatcc atcaatagga aatcagttaa ataaattata gtacatttat ccaatggaag   1800
attaagcaca tattcaatat aattatttat acacacatat agatacacac atgtataaat   1860
atagagaata ctgtgggtgt atgtgtgtgt gtgtttatat acatatatat acacacacag   1920
tactgttgcc taccttcttt tgtcttaatt ctgtgaactc tcattcactc tgcttcagta   1980
ggatacatcc ttctttttgg ttcttagact caccaagttg atccttgact caagacattg   2040
catttgctgc ttcctcttcc tggaatatcc ttccttctga tattcacatg agtagtctct   2100
tcttgtcatt cagatctcaa atgtcacaat ttcagagagc ccatctctga tcatcatatc   2160
taaagttgtc ctcattcccc catagctttc tataccatgt tttatttttt tcataacatg   2220
tattttatta ctcctttctc cattggaata gaatctccat tagattagga aatctgccta   2280
tcttattaat gcctgcaact ggaatacttt tgaagagttc ttggcacgta ataaatactc   2340
aactaatatt tttgtgtaca cagaaataaa gtttggaaga acagatgcca aattgttact   2400
agtggttact tctgagtaaa ggagtagcat ggtaggtaaa ttattaatag atgttcactt   2460
tccaccaaga tatgttttag ttagtcttaa cttacttgaa atgaaattta ttactttaat   2520
aattagaaac attgataaac attttagtca caagaatgat agataaaatt ttgatgcttc   2580
caataagtta tatttatcta gaggatgcac ttatgtagaa tactctcttg aggatgttag   2640
gtgagtaaca tgttactata tgtagtaaaa tatctatgat tttataaaag cactgaaaca   2700
tgaagcagca gaaacgtttt tcccagttct ctttcctctg aacttgatca ccgtctctct   2760
```

ggcaaagcac ctaaattaat tcttctttaa aagttaacaa gaccaaatta taagcttgat 2820
gaataactca ttcttatctt tctttaaatg attatagttt atgtatttat tagctatgcc 2880
catcttaaac aggtttattt gttcttttta cacataccaa actcttaata ttagctgttg 2940
tccccaggtc cgaatgttaa gtcaacatat atttgagaga acttcaactt atcaagtatt 3000
gcaggtctct gattgctttg gaaccacttc tgatacctgt ggacttagtt caaggccagt 3060
tactaccact tttttttttc taatagaatg aacaaatggc taattgtttg ctttgtcaac 3120
caagctcaag ttaatggatc tggatactat gtatataaaa agcctagctt gagtctcttt 3180
tcagtggcat ccttcccttt ctaatcagag attttcttcc tcagagattt tggcctagat 3240
ttgcaaa 3247

<210> SEQ ID NO 8
<211> LENGTH: 6079
<212> TYPE: DNA
<213> ORGANISM: Homo sapiens

<400> SEQUENCE: 8
atcctcagtc tcccagttca agctaatcat tgacagagct ttacaatcac aagcttttac 60
tgaagctttg ataagacagt ccagcagttg gtggcaaatg aagccaggct gtgcggcagg 120
atctccaggg aatgaatgga ttttcttcag cactgatgaa ataaccacac gctataggaa 180
tacaatgtcc aacgggggat tgcaaagatc tgtcatcctg tcagcactta ttctgctacg 240
agctgttact ggattctctg gagatggaag agctatatgg tctaaaaatc ctaattttac 300
tccggtaaat gaaagtcagc tgtttctcta tgacactttc cctaaaaact ttttctgggg 360
tattgggact ggagcattgc aagtggaagg gagttggaag aaggatggaa aaggaccttc 420
tatatgggat catttcatcc acacacacct taaaaatgtc agcagcacga atggttccag 480
tgacagttat atttttctgg aaaaagactt atcagccctg gattttatag gagtttcttt 540
ttatcaattt tcaatttcct ggccaaggct tttccccgat ggaatagtaa cagttgccaa 600
cgcaaaaggt ctgcagtact acagtactct tctggacgct ctagtgctta gaaacattga 660
acctatagtt actttatacc actgggattt gcctttggca ctacaagaaa aatatggggg 720
gtggaaaaat gataccataa tagatatctt caatgactat gccacatact gtttccagat 780
gtttggggac cgtgtcaaat attggattac aattcacaac ccatatctag tggcttggca 840
tgggtatggg acaggtatgc atgcccctgg agagaaggga aatttagcag ctgtctacac 900
tgtgggacac aacttgatca aggctcactc gaaagtttgg cataactaca acacacattt 960
ccgcccacat cagaagggtt ggttatcgat cacgttggga tctcattgga tcgagccaaa 1020
ccggtcggaa aacacgatgg atatattcaa atgtcaacaa tccatggttt ctgtgcttgg 1080
atggtttgcc aaccctatcc atggggatgg cgactatcca gaggggatga gaaagaagtt 1140
gttctccgtt ctacccattt tctctgaagc agagaagcat gagatgagag gcacagctga 1200
tttctttgcc ttttcttttg gacccaacaa cttcaagccc ctaaacacca tggctaaaat 1260
gggacaaaat gtttcactta atttaagaga agcgctgaac tggattaaac tggaatacaa 1320
caaccctcga atcttgattg ctgagaatgg ctggttcaca gacagtcgtg tgaaaacaga 1380
agacaccacg gccatctaca tgatgaagaa tttcctcagc caggtgcttc aagcaataag 1440
gttagatgaa atacgagtgt ttggttatac tgcctggtct ctcctggatg gctttgaatg 1500
gcaggatgct tacaccatcc gccgaggatt attttatgtg gattttaaca gtaaacagaa 1560
agagcggaaa cctaagtctt cagcacacta ctacaaacag atcatacgag aaaatggttt 1620

-continued

```
ttctttaaaa gagtccacgc cagatgtgca gggccagttt ccctgtgact tctcctgggg   1680
tgtcactgaa tctgttctta agcccgagtc tgtggcttcg tccccacagt tcagcgatcc   1740
tcatctgtac gtgtggaacg ccactggcaa cagactgttg caccgagtgg aaggggtgag   1800
gctgaaaaca cgacccgctc aatgcacaga ttttgtaaac atcaaaaaac aacttgagat   1860
gttggcaaga atgaaagtca cccactaccg gtttgctctg gattgggcct cggtccttcc   1920
cactggcaac ctgtccgcgg tgaaccgaca ggccctgagg tactacaggt gcgtggtcag   1980
tgaggggctg aagcttggca tctccgcgat ggtcaccctg tattatccga cccacgccca   2040
cctaggcctc cccgagcctc tgttgcatgc cgacgggtgg ctgaacccat cgacggccga   2100
ggccttccag gcctacgctg ggctgtgctt ccaggagctg gggacctgg tgaagctctg   2160
gatcaccatc aacgagccta accggctaag tgacatctac aaccgctctg gcaacgacac   2220
ctacggggcg gcgcacaacc tgctggtggc ccacgccctg gcctggcgcc tctacgaccg   2280
gcagttcagg ccctcacagc gcggggccgt gtcgctgtcg ctgcacgcgg actgggcgga   2340
acccgccaac ccctatgctg actcgcactg gagggcggcc gagcgcttcc tgcagttcga   2400
gatcgcctgg ttcgccgagc cgctcttcaa gaccggggac taccccgcgg ccatgaggga   2460
atacattgcc tccaagcacc gacgggggct ttccagctcg gccctgccgc gcctcaccga   2520
ggccgaaagg aggctgctca agggcacggt cgacttctgc gcgctcaacc acttcaccac   2580
taggttcgtg atgcacgagc agctggccgg cagccgctac gactcggaca gggacatcca   2640
gtttctgcag gacatcaccc gcctgagctc ccccacgcgc ctggctgtga ttccctgggg   2700
ggtgcgcaag ctgctgcggt gggtccggag gaactacggc gacatggaca tttacatcac   2760
cgccagtggc atcgacgacc aggctctgga ggatgaccgg ctccggaagt actacctagg   2820
gaagtacctt caggaggtgc tgaaagcata cctgattgat aaagtcagaa tcaaaggcta   2880
ttatgcattc aaactggctg aagagaaatc taaacccaga tttggattct tcacatctga   2940
ttttaaagct aaatcctcaa tacaatttta caacaaagtg atcagcagca ggggcttccc   3000
ttttgagaac agtagttcta gatgcagtca gacccaagaa aatacagagt gcactgtctg   3060
cttattcctt gtgcagaaga aaccactgat attcctgggt tgttgcttct tctccaccct   3120
ggttctactc ttatcaattg ccatttttca aaggcagaag agaagaaagt tttggaaagc   3180
aaaaaactta caacacatac cattaaagaa aggcaagaga gttgttagct aaactgatct   3240
gtctgcatga tagacagttt aaaaattcat cccagttcca tatgctggta acttacagga   3300
gatatacctg tattatagaa agacaatctg agatacagct gtaaccaagg tgatgacaat   3360
tgtctctgct gtgtggttca aagaacattc ccttaggtgt tgacatcagt gaactcagtt   3420
cttggatgta aacataaagg cttcatcctg acagtaagct atgaggatta catgctacat   3480
tgcttcttaa agtttcatca actgtattcc atcattctgc tttagctttc atctctacca   3540
atagctactt gtggtacaat aaattatttt taagaagtaa aactctgggg ctggacgctg   3600
tggctcacac ctgtaatctc agcactttgg gaggccgagg cggggagatc acctgaggtg   3660
aggagttcga gaccagcctg gccaacatgg tgaaaccatg tctctactaa aaatacaaaa   3720
aattagccag gcgtggtgac agtggcacct gtaatcccag ctacttggga ggctgaggca   3780
gaagtttgaa cccaggaaac aggttacagt aggccaaaat tgcgccactg cactccagcc   3840
taggcgacaa cagcaagact gtgtccaaaa aaaaaaaaaa aagcaaaagc aaaactttgt   3900
tttgttagac tctacagcag agatttaaca cccttcttta aactgggtag tcagtgatag   3960
```

-continued

```
ataatatata ttctgtcact tctaataagg tgccttctcc tttaggtcag ggtggttcta   4020
aaatggaaag aaaacacaat agggtaagta gtgcttgtct aagccagtta caacacagac   4080
tcttaaagag gatcaagccc ttcatttttc taacaacaaa aaatcaccta tagaatatct   4140
aatttgtgat cttttactag atctgatttt ttaaaataat gtaatttccg gccaggcacg   4200
gtggcaccgc ctgtaatccc agcactttgg gaggccaagg caggtggatc acctgaggtt   4260
aggagttcga gactagcctg gccaacatgg caaaacccca tctctactaa aaatacaaaa   4320
gttagccggg catggtggtg ggcacctgta atcccagcta ctcaggaggc cgaggcagga   4380
gaatcgcttg aacccgagag gcagaggttg caatgagcca agatcgtgcc attgcactcc   4440
agcctggggg acagggcaag actgtctctc aaaataaaaa aaaataataa aaataaaaat   4500
aaaagtaatt tccaaaacct catctcatgg aaagatcaca ggatgaagga aagctagact   4560
caactctgtg aatagaagtt gctatactgt aagtaaagca acaattcaga atactgaatg   4620
agtttaaatt gttttatata gcaccctttt gggctagggt taattactag atctgacttg   4680
gataatttga cactttggga aatgaactct gttcttgaga cttgttcagt gtattttaaa   4740
catctgagga agaaaactta aatatgcacc tatttatacc tattctttct ttaggtcaac   4800
atttaacacc cactgcatac attaatttgt ccttgtctgc tcactccagc aatttagacc   4860
ttaacagtca caagagacgt tcttctgtta caaagcctta gtaaattaag gcagttttga   4920
ttatattcta ggtccaccta tgtctgaagc taaattcagt atctaactgc taatgaacaa   4980
gtttccaaaa tactgtaaaa atacaattag tcaatttgag taaatgcaaa tatgatgaga   5040
aatcaatttg ctatttggcc tggcaaatgg gaacagtaaa attctgcttt actcttctct   5100
agtctccttg ccccagctgc acccactacc ccaaagttgg cagttttgag gtatgatttt   5160
caaggaattt ttttagtatt aacatctccc tctgagaact atgtacctaa ggtcacgcat   5220
acaactagtc aattctgttt ttattactct aactatgtag aaacagtaag tcacttaaaa   5280
caatcacttg gctgggtttt ttcccctttg tgccacattg attcaccctg acccaagaac   5340
tccagggaaa attctttaat gtcaactggg caactcatta acctctcttt aacatcaagg   5400
gcttgggaaa aaaaaaaaaa aggttagcca caggaataac aaaaacctgg aatttatctt   5460
tcaggttttg ctttctcttt ctcactttgt ttaaagtatc tcgtactcac agttcacaaa   5520
ttaaccttca ctgtctcttt cacattaaga gcttatgctt aaagcatgcc cccctttttct   5580
aacttgctgg tttaccataa actcccctaa gtaataaaat tcctaaccca gtactgagag   5640
tcctccttct ctgccacttg ggcattattt tactagtttt taagccatca tcgcacaaga   5700
atccaaaaac ccttaaattt tttaaccact ggcaaatatg tacagcaaat taggttaagc   5760
atttaatctg gctcatgctc tatcatacta aatattcagg tttatcataa actccttaaa   5820
aaccatcaaa ggtcaaccag aaactgataa ctcttgaaag gagcaaacag gtaagatctt   5880
tggagtttaa gcttttctga gatgtgttgt gaaaaatcta acgtgtttat cgtatattca   5940
atgtaacaac ctggagaatc acaactatat ttaaagagcc tctggaaaat gaggccagta   6000
cagtgtgact acatgtttaa ttttcaatgt aatttattcc aaataaactg gttcatgctg   6060
accacttgta ttcaactaa                                                 6079
```

<210> SEQ ID NO 9
<211> LENGTH: 1044
<212> TYPE: PRT
<213> ORGANISM: Homo sapiens

<400> SEQUENCE: 9

-continued

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415
```

-continued

```
Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
```

```
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu  Gly Cys Cys Phe Phe  Ser Thr Leu
        995                 1000                1005

Val Leu  Leu Leu Ser Ile Ala  Ile Phe Gln Arg Gln  Lys Arg Arg
    1010                1015                1020

Lys Phe  Trp Lys Ala Lys Asn  Leu Gln His Ile Pro  Leu Lys Lys
    1025                1030                1035

Gly Lys  Arg Val Val Ser
    1040
```

<210> SEQ ID NO 10
<211> LENGTH: 3439
<212> TYPE: DNA
<213> ORGANISM: Mus musculus

<400> SEQUENCE: 10

```
aatgaagaca ggctgtgcag cagggtctcc ggggaatgaa tggattttct tcagctctga     60

tgaaagaaac acacgctcta ggaaaacaat gtccaacagg gcactgcaaa gatctgccgt    120

gctgtctgcg tttgttctgc tgcgagctgt taccggcttc tccggagacg ggaaagcaat    180

atgggataaa aaacagtacg tgagtccggt aaacccaagt cagctgttcc tctatgacac    240

tttccctaaa aacttttcct ggggcgttgg gaccggagca tttcaagtgg aagggagttg    300

gaagacagat ggaagaggac cctcgatctg ggatcggtac gtctactcac acctgagagg    360

tgtcaacggc acagacagat ccactgacag ttacatcttt ctggaaaaag acttgttggc    420

tctggatttt ttaggagttt ctttttatca gttctcaatc tcctggccac ggttgtttcc    480

caatggaaca gtagcagcag tgaatgcgca aggtctccgg tactaccgtg cacttctgga    540

ctcgctggta cttaggaata tcgagcccat tgttaccttg taccattggg atttgcctct    600

gacgctccag gaagaatatg gggctggaa aaatgcaact atgatagatc tcttcaacga    660

ctatgccaca tactgcttcc agacctttgg agaccgtgtc aaatattgga ttacaattca    720

caacccttac cttgttgctt ggcatgggtt tggcacaggt atgcatgcac caggagagaa    780

gggaaattta acagctgtct acactgtggg acacaacctg atcaaggcac attcgaaagt    840

gtggcataac tacgacaaaa acttccgccc tcatcagaag ggttggctct ccatcacctt    900
```

-continued

```
ggggtcccat tggatagagc caaacagaac agacaacatg gaggacgtga tcaactgcca    960
gcactccatg tcctctgtgc ttggatggtt cgccaacccc atccacgggg acggcgacta   1020
ccctgagttc atgaagacgg gcgccatgat ccccgagttc tctgaggcag agaaggagga   1080
ggtgaggggc acggctgatt tctttgcctt ttccttcggg cccaacaact tcaggccctc   1140
aaacaccgtg gtgaaaatgg gacaaaatgt atcactcaac ttaaggcagg tgctgaactg   1200
gattaaactg gaatacgatg accctcaaat cttgatttcg gagaacggct ggttcacaga   1260
tagctatata aagacagagg acaccacggc catctacatg atgaagaatt tcctaaacca   1320
ggttcttcaa gcaataaaat ttgatgaaat ccgcgtgttt ggttatacgg cctggactct   1380
cctggatggc tttgagtggc aggatgccta tacgacccga cgagggctgt tttatgtgga   1440
ctttaacagt gagcagaaag agaggaaacc caagtcctcg gctcattact acaagcagat   1500
catacaagac aacggcttcc ctttgaaaga gtccacgcca gacatgaagg gtcggttccc   1560
ctgtgatttc tcttggggag tcactgagtc tgttcttaag cccgagttta cggtctcctc   1620
cccgcagttt accgatcctc acctgtatgt gtggaatgtc actggcaaca gattgctcta   1680
ccgagtggaa ggggtaaggc tgaaaacaag accatcccag tgcacagatt atgtgagcat   1740
caaaaaacga gttgaaatgt tggcaaaaat gaaagtcacc cactaccagt ttgctctgga   1800
ctggacctct atccttccca ctggcaatct gtccaaagtt aacagacaag tgttaaggta   1860
ctataggtgt gtggtgagcg aaggactgaa gctgggcgtc ttccccatgg tgacgttgta   1920
ccacccaacc cactcccatc tcggcctccc cctgccactt ctgagcagtg gggggtggct   1980
aaacatgaac acagccaagg ccttccagga ctacgctgag ctgtgcttcc gggagttggg   2040
ggacttggtg aagctctgga tcaccatcaa tgagcctaac aggctgagtg acatgtacaa   2100
ccgcacgagt aatgacacct accgtgcagc ccacaacctg atgatcgccc atgcccaggt   2160
ctggcacctc tatgataggc agtataggcc ggtccagcat ggggctgtgt cgctgtcctt   2220
acattgcgac tgggcagaac ctgccaaccc ctttgtggat tcacactgga aggcagccga   2280
gcgcttcctc cagtttgaga tcgcctggtt tgcagatccg ctcttcaaga ctggcgacta   2340
tccatcggtt atgaaggaat acatcgcctc caagaaccag cgagggctgt ctagctcagt   2400
cctgccgcgc ttcaccgcga aggagagcag gctggtgaag ggtaccgtcg acttctacgc   2460
actgaaccac ttcactacga ggttcgtgat acacaagcag ctgaacacca accgctcagt   2520
tgcagacagg gacgtccagt tcctgcagga catcacccgc ctaagctcgc ccagccgcct   2580
ggctgtaaca ccctggggag tgcgcaagct ccttgcgtgg atccggagga actacagaga   2640
cagggatatc tacatcacag ccaatggcat cgatgacctg gctctagagg atgatcagat   2700
ccgaaagtac tacttggaga agtatgtcca ggaggctctg aaagcatatc tcattgacaa   2760
ggtcaaaatc aaaggctact atgcattcaa actgactgaa gagaaatcta agcctagatt   2820
tggatttttc acctctgact tcagagctaa gtcctctgtc cagttttaca gcaagctgat   2880
cagcagcagt ggcctccccg ctgagaacag aagtcctgcg tgtggtcagc ctgcggaaga   2940
cacagactgc accatttgct catttctcgt ggagaagaaa ccactcatct tcttcggttg   3000
ctgcttcatc tccactctgg ctgtactgct atccatcacc gtttttcatc atcaaaagag   3060
aagaaaattc cagaaagcaa ggaacttaca aaatatacca ttgaagaaag gccacagcag   3120
agttttcagc taaactgcca tttctgtcat agtttcaaga ttcactccgg ctccatgtac   3180
tggtaactta cgatgtgaga gacagctgta accaaggtga agacaatcga tgcctctgaa   3240
gtgtggttca aataattcct tcaggtcccg acaatcagtg agtccgttct ccgagctgaa   3300
```

```
gacaccctga cagtaactct gggcgtgacc ctaaacatcg cttcaggaag tgtgaatcac   3360

gacttcacat cctttttctc tagcattctt ctgtaaataa caatcactat tcatggtcaa   3420

gaaattaatt ttaaaaagt                                                3439


<210> SEQ ID NO 11
<211> LENGTH: 1040
<212> TYPE: PRT
<213> ORGANISM: Mus musculus

<400> SEQUENCE: 11

Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Ala
        35                  40                  45

Val Thr Gly Ser Gly Asp Gly Lys Ala Trp Asp Lys Lys Gln Tyr Val
    50                  55                  60

Ser Pro Val Asn Pro Ser Gln Leu Phe Leu Tyr Asp Thr Phe Pro Lys
65                  70                  75                  80

Asn Phe Ser Trp Gly Val Gly Thr Gly Ala Phe Gln Val Glu Gly Ser
                85                  90                  95

Trp Lys Thr Asp Gly Arg Gly Pro Ser Ile Trp Asp Arg Tyr Val Tyr
            100                 105                 110

Ser His Leu Arg Gly Val Asn Gly Thr Asp Arg Ser Thr Asp Ser Tyr
        115                 120                 125

Ile Phe Leu Glu Lys Asp Leu Leu Ala Leu Asp Phe Leu Gly Val Ser
    130                 135                 140

Phe Tyr Gln Phe Ser Ile Ser Trp Pro Arg Leu Phe Pro Asn Gly Thr
145                 150                 155                 160

Val Ala Ala Val Asn Ala Gln Gly Leu Arg Tyr Tyr Arg Ala Leu Leu
                165                 170                 175

Asp Ser Leu Val Leu Arg Asn Ile Glu Pro Ile Val Thr Leu Tyr His
            180                 185                 190

Trp Asp Leu Pro Leu Thr Leu Gln Glu Glu Tyr Gly Gly Trp Lys Asn
        195                 200                 205

Ala Thr Met Ile Asp Leu Phe Asn Asp Tyr Ala Thr Tyr Cys Phe Gln
    210                 215                 220

Thr Phe Gly Asp Arg Val Lys Tyr Trp Ile Thr Ile His Asn Pro Tyr
225                 230                 235                 240

Leu Val Ala Trp His Gly Phe Gly Thr Gly Met His Ala Pro Gly Glu
                245                 250                 255

Lys Gly Asn Leu Thr Ala Val Tyr Thr Val Gly His Asn Leu Ile Lys
            260                 265                 270

Ala His Ser Lys Val Trp His Asn Tyr Asp Lys Asn Phe Arg Pro His
        275                 280                 285

Gln Lys Gly Trp Leu Ser Ile Thr Leu Gly Ser His Trp Ile Glu Pro
    290                 295                 300

Asn Arg Thr Asp Asn Met Glu Asp Val Ile Asn Cys Gln His Ser Met
305                 310                 315                 320

Ser Ser Val Leu Gly Trp Phe Ala Asn Pro Ile His Gly Asp Gly Asp
                325                 330                 335

Tyr Pro Glu Phe Met Lys Thr Gly Ala Met Ile Pro Glu Phe Ser Glu
```

```
            340                 345                 350

Ala Glu Lys Glu Glu Val Arg Gly Thr Ala Asp Phe Phe Ala Phe Ser
        355                 360                 365

Phe Gly Pro Asn Asn Phe Arg Pro Ser Asn Thr Val Val Lys Met Gly
    370                 375                 380

Gln Asn Val Ser Leu Asn Leu Arg Gln Val Leu Asn Trp Ile Lys Leu
385                 390                 395                 400

Glu Tyr Asp Asp Pro Gln Ile Leu Ile Ser Glu Asn Gly Trp Phe Thr
                405                 410                 415

Asp Ser Tyr Ile Lys Thr Glu Asp Thr Thr Ala Ile Tyr Met Met Lys
            420                 425                 430

Asn Phe Leu Asn Gln Val Leu Gln Ala Ile Lys Phe Asp Glu Ile Arg
        435                 440                 445

Val Phe Gly Tyr Thr Ala Trp Thr Leu Leu Asp Gly Phe Glu Trp Gln
    450                 455                 460

Asp Ala Tyr Thr Thr Arg Arg Gly Leu Phe Tyr Val Asp Phe Asn Ser
465                 470                 475                 480

Glu Gln Lys Glu Arg Lys Pro Lys Ser Ser Ala His Tyr Tyr Lys Gln
                485                 490                 495

Ile Ile Gln Asp Asn Gly Phe Pro Leu Lys Glu Ser Thr Pro Asp Met
            500                 505                 510

Lys Gly Arg Phe Pro Cys Asp Phe Ser Trp Gly Val Thr Glu Ser Val
        515                 520                 525

Leu Lys Pro Glu Phe Thr Val Ser Ser Pro Gln Phe Thr Asp Pro His
    530                 535                 540

Leu Tyr Val Trp Asn Val Thr Gly Asn Arg Leu Leu Tyr Arg Val Glu
545                 550                 555                 560

Gly Val Arg Leu Lys Thr Arg Pro Ser Gln Cys Thr Asp Tyr Val Ser
                565                 570                 575

Ile Lys Lys Arg Val Glu Met Leu Ala Lys Met Lys Val Thr His Tyr
            580                 585                 590

Gln Phe Ala Leu Asp Trp Thr Ser Ile Leu Pro Thr Gly Asn Leu Ser
        595                 600                 605

Lys Val Asn Arg Gln Val Leu Arg Tyr Tyr Arg Cys Val Val Ser Glu
    610                 615                 620

Gly Leu Lys Leu Gly Val Phe Pro Met Val Thr Leu Tyr His Pro Thr
625                 630                 635                 640

His Ser His Leu Gly Leu Pro Leu Pro Leu Leu Ser Ser Gly Gly Trp
                645                 650                 655

Leu Asn Met Asn Thr Ala Lys Ala Phe Gln Asp Tyr Ala Glu Leu Cys
            660                 665                 670

Phe Arg Glu Leu Gly Asp Leu Val Lys Leu Trp Ile Thr Ile Asn Glu
        675                 680                 685

Pro Asn Arg Leu Ser Asp Met Tyr Asn Arg Thr Ser Asn Asp Thr Tyr
    690                 695                 700

Arg Ala Ala His Asn Leu Met Ile Ala His Ala Gln Val Trp His Leu
705                 710                 715                 720

Tyr Asp Arg Gln Tyr Arg Pro Val Gln His Gly Ala Val Ser Leu Ser
                725                 730                 735

Leu His Cys Asp Trp Ala Glu Pro Ala Asn Pro Phe Val Asp Ser His
            740                 745                 750

Trp Lys Ala Ala Glu Arg Phe Leu Gln Phe Glu Ile Ala Trp Phe Ala
        755                 760                 765
```

```
Asp Pro Leu Phe Lys Thr Gly Asp Tyr Pro Ser Val Met Lys Glu Tyr
    770                 775                 780

Ile Ala Ser Lys Asn Gln Arg Gly Leu Ser Ser Ser Val Leu Pro Arg
785                 790                 795                 800

Phe Thr Ala Lys Glu Ser Arg Leu Val Lys Gly Thr Val Asp Phe Tyr
                805                 810                 815

Ala Leu Asn His Phe Thr Thr Arg Phe Val Ile His Lys Gln Leu Asn
            820                 825                 830

Thr Asn Arg Ser Val Ala Asp Arg Asp Val Gln Phe Leu Gln Asp Ile
        835                 840                 845

Thr Arg Leu Ser Ser Pro Ser Arg Leu Ala Val Thr Pro Trp Gly Val
    850                 855                 860

Arg Lys Leu Leu Ala Trp Ile Arg Arg Asn Tyr Arg Asp Arg Asp Ile
865                 870                 875                 880

Tyr Ile Thr Ala Asn Gly Ile Asp Asp Leu Ala Leu Glu Asp Asp Gln
                885                 890                 895

Ile Arg Lys Tyr Tyr Leu Glu Lys Tyr Val Gln Glu Ala Leu Lys Ala
            900                 905                 910

Tyr Leu Ile Asp Lys Val Lys Ile Lys Gly Tyr Tyr Ala Phe Lys Leu
        915                 920                 925

Thr Glu Glu Lys Ser Lys Pro Arg Phe Gly Phe Phe Thr Ser Asp Phe
    930                 935                 940

Arg Ala Lys Ser Ser Val Gln Phe Tyr Ser Lys Leu Ile Ser Ser Ser
945                 950                 955                 960

Gly Leu Pro Ala Glu Asn Arg Ser Pro Ala Cys Gly Gln Pro Ala Glu
                965                 970                 975

Asp Thr Asp Cys Thr Ile Cys Ser Phe Leu Val Glu Lys Lys Pro Leu
            980                 985                 990

Ile Phe Phe Gly Cys Cys Phe Ile  Ser Thr Leu Ala Val  Leu Leu Ser
        995                 1000                1005

Ile Thr  Val Phe His His Gln  Lys Arg Arg Lys Phe  Gln Lys Ala
    1010                1015                1020

Arg Asn  Leu Gln Asn Ile Pro  Leu Lys Lys Gly His  Ser Arg Val
    1025                1030                1035

Phe Ser
    1040
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
actctgcgct ggttgaaaaa t 21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 13

-continued ggtggcatag cgaaccttgt a 21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gctataaggt acgaaaccag cac 23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ggttgatgga cccgtattca ttc 23

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gcctgcgtgc tagtgttct 19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
taccatcctt agcccagacc g 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tccatgaccg tcgtacacaa t 21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
atttgacagt attcccggca g 21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
tgttctgctg cgagctgtta c 21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
ccggactcac gtactgtttt t 21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
gaagccgctt atgtgtatcg c 21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
gaatgggtac attgggaaca gt 22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
ggagatcctt cgaggagcac tt 22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
gcgatttagc agcagatata agaa 24

-continued

```
<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

aaggacctgg tacatgaact gg                                             22


<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

ggttctgggt gtcaagtgtc g                                              21


<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

tttggcgttc gaggccatt                                                 19


<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

caggtccacg catttcagac                                                20


<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

cagacgccac tgtcgcttt                                                 19


<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

tgtctttgga actttgtctg caa                                            23
```

-continued

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gagcaagggc tgctactcaa g 21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
aaccgcaggt tcaagtattc c 21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
tcatggtctt cggaggattc ac 22

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
tcacctccaa gtgtggcaaa g 21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ttcaggcagg cagtatcact c 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gaaggtccac gggaaagaca c 21

<210> SEQ ID NO 38

-continued

<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
aagagccgga aatccacgaa a 21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
gtctcaaaag ggtcagggta ct 22

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
cttactgact ggcatgagga tca 23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
gcagctctag gagcatgtgg 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
gaagccgctt atgtgtatcg c 21

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
gaatgggtac attgggaaca gt 22

<210> SEQ ID NO 44
<211> LENGTH: 22

<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
tagatgacca tgagtcgctt gc 22

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
gccaaacttg ctccatgtcc 20

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
ggagagtctg actctccctg agaa 24

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
cgatgggttc cgtcttggt 19

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
cggttccgat gccctgaggc tctt 24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
cgtcacactt catgatggaa ttga 24